US006258817B1

(12) United States Patent
Bradbury et al.

(10) Patent No.: US 6,258,817 B1
(45) Date of Patent: Jul. 10, 2001

(54) SUBSTITUTED PYRAZIN-2-YL-SULPHONAMIDE (-3-PYRIDYL) COMPOUNDS AND USES THEREOF

(75) Inventors: Robert Hugh Bradbury, Wilmslow; Roger John Butlin, Macclesfield; Roger James, Congleton, all of (GB)

(73) Assignee: Zeneca Ltd. (GB)

( * ) Notice: Subject to any disclaimer, the term of this patent is extended or adjusted under 35 U.S.C. 154(b) by 0 days.

(21) Appl. No.: 09/504,364

(22) Filed: Feb. 15, 2000

Related U.S. Application Data

(62) Division of application No. 09/211,483, filed on Dec. 14, 1998, now Pat. No. 6,060,475, which is a division of application No. 08/658,969, filed on Jun. 4, 1996, now Pat. No. 5,866,568.

(30) Foreign Application Priority Data

Jun. 7, 1995 (GB) .................................................. 9511507
Sep. 27, 1995 (GB) .................................................. 9519666

(51) Int. Cl.[7] .................. A01N 43/60; A61K 31/495; C07D 417/00; C07D 413/00; C07D 401/00
(52) U.S. Cl. ........................ 514/255.05; 514/255.06; 514/227.8; 514/235.5; 514/235.8; 544/60; 544/111; 544/360; 544/405
(58) Field of Search ........................ 514/235.5, 235.8, 514/227.8, 255.05, 255.06; 544/60, 111, 360, 405

(56) References Cited

U.S. PATENT DOCUMENTS

| 5,270,313 | 12/1993 | Burri et al. ............................ 514/252 |
| 5,292,740 | 3/1994 | Burri et al. ............................ 514/252 |
| 5,420,129 | 5/1995 | Breu et al. ............................ 514/252 |
| 5,464,853 | 11/1995 | Chan et al. ............................ 514/378 |
| 5,514,691 | 5/1996 | Chan et al. ............................ 514/312 |
| 5,571,821 | 11/1996 | Chan et al. ............................ 514/312 |
| 5,591,761 | 1/1997 | Chan et al. ............................ 514/380 |
| 5,594,021 | 1/1997 | Chan et al. ............................ 514/378 |
| 5,939,359 | 8/1999 | Engel et la. ............................ 504/221 |

FOREIGN PATENT DOCUMENTS

| 0 510526 | 10/1992 | (EP) . |
| 0 526708 | 2/1993 | (EP) . |
| 0 558258 | 9/1993 | (EP) . |
| 0 569193 | 11/1993 | (EP) . |
| 0 601386 | 6/1994 | (EP) . |
| 0 6400596 | 3/1995 | (EP) . |
| 0 626 174 | 1/1996 | (EP) . |
| 0702012 | 3/1996 | (EP) . |
| 0 682016 | 11/1996 | (EP) . |
| 2 295 616 | 6/1996 | (GB) . |
| 61-257960 | 11/1986 | (JP) . |
| WO 9009787 | 9/1990 | (WO) . |
| WO 9427979 | 11/1994 | (WO) . |
| WO 9526957 | 10/1995 | (WO) . |
| WO 96/31492 | 10/1996 | (WO) . |

OTHER PUBLICATIONS

R.D. Desai et al., "Studies in Sulphonamides: Part II. Preparation of N[1]–Heterocyclic Substituted Sulphonamides from Alpha–naphthylamine and Evaluation of their Antibacterial Properties", *Jour. Indian Chem. Soc.*, pp. 115–118, vol. 46, No. 2, 1969.
R.D. Desai et al., "Studies in Sulphonamides: Part IV. Some N[6]–Heterocyclic Sulphonamides from 2–Naphthylamine as possible Antibacterial Agents", *J. Indian Chem. Soc.*, pp. 411–414, vol. 46, No. 5, 1969.
P. Mamalis et al., "142. Some Heterocyclic N–Oxides", *J. Chem. Soc.*, pp. 703–705, 1950.
*Chemical Abstracts*, vol. 84, No. 15, 1976, 84:100672y, p. 162.
*Chemical Abstracts*, vol. 100, No. 15, 1984, 100:131420t, p. 672.
*Chemical Abstracts*, vol. 106, No. 17, 1987, 106:133792p (corresponds to JP61257960), p. 268.
Himel et al., "Fluorescent Analogs of Insecticides and Synergists, Synthesis and Reactions of Active–Site Directed Fluorescent Probes", *Journal Agr. Food Chem.*, vol. 19, No. 6, 1971, pp. 1175–1180.
Shigehara et al., "Preparation of Pyridine Derivatives and their Salts as Phospholipase $A_2$ Inhibitors", *Chemical Abstracts*, vol. 122, No. 25, 1995, 122:314455g, p. 929.
The Discovery of Sulfonamide Endothelin Antagonists and the Development of the Orally Active $ET_A$ Antagonist 5–(Dimethylamino)–N–(3, 4–dimethyl–5–isoxazoly)–1–naphthalenesul fonamide, *Journal of Medicinal Chemistry*, Feb. 4, 1994, vol. 37, No. 3, pp. 329–331, (Stein et al.).
Chan et al., Identification of a New Class of $ET_A$ Selective Endothelin Antagonists by Pharmacophore Directed Screening, *Biochemical and Biophysical Research Communications*, May 30, 1994, vol. 201, No. 1, pp. 228–234.
Pharmacological Characterization of Bosentan, a New Potent Orally Active Nonpeptide Endothelin Receptor Antagonist, *Journal Pharmacol. Exp. Therap.*, 1994, 270, 228–235, (Clozel et al.).
Pages copied from a book of abstracts provided in an International Business Communications Conference entitled "Endothelin Inhibitors—Advances in Therapeutic Application and Development", Philadelphia, PA, Jun. 9–10, 1994, 33 pages.

*Primary Examiner*—Mukund J. Shah
*Assistant Examiner*—Tamthom N. Truong
(74) *Attorney, Agent, or Firm*—Kenneth F. Mitchell

(57) ABSTRACT

The invention concerns pharmaceutically useful compounds of the formula I, in which $A^1$, $A^2$, $A^3$, $A^4$, $B^1$, m, Ar, W, X, Y, Z and $R^1$ have any of the meanings defined herein, and their pharmaceutically acceptable salts, and pharmaceutical compositions containing them. The novel compounds possess endothelin receptor antagonist activity and are useful, for example, in the treatment of diseases or medical conditions in which elevated or abnormal levels of endothelin play a significant causative role. The invention further concerns processes for the manufacture of the novel compounds and the use of the compounds in medical treatment.

8 Claims, No Drawings

SUBSTITUTED PYRAZIN-2-YL-SULPHONAMIDE (-3-PYRIDYL) COMPOUNDS AND USES THEREOF

This is a division of prior application Ser. No. 09/211,483, filed Dec. 14, 1998, now U.S. Pat. No. 6,060,475, which is a division of application Ser. No. 8/658,969, filed Jun. 4, 1996, now U.S. Pat. No. 5,866,568.

The present invention relates to novel heterocyclic compounds and, more particularly, to novel N-heterocyclyl sulphonamides, and pharmaceutically-acceptable salts thereof, which possess endothelin receptor antagonist activity. These compounds are of value whenever such antagonist activity is desired, such as for research tools within pharmacological, diagnostic and related studies or in the treatment of diseases or medical conditions including, but not limited to, hypertension, pulmonary hypertension, cardiac or cerebral circulatory disease and renal disease, in warm-blooded animals (including man), in which elevated or abnormal levels of endothelin play a significant causative role. The invention also relates to pharmaceutical compositions of the novel compounds (and their salts) for use in treating said diseases or medical conditions, and to processes for the manufacture of the novel compounds. The invention further relates to the use of the novel compounds in treating one or more of the said diseases or medical conditions. A method of treating one or more of the said diseases or medical conditions using said compounds is also provided.

The endothelins are a family of endogenous 21 amino acid peptides comprising three isoforms, endothelin-1, endothelin-2 and endothelin-3. The endothelins are formed by cleavage of the $Trp^{21}$-$Val^{22}$ bond of their corresponding proendothelins by a putative endothelin converting enzyme. The endothelins are among the most potent vasoconstrictors known and have a characteristic long duration of action. They exhibit a wide range of other activities including cell proliferation and mitogenesis, extravasation and chemotaxis, and also interact with a number of other vasoactive agents. They also have direct effects on the heart. Thus the biological profile of the endothelins is consistent with a pathophysiological role in the cardiovascular system. The endothelins also have actions on other physiological systems including the airways, gastro-intestinal tract, reproductive system, kidney, liver, central nervous system, neuro-endocrine system and the blood.

The endothelins are released from a range of tissue and cell sources including vascular endothelium, vascular smooth muscle, kidney, liver, uterus, airways, intestine and leukocytes. Release can be stimulated by hypoxia, shear stress, physical injury and a wide range of hormones and cytokines. Elevated endothelin levels have been found in a number of disease states in man including hypertension, pulmonary hypertension, pre-eclampsia, congestive heart failure, myocardial infarction, angina pectoris, acute and chronic renal failure, ischaemic stroke, subarachnoid haemorrhage, atherosclerosis, hypercholesterolaemia, cardiogenic and endotoxic shock, diabetes mellitus, Raynaud's disease, scleroderma, systemic sclerosis, Buerger's disease, rheumatoid arthritis, asthma, bronchitis, acute respiratory failure, liver cirrhosis, Crohn's disease, ulcerative colitis, certain cancers and after surgery.

In European patent applications, publication nos. 558258 and 569193, and in International patent application, publication no. WO 94/27979, are described certain N-(isozaxolyl)sulphonamides and in European patent application, publication no. 640596 are described certain N-(pyridazinyl)sulphonamides, which are referred to as endothelin receptor antagonists.

Although a number of endothelin receptor antagonists are known, there is a continuing need for alternative antagonists. The present invention is based in part on this need and on our discovery of the unexpected antagonism of the endothelin receptor by certain N-heterocyclyl sulphonamides.

According to one aspect of the invention there is provided a compound of the formula I (set our hereinafter, together with the other chemical formulae identified by Roman numerals) wherein one of $A^1$, $A^2$, $A^3$ and $A^4$ is nitrogen and the remainder of $A^1$, $A^2$, $A^3$ and A are CH; Ar is a phenyl group which is unsubstituted or bears 1, 2 or 3 substituents independently selected from (1–6C)alkyl, amino(1–6C)alkyl, hydroxy(1–6C)alkyl, N-[(1–4C)alkyl]amino(1–6C)alkyl, N,N-[di(1–4C)alkyl]amino(1–6C)alkyl, carboxy(1–6C)alkyl, (1–6C)alkoxycarbonyl(1–6C)alkyl, (1–6C)alkylcarbonyloxy(1–6C)alkyl, carbamoyl(1–6C)alkyl, N-(1–6C)alkylcarbamoyl(1–6C)alkyl, di-N-(1–6C)alkylcarbamoyl(1–6C)alkyl, N-(1–6C)alkylcarbamoyloxy(1–6C)alkyl, carboxy(1–6C)alkoxy, carboxy(1–6C)alkylthio, (1–6C)alkoxycarbonyl(1–6C)alkoxy, (1–6C)alkoxycarbonyl(1–6C)alkylthio, carbamoyl(1–6C)alkoxy, (1–6C)alkylcarbamoyl(1–6C)alkoxy, di(1–6C)alkylcarbamoyl(1–6C)alkoxy, carbamoyl(1–6C)alkylthio, (1–6C)alkylcarbamoyl(1–6C)alkylthio, di(1–6C)alkylcarbamoyl(1–6C)alkylthio, (2–6C)alkenyl, carboxy(2–6C)alkenyl, (2–6C)alkynyl, carboxy(2–6C)alkynyl, halogeno(2–6C)alkyl, trifluoromethyl, trichloromethyl, tribromomethyl, (1–6C)alkoxy, hydroxy(1–6C)alkoxy, dihalogeno(1–6C)alkoxy, trihalogeno(1–6C)alkoxy, (2–6C)alkenyloxy(1–6C)alkyl, (2–6C)alkenyloxy, (1–4C)alkoxy(1–6C)alkyl, (1–6C)alkoxycarbonyl(1–6C)alkoxy(1–6C)alkyl, carboxy(1–6C)alkoxy(1–6C)alkyl, hydroxy(1–6C)alkoxy(1–6C)alkyl, (1–4C)alkylthio(1–6C)alkyl, (1–4C)alkylsulphinyl(1–6C)alkyl, (1–4C)alkylsulphonyl(1–6C)alkyl, (1–4C)alkylenedioxy, (3–6C)cycloalkyl, (3–8C)cycloalkyl(1–6C)alkyl, phenyl, phenyl(1–6C)alkyl, phenoxy, phenyl(1–6C)alkoxy, pyridyl(1–6C)alkoxy(1–6C)alkyl, halogeno, hydroxy, mercapto, cyano, nitro, carboxy, (1–6C)alkoxycarbonyl, (2–6C)alkenyloxycarbonyl, phenyloxycarbonyl, phenyl(1–6C)alkoxycarbonyl, (1–6C)alkanoyl, benzoyl, (1–6C)alkylthio, (1–6C)alkylsulphinyl, (1–6C)alkylsulphonyl, phenylthio, phenylsulphinyl, phenylsulphonyl, (1–6C)alkanoylamino, trifluoroacetyl, trifluoroacetamido, N-[(1–4C)alkyl]trifluoroacetamido, benzamido, N-[(1–4C)alkyl]benzamido, carbamoyl, (1–4C)alkylcarbamoyl, di-(1–4C)alkylcarbamoyl, phenylcarbamoyl, sulphamoyl, N-(1–4C)alkylsulphamoyl, N,N-di(1–4C)alkylsulphamoyl, N-phenylsulphamoyl, (1–6C)alkanesulphonamido, benzenesulphonamido, ureido, 3-(1–6C)alkylureido, 3-phenylureido, thioureido, 3-(1–6C)alkylthioureido, 3-phenylthioureido, a five membered heterocyclyl group containing 1, 2, 3 or 4 heteroatoms independently selected from nitrogen, oxygen and sulphur, a six membered heterocyclyl group containing 1, 2 or 3 heteroatoms independently selected from nitrogen, oxygen and sulphur, and a group —NRaRb in which Ra and Rb are independently selected from hydrogen, (1–6C)alkyl, phenyl (1–4C)alkyl and (1–6C)alkyl bearing a carboxy, (1–6C) alkoxycarbonyl, carbamoyl, (1–6C)alkylcarbamoyl or di(1–6C)alkylcarbamoyl group, or the group —NRaRb taken together complete a 1-pyrrolidinyl, 2-oxo-1-pyrrolidinyl, 1-piperidinyl, 2-oxo-1-piperidinyl, morpholino or thiamorpholino ring;

$B^1$ is an optional substituent on a carbon atom of $A^1$, $A^2$, $A^3$ or $A^4$ selected from (1–4C)alkyl, halogeno and (1–4C)alkoxy; m is zero, 1, 2 or 3; the ring containing W, X, Y and Z and bearing substituent $R^1$ is selected from:

(a) a ring in which W is nitrogen; X is CH; Y is nitrogen; and Z is CRy in which Ry is hydrogen, halogeno, (1–4C)alkyl, (1–4C)alkoxy or trifluoromethoxy; and substituent $R^1$ is hydrogen, halogeno, (1–4C)alkyl, methoxy, ethoxy, trifluoromethyl or ethynyl;

(b) a ring in which W is CRz in which Rz is hydrogen, halogeno, (1–4C)alkyl, (1–4C)alkoxy or trifluoromethoxy; X is nitrogen; Y is nitrogen; and Z is CH; and substituent $R^1$ is halogeno, (1–4C)alkyl, methoxy, ethoxy, trifluoromethyl or ethynyl; and (c) a ring in which W and X are both nitrogen; Y is CH; and Z is CRx in which Rx is hydrogen, halogeno, (1–4C)alkyl, (1–4C)alkoxy or trifluoromethoxy; and substituent $R^1$ is halogeno, (1–4C)alkyl, methoxy, ethoxy, trifluoromethyl or ethynyl; and wherein any of said phenyl or benzene or heterocyclyl moieties of a substituent on Ar may be unsubstituted or bear one or two substituents independently selected from (1–4C)alkyl, (1–4C)alkoxy, halogeno, cyano, carboxy and trifluoromethyl; or an N-oxide thereof; or a pharmaceutically-acceptable salt thereof.

According to a further aspect of the present invention there is provided a compound of the formula I, or an N-oxide or a pharmaceutically acceptable salt thereof, as defined above, but excluding compounds and N-oxides thereof and pharmaceutically acceptable salts thereof in which Ar bears a (1–6C)alkylcarbonyloxy(1–6C)alkyl, N-(1–6C) alkylcarbamoyloxy(1–6C)alkyl, hydroxy(1–6C)alkoxy, (2–6C)alkenyloxy(1–6C)alkyl, (1–6C)alkoxycarbonyl (1–6C)alkoxy-(1–6C)alkyl, carboxy(1–6C)alkoxy(1–6C) alkyl, hydrox 6C)alkoxy(1–6C)alkyl, pyridyl-(1–6C)alkoxy (1–6C)alkyl, a substituted or unsubstituted five membered heterocyclyl group containing 1, 2, 3 or 4 heteroatoms independently selected from nitrogen, oxygen and sulphur, a substituted or unsubstituted six membered heterocyclyl group containing 1, 2 or 3 heteroatoms independently selected from nitrogen, oxygen and sulphur, or a morpholino or thiamorpholino ring; and excluding compounds and N-oxides thereof and pharmaceutically acceptable salts thereof wherein a phenyl or benzene moiety of a substituent on Ar bears a carboxy group.

It will be appreciated that, depending on the nature of the substituents, certain of the formula I compounds may possess one or more chiral centres and may be isolated in one or more racemic or optically active forms. It is to be understood that the present invention concerns any form of such a compound of formula I which possesses the aforementioned useful pharmacological properties, it being well known how to make optically active forms, for example by synthesis from suitable chiral intermediates or by resolution, and how to determine their pharmacological properties, for example by use of the tests described hereinafter.

It will also be appreciated that a compound of formula I may exhibit polymorphism, that a compound of formula I may form a solvate and that a compound of formula I may exist in more than one tautomeric form. It is to be understood that the present invention also concerns any polymorphic form, any tautomer or any solvate, or any mixture thereof, which possesses endothelin receptor antagonist activity.

It will further be appreciated that a compound of the formula I may be chemically modified such that in vivo it is converted into a parent compound of the formula I (for example, by hydrolytic, oxidative or enzymatic cleavage). Such chemically modified compounds are commonly referred to as prodrugs and may be, for example, metabolically labile ester or amide derivatives of a parent compound having a carboxylic acid group (or a metabolically labile ester of a parent compound having an hydroxy group). It is to be understood that the present invention also concerns any such prodrugs, including metabolically labile ester or amide derivatives of compounds of the formula I.

It is further to be understood that generic terms such as "alkyl" include both straight and branched chain variants when the carbon numbers permit.

However, when a particular radical such as "propyl" is given, it is specific to the straight chain variant, branched chain variants such as "isopropyl" being specifically named when intended. The same convention applies to other radicals.

It is further to be appreciated that the ring containing $A^1$, $A^2$, $A^3$ and $A^4$ is a pyridyl ring optionally substituted by 1, 2 or 3 substituents $B^1$ as defined herein. In those compounds in which there is more than one substituent $B^1$ present (i.e. when m is 2 or 3), the value for each $B^1$ may be the same or different. Also, when a substituent on Ar is a heterocyclyl group, it is attached to the ring containing $A^1, A^2, A^3$ and $A^4$ by a ring carbon of the heterocyclyl group.

Particular values for a substituent on Ar include, by way of example, for (1–6C)alkyl: (1–4C)alkyl, such as methyl, ethyl, propyl, isopropyl, isobutyl, tert-butyl and sec-butyl;

for amino(1–6C)alkyl: amino(1–4C)alkyl, such as aminomethyl and 2-aminoethyl;

for hydroxy(1–6C)alkyl: hydroxy(1–4C)alkyl, such as hydroxymethyl, 1-hydroxyethyl, 2-hydroxyethyl, 3-hydroxy-2-methylpropyl (alternatively named 2-(hydroxymethyl)propyl) and 1-hydroxy-2-methylpropyl;

for N-[(1–4C)alkyl]amino(1–6C)alkyl: N-[(1–2C)alkylamino(1–4C)alkyl, such as methylaminomethyl and 2-(methylamino)ethyl;

for N,N-[di(1–4C)alkyl]amino(1–6C)alkyl: N,N-[di(1–2C)alkyl]amino-(1–4C)alkyl, such as dimethylaminomethyl and 2-(dimethylamino)ethyl;

for carboxy(1–6C)alkyl: carboxy(1–4C)alkyl, such as carboxymethyl, 1-carboxyethyl, 2-carboxyethyl, 2-carboxypropyl and 2-carboxy-2-methylpropyl;

for (1–6C)alkoxycarbonyl(1–6C)alkyl: (1–4C)alkoxycarbonyl(1–4C)alkyl, such as methoxycarbonylmethyl, ethoxycarbonylmethyl, 1-(methoxycarbonyl)ethyl, 2-(methoxycarbonyl)ethyl, 1-(ethoxycarbonyl)ethyl, 2-(ethoxycarbonyl)ethyl, 2-(methoxycarbonyl)propyl, 2-(ethoxycarbonyl)propyl, 2-methoxycarbonyl-2-methylpropyl and 2-propoxycarbonyl-2-methylpropyl;

for (1–6C)alkylcarbonyloxy(1–6C)alkyl: (1–4C)alkylcarbonyloxy(1–4C)alkyl, such as acetoxymethyl, propylcarbonyloxymethyl, pivaloyloxymethyl, 3-acetoxy-2-methylpropyl and 2-methyl-3-pivaloyloxypropyl;

for carboxy(1–6C)alkoxy: carboxy(1–4C)alkoxy, such as carboxymethoxy, 1-carboxyethoxy, 2-carboxyethoxy and 2-carboxypropoxy;

for carboxy(1–6C)alkylthio: carboxy(1–4C)alkylthio, such as carboxymethylthio, 1-carboxyethylthio; 2-carboxyethylthio and 2-carboxypropylthio;

for (1–6C)alkoxycarbonyl(1–6C)alkoxy: (1–4C)alkoxycarbonyl(1–4C)alkoxy, such as methoxycarbonylmethoxy, ethoxycarbonylmethoxy, 1-(methoxycarbonyl)ethoxy, 1-(ethoxycarbonyl)ethoxy, 2-(methoxycarbonyl)ethoxy, 2-(ethoxycarbonyl)ethoxy, 2-(methoxycarbonyl)propoxy and 2-(ethoxycarbonyl)propoxy;

for (1–6C)alkoxycarbonyl(1–6C)alkylthio: (1–4C) alkoxycarbonyl(1–4C)alkylthio, such as (methoxycarbonyl)methylthio, ethoxycarbonylmethylthio, 1-(methoxycarbonyl)ethylthio, 1-(ethoxycarbonyl)ethylthio, 2-(methoxycarbonyl)ethylthio, 2-(ethoxycarbonyl)ethylthio, 2-(methoxycarbonyl)propylthio, and 2-(ethoxycarbonyl)propylthio;

for (2–6C)alkenyl: (2–4C)alkenyl, such as vinyl, allyl, 1-propenyl and 2-butenyl;

for carbamoyl(1–6C)alkyl: carbamoyl(1–4C)alkyl, such as carbamoylmethyl, 1-carbamoylethyl, 2-carbamoylethyl and 2-carbamoylpropyl;

for (1–6C)alkylcarbamoyl(1–6C)alkyl: (1–4C)alkylcarbamoyl(1–4C)alkyl, such as (N-methylcarbamoyl)methyl, (N-ethylcarbamoyl)methyl, 1-(N-methylcarbamoyl)ethyl, 2-(N-methylcarbamoyl)ethyl, 1-(N-ethylcarbamoyl)ethyl, 2-(N-ethylcarbamoyl)ethyl, 2-(N-methylcarbamoyl)propyl and 2-(N-ethylcarbamoyl)propyl;

for di(1–6C)alkylcarbamoyl(1–6C)alkyl: di(1–4C)alkylcarbamoyl(1–4C)alkyl, such as (N,N-dimethylcarbamoyl)methyl, (N,N-diethylcarbamoyl)methyl, 1-(N,N-dimethylcarbamoyl)ethyl, 2-(N,N-dimethylcarbamoyl)ethyl, 1-(N,N-diethylcarbamoyl)ethyl, 2-(N,N-diethylcarbamoyl)ethyl, 2-(N,N-dimethylcarbamoyl)propyl and 2-(N,N-diethylcarbamoyl)propyl;

for N-(1–6C)alkylcarbamoyloxy(1–6C)alkyl: N-(1–4C)alkylcarbamoyloxy(1–4C)alkyl, such as N-methylcarbamoyloxymethyl, N-ethylcarbamoyloxymethyl, N-propylcarbamoyloxymethyl, N-butylcarbamoyloxymethyl, 2-methyl-N-ethylcarbamoyloxyethyl, 2-methyl-N-propylcarbamoyloxyethyl, 2-methyl-N-butylcarbamoyloxyethyl, 2-methyl-3-(N-propylcarbamoyloxy)propyl and 2-methyl-3-(N-butylcarbamoyloxy)propyl;

for carbamoyl(1–6C)alkoxy: carbamoyl(1–4C)alkoxy, such as carbamoylmethoxy, 1-carbamoylethoxy, 2-carbamoylethoxy and 2-carbamoylpropoxy;

for (1–6C)alkylcarbamoyl(1–6C)alkoxy: (1–4C)carbamoyl(1–4C)alkoxy, such as N-methylcarbamoyl)methoxy, (N-ethylcarbamoyl)methoxy, 1-(N-methylcarbamoyl)ethoxy, 2-(N-methylcarbamoyl)ethoxy, 1-(N-ethylcarbamoyl)ethoxy, 2-(N-ethylcarbamoyl)ethoxy, 2-(N-methylcarbamoyl)propoxy and 2-(N-ethylcarbamoyl)propoxy;

for di(1–6C)alkylcarbamoyl(1–6C)alkoxy: di(1–4C)alkylcarbamoyl(1–4C)alkoxy, such as N,N-dimethylcarbamoyl)methoxy, (N,N-diethylcarbamoyl)methoxy, 1-(N,N-dimethylcarbamoyl)ethoxy, 2-(N,N-dimethylcarbamoyl)ethoxy, 1-(N,N-diethylcarbamoyl)ethoxy, 2-(N,N-diethylcarbamoyl)ethoxy, 2-(N,N-dimethylcarbamoyl)propoxy and 2-(N,N-diethylcarbamoyl)propoxy;

for carbamoyl(1–6C)alkylthio: carbamoyl(1–6C)alkylthio, such as carbamoylmethylthio, 1-carbamoylethylthio, 2-carbamoylethylthio and 2-carbamoylpropylthio;

for (1–6C)alkylcarbamoyl(1–6C)alkylthio: (1–4C)alkylcarbamoyl(1–4C)alkylthio, such as (N-methylcarbamoyl)methylthio, (N-ethylcarbamoyl)methylthio, (N-ethylcarbamoyl)methylthio, 1-(N-methylcarbamoyl)ethylthio, 2-(N-methylcarbamoyl)ethylthio, 1-(N-ethylcarbamoyl)ethylthio, 2-(N-ethylcarbamoyl)ethylthio, 2-(N-methylcarbamoyl)propylthio and 2-(N-ethylcarbamoyl)propylthio;

for di(1–6C)alkylcarbamoyl(1–6C)alkylthio: di(1–4C)alkylcarbamoyl(1–4C)alkylthio, such as (N,N-dimethylcarbamoyl)methylthio, (N,N-diethylcarbamoyl)methylthio, 1-(N,N-dimethylcarbamoyl)ethylthio, 2-(N,N-dimethylcarbamoyl)ethylthio, 1-(N,N-diethylcarbamoyl)ethylthio, 2-(N,N-diethylcarbamoyl)ethylthio, 2-(N,N-dimethylcarbamoyl)propylthio and 2-(N,N-diethylcarbamoyl)propylthio;

for carboxy(2-C)alkenyl: carboxy(2–4C)alkenyl, such as 2-carboxyethenyl, 3-carboxy-1-propenyl and 4-carboxy-2-butenyl;

for carboxy(2–6C)alkynyl: carboxy(2–4C)alkynyl, such as carboxyethynyl, 3-carboxy-1-propynyl and 4-carboxy-2-butynyl;

for (2–6C)alkynyl: (2–4C)alkynyl, such as ethynyl, 1-propynyl, 2-propynyl and 1-butynyl;

for halogeno(2–6C)alkyl: halogeno(2–4C)alkyl, such as 2-chloroethyl, 2-bromoethyl, 2-fluoroethyl, dichloromethyl, difluoromethyl, 2,2,2-trifluoroethyl and pentafluoroethyl;

for (1–6C)alkoxy: (1–4C)alkoxy, such as methoxy, ethoxy, propoxy, isopropoxy and butoxy;

for hydroxy(1–6C)alkoxy: hydroxy(1–4C)alkoxy, such as hydroxymethoxy, 1-hydroxyethoxy, 2-hydroxyethoxy, 2-hydroxy-2-methylpropoxy and 2-hydroxy-1,1-dimethylethoxy;

for di- or tri-halogeno(1–6C)alkoxy: di- or trihalogeno(1–4C)alkoxy, such as difluoromethoxy, trifluoromethoxy, 2,2,2-trifluoroethoxy, 3,3,3-trifluoropropoxy and pentafluoroethoxy;

for di- or trihalogeno(1–3C)alkoxy: difluoromethoxy, trifluoromethoxy and 2,2,2-trifluoroethoxy;

for (2–6C)alkenyloxy(1–6C)alkyl: (2–4C)alkenyloxy(1–4C)alkyl, such as allyloxymethyl, (2-methyl-2-propenyloxy)methyl and (3-methyl-3-butenyloxy)methyl;

for (2–6C)alkenyloxy: (2–4C)alkenyloxy, such as vinyloxy, allyloxy, 1-propenyloxy and 2-butenyloxy;

for (1–4C)alkoxy(1–6C)alkyl: (1–2C)alkoxy(1–4C)alkyl, such as methoxymethyl, ethoxymethyl, 1-methoxyethyl, 2-methoxyethyl, 2-ethoxyethyl and 3-methoxypropyl;

for (1–6C)alkoxycarbonyl(1–6C)alkoxy(1–6C)alkyl: (1–4C)alkoxycarbonyl(1–4C)alkoxy(1–4C)alkyl, such as (1-methoxycarbonyl-1-methyl)ethoxymethyl, (1-ethoxycarbonyl-1-methyl)ethoxymethyl, methoxycarbonylmethoxymethyl, ethoxycarbonylmethoxymethyl, (1-methoxycarbonylethoxy)methyl and (1-ethoxycarbonylethoxy)methyl;

for carboxy(1–6C)alkoxy(1–6C)alkyl: carboxy(1–4C)alkoxy(1–4C)alkyl, such as carboxymethoxymethyl, (1-carboxy-1-methyl)ethoxymethyl and (1-carboxyethoxy)methyl;

for hydroxy(1–6C)alkoxy(1–6C)alkyl: hydroxy(1–4C)alkoxy(1–4C)alkyl, such as (1-methy hydroxyethoxy)methyl, (1,1-dimethyl-2-hydroxyethoxy)methyl and (2-hydroxyethoxy)methyl;

for (1–4C)alkylthio(1–6C)alkyl: (1–2C)alkylthio(1–4C)alkyl, such as methylthiomethyl, 1-methylthioethyl, 2-methylthioethyl, 2-methylthioprop-2-yl, ethylthiomethyl, 1-ethylthioethyl, 2-ethylthioethyl and 2-ethylthioprop-2-yl;

for (1–4C)alkylsulphinyl(1–6C)alkyl: (1–2C)alkylsulphinyl(1–4C)alkyl, such as methylsulphinylmethyl, 1-methylsulphinylethyl, 2-(methylsulphinyl)ethyl, 2-(methylsulphinyl)prop-2-yl, ethylsulphinylmethyl, 1-(ethylsulphinyl)ethyl, 2-(ethylsulphinyl)ethyl and 2-(ethylsulphinyl)prop-2-yl;

for (1–4C)alkylsulphonyl(1–6C)alkyl: (1–2C)alkylsulphonyl(1–4C)alkyl, such as methsulphonylmethyl, 1-(methylsuphonyl)ethyl, 2-(methylsulphonyl)ethyl,2-(methylsulphonyl)prop-2-yl, ethylsulphonylmethyl, 1-(ethylsulphonyl)ethyl, 2-(ethylsulphonyl)ethyl and 2-(ethylsulphonyl)prop-2-yl;

for (1–4C)alkylenedioxy: methylenedioxy, ethylenedioxy and isopropylidenedioxy;

for (3–6C)cycloalkyl: cyclopropyl, cyclobutyl and cyclopentyl;

for (3–8C)cycloalkyl(1–6C)alkyl: (3–5C)cycloalkyl(1–2C)alkyl, such as cyclopropylmethyl, 1-(cyclopropyl)ethyl, 2-(cyclopropyl)ethyl, cyclobutylmethyl and cyclopentylmethyl;

for phenyl(1–6C)alkyl: phenyl(1–4C)alkyl, such as benzyl, 1-phenylethyl and 2-phenylethyl;

for phenyl(1–6C)alkoxy: phenyl(1–4C)alkoxy, such as benzyloxy, 1-phenylethoxy, 2-phenylethoxy, 2-phenylpropoxy and 3-phenylpropoxy;

for phenyl(1–3)alkoxy: benzyloxy, 1-phenylethoxy and 2-phenylethoxy;

for pyridyl(1–6C)alkoxy(1–6C)alkyl: pyridyl(1–4C)alkoxy(1–4C)alkyl, such as pyridylmethoxymethyl, (2-(pyridyl)ethoxy)methyl and 2-(pyridylmethoxy)ethyl;

for halogeno: fluoro, chloro, bromo and iodo;

for (1–6C)alkoxycarbonyl: (1–4C)alkoxycarbonyl, such as methoxycarbonyl, ethoxycarbonyl and propoxycarbonyl;

for (2–6C)alkenyloxycarbonyl: allyloxycarbonyl, 2-methyl-2-propenyloxycarbonyl and 3-methyl-3-butenyloxycarbonyl;

for phenyl(1–6C)alkoxycarbonyl: phenyl(1–4C)alkoxycarbonyl, such as benzyloxycarbonyl, 1-phenylethoxycarbonyl and 2-phenylethoxycarbonyl;

for (1–6C)alkanoyl: (1–4C)alkanoyl, such as formyl, acetyl, propionyl, butyryl and isobutyryl;

for (1–6C)alkylthio: (1–4C)alkylthio, such as methylthio and ethylthio;

for (1–6C)alkylsulphinyl: (1–4C)alkylsulphinyl, such as methylsulphinyl and ethylsulphinyl;

for (1–6C)alkylsulphonyl: (1–4C)alkylsulphonyl, such as methylsulphony] and ethylsulphonyl;

for (1–6C)alkanoylamino: (1–4C)alkanoylamino, such as formamido, acetamido and propionamido;

for N-[(1–4C)alkyl]trifluoroacetamide: N-methyltrifluoroacetamide and N-ethyltrifluoroacetamide;

for N-[(1–4C)alkyl]benzamido: N-methylbenzamido and N-ethylbenzamido;

for (1–4C)alkylcarbamoyl: N-methylcarbamoyl and N-ethylcarbamoyl;

for di(1–4C)alkylcarbamoyl: N,N-dimethylcarbamoyl and N,N-diethylcarbamoyl;

for N-(1–4C)alkylsulphamoyl: N-methylsulphamoyl and N-ethylsulphamoyl;

for N,N-di(1–4C)alkylsulphamoyl: N,N-dimethylsulphamoyl and N,N-diethylsulphamoyl;

for (1–6C)alkanesulphonamido: (1–4C)alkanesulphonamido, such as methanesulphonamido and ethanesulphonamido;

for 3-(1–6C)alkylureido: 3-(1–4C)alkylureido, such as 3-methylureido, 3-ethylureido and 3-propylureido;

for 3-(1–6C)alkylthioureido: 3-(1–4C)alkylthioureido, such as 3-methylthioureido, 3-ethylthioureido and 3-propylthioureido;

for a five membered heterocyclyl group containing 1, 2, 3 or 4 heteroatoms independently selected from nitrogen, oxygen and sulphur: pyrrolyl, furyl, thienyl, imidazolyl, pyrazolyl, oxazolyl, isoxazolyl, thiazolyl, isothiazolyl, 1,2,3-triazolyl, 1,2,4-triazolyl, 1,3,4-triazolyl, 1,2,4-oxadiazolyl, 1,3,4-oxadiazolyl, furazanyl, 1,2,4-thiadiazolyl, 1,3,4-thiadiazolyl and tetrazolyl; and for a six membered heterocyclyl group containing 1, 2 or 3 heteroatoms independently selected from nitrogen, oxygen and sulphur: pyridyl, pyrimidinyl, pyrazinyl, pyridazinyl, triazinyl and pyranyl.

A particular value for Ra and Rb includes, by way of example, for (1–6C)alkyl: (1–4C)alkyl, such as methyl, ethyl, propyl and isopropyl;

for (1–6C)alkyl bearing a carboxy, (1–6C)alkoxycarbonyl, carbamoyl, (1–6C)alkylcarbamoyl or di(1–6C)alkylcarbamoyl group:

(1–4C)alkyl bearing a carboxy, (1–4C)alkoxycarbonyl, carbamoyl, (1–4C)alkylcarbamoyl or di(1–4C)alkylcarbamoyl group, such as carboxymethyl, 1-(carboxy)ethyl, 2-(carboxy)ethyl, 2-(carboxy)propyl, methoxycarbonylmethyl, 1-(methoxycarbonyl)ethyl, 2-(methoxycarbonyl)ethyl, 1-(ethoxycarbonyl)ethyl, 2-(ethoxycarbonyl)ethyl, 2-(methoxycarbonyl)propyl, 2-(ethoxycarbonyl)propyl, carbamoylmethyl, 1-carbamoylethyl, 2-carbamoylethyl, 2-carbamoylpropyl, (N-methylcarbamoyl)methyl, (N-ethylcarbamoyl)methyl, 1-(N-methylcarbamoyl)ethyl, 2-(N-methylcarbamoyl)ethyl, 1-(N-ethylcarbamoyl)ethyl, 2-(N-ethylcarbamoyl)ethyl, 2-(N-methylcarbamoyl)ethyl, 1-(N-ethylcarbamoyl)ethyl, 2-(N-ethylcarbamoyl)ethyl, 2-(N-methylcarbamoyl)propyl, 2-(N-ethylcarbamoyl)propyl, (N,N-dimethylcarbamoyl)methyl, (N,N-diethylcarbamoyl)methyl, 1-(N,N-dimethylcarbamoyl)ethyl, 2-(N,N-dimethylcarbamoyl)ethyl, 1-(N,N-diethylcarbamoyl)ethyl, 2-(N,N-diethylcarbamoyl)ethyl, 2-(N,N-dimethylcarbamoyl)propyl and 2-(N,N-diethylcarbamoyl)propyl; and for phenyl(1–4C)alkyl: benzyl, 1-phenylethyl and 2-phenylethyl.

Particular values for Rx, Ry and Rz include, for example, for halogeno: fluoro, chloro, bromo and iodo; for (1–4C)alkyl: methyl, ethyl and propyl; and for (1–4C)alkoxy: methoxy, ethoxy and propoxy.

Particular values for substituent $R^1$ include, for example, chloro, bromo, iodo, methyl, ethyl, methoxy, ethoxy, trifluoromethyl and ethynyl.

A particular value for $B^1$ or a substituent on a phenyl or benzene or heterocyclyl moiety of a substituent on Ar includes, by way of example, for (1–4C)alkyl: methyl and ethyl;

for (1–4C)alkoxy: methoxy and ethoxy; and for halogeno: fluoro, chloro, bromo and iodo.

Preferred values for $R^1$ include, for example, methyl and halogeno (especially chloro or bromo), methyl being especially preferred.

Preferred values for Rx, Ry and Rz include, for example, methoxy.

A particular group of values for the group Ar includes, for example, unsubstituted phenyl or phenyl bearing 1, 2 or 3 substituents independently selected from (1–6C)alkyl, (1–6C)alkoxy, (1–6C)alkylthio, (1–6C)alkylsulphinyl, (1–6C)alkylsulphonyl, halogeno, amino, N-(1–4C)alkylamino, N,N-di(1–4C)alkylamino, carboxy(1–6C)alkyl, (2–6C)alkenyl, (2–6C)alkynyl, (1–6C)alkoxy(1–6C)alkyl, (1–6C)alkylthio(1–6C)alkyl, (1–6C)alkyl, trifluoromethyl, trifluoromethoxy, carbamoyl, (1–4C)alkylcarbamoyl, di(1–4C)alkylcarbamoyl and (1–6C)alkoxycarbonyl. A particular sub-group of values for the group Ar includes, for example, unsubstituted phenyl or phenyl bearing 1, 2 or 3 substituents independently selected from (1–4C)alkyl, (1–4C)alkoxy, (1–4C)alkylthio, halogeno, amino, N-(1–4C)alkylamino, N,N-di(1–4C)alkylamino, carboxy(1–4C)alkyl, (1–4C)alkoxy(1–4C)alkyl, (1–4C)alkylthio(1–4C)alkyl and (1–4C)alkoxycarbonyl.

A particular sub-group of compounds of the invention includes, for example, compounds in which m is zero, 1 or 2, and more particularly zero or 1. Preferably, m is zero.

A further particular sub-group of compounds of the invention includes, for example, compounds in which the group Ar is unsubstituted phenyl or phenyl bearing one or two substituents independently selected from any of the values defined herein for a substituent on Ar, and more particularly phenyl bearing a para substituent.

A preferred group of compounds of the invention includes, for example, compounds in which the group Ar is phenyl substituted at the para-position by a substituent selected from any of those defined above, and particularly (1–4C)alkyl (especially isobutyl), (1–4C)alkoxy (especially isopropoxy), (1–4C)alkylthio (especially methylthio), N,N-di(1–4C)alkylamino (especially dimethylamino), carboxy(1–4C)alkyl (especially 2-carboxypropyl), carboxy(1–4C)alkoxy (especially 1-carboxyethoxy), halogeno (especially chloro), (2–4C)alkenyl (especially vinyl or allyl), hydroxy(1–4C)alkyl (especially 1-hydroxyethyl, 3-hydroxy-2-methylpropyl or 2-hydroxy-2-methylpropyl), (2–4C)alkanoylamino (especially acetylamino), (2–4C)alkanoyl (especially acetyl), N-(1–4C)alkylamino (especially isopropylamino), (1–4C)alkoxycarbonyl (especially methoxycarbonyl), (1–4C)alkoxy(1–4C)alkyl (especially methoxymethyl or isopropoxymethyl). Within this group, compounds in which m is zero, (i.e. the pyridyl ring is unsubstituted) are particularly preferred, as well as compounds in which the para-substituent is 2-hydroxy-2-methylpropyl and 2-carboxy-2-methylpropyl.

A further preferred group of compounds of the invention includes, for example, compounds in which the group Ar is phenyl substituted at the para-position by a substituent selected from pyridyl (especially 2-pyridyl or 3-pyridyl), pyrimidinyl (especially 2-pyrimidinyl), oxadiazolyl (especially 1,3,4-oxadiazol-2-yl and 1,2,4-oxadiazol-3-yl), 3-methylisoxazol-5-yl, 3-methyl-1,2,4-oxadiazol-5-yl, 5-methyl-1,2,4-oxadiazol-3-yl, pyridyl(1–4C)alkoxy(1–4C)alkyl (especially (3-pyridylmethoxy)methyl), (2–4C)alkenyloxy(1–4C)alkyl, (1–4C)alkoxycarbonyl(1–4C)alkoxy(1–2C)alkyl, carboxy(1–4C)alkoxy(1–2C)alkyl, hydroxy(1–4C)alkoxy(1–2C)alkyl, phenyl(1–4C)alkoxy, carboxy(1–4C)alkyl, carboxy(2–4C)alkenyl, (1–4C)alkoxycarbonyl(1–4C)alkyl, (1–4C)alkylcarbonyloxy(1–4C)alkyl, N-(1–4C)alkylcarbamoyloxy(1–4C)alkyl, (3–6C)cycloalkyl(1–4C)alkyl, carboxy(1–4C)alkoxy and hydroxy(1–4C)alkoxy. Within this group, compounds in which Ar is phenyl substituted by 1,2, 4-oxadiazol-3-yl and 1,3,4-oxadiazol-2-yl and m is zero are particularly preferred.

Further independent sub-groups of compounds of the invention include, for example, compounds of the formula I in which:
(1) $A^1$ is nitrogen and $A^2$, $A^3$, $A^4$ are CH;
(2) $A^2$ is nitrogen and $A^1$, $A^3$ and $A^4$ are CH;
(3) $A^1$ is nitrogen and $A^1$, $A^3$ and $A^4$ are CH; and
(4) $A^4$ is nitrogen and $A^1$, $A^2$ and $A^3$ are CH;
and wherein, within each of sub-groups (1)–(4), $B^1$, m, Ar, W, X, Y, Z and $R^1$ have any of the values (including the particular and preferred values and groups of values) defined herein, and N-oxides thereof, and pharmaceutically acceptable salts thereof. Within these sub-groups, further sub-groups include compounds in which:
(i) the ring containing W, X, Y and Z and bearing $R^1$ is a pyrazine ring bearing Ry and $R^1$ as defined herein; and
(ii) the ring containing W, X, Y and Z and bearing $R^1$ is a pyridazine ring bearing Rx and $R^1$ as defined herein.

Within sub-groups (1), (2), (3) and (4), preferred compounds are those in which the ring containing W, X, Y, Z and bearing substituent $R^1$ is a ring in which W is nitrogen, X is CH; Y is nitrogen; and Z is CRy in which Ry is hydrogen, halogeno, (1–4C)alkyl or (1–4C)alkoxy; and $R^1$ is hydrogen, halogeno, (1–4C)alkyl, methoxy, ethoxy, trifluoromethyl, trifluoromethoxy or ethynyl. An especially preferred group of compounds includes, for example, those compounds in which Ry is methoxy and $R^1$ is methyl or halogeno, especially methyl.

A further preferred group of compounds of the invention includes, for example, compounds of the Formula II in which $B^1$, m, Ar, W, X, Y, Z and $R^1$ have any of the meanings (including the particular and preferred meanings) defined above, or an N-oxide thereof, or a pharmaceutically acceptable salt thereof. Within this group, compounds which are especially preferred include, for example, compounds in which the ring containing W, X, Y, Z and bearing substituent $R^1$ is a ring in which W is nitrogen; X is CH; Y is nitrogen; and Z is CRy in which Ry is hydrogen, halogeno, (1–4C)alkyl, (1–4C)alkoxy or trifluoromethoxy; and $R^1$ is hydrogen, halogeno, (1–4C)alkyl, methoxy, ethoxy, trifluoromethyl or ethynyl. Within this group, especially preferred compounds include, for example, those compounds in which Ry is methoxy and $R^1$ is methyl or halogen (especially methyl), those compounds in which Ar is phenyl bearing a para substituent and those compounds in which m is zero.

An especially preferred group of compounds of the invention includes, for example, compounds of the formula II in which m is zero; Ar is a phenyl group bearing a para substituent selected from (1–6C)alkyl, carboxy(1–6C)alkoxy, (2–6C)alkenyl, hydroxy(1–6C)alkyl, (2–6C)alkanoyl, and a group —NRaRb in which Ra and Rb are independently selected from hydrogen and (1–6C)alkyl; the ring containing W, X, Y and Z and bearing $R^1$ is selected from:
(a) a ring in which W is nitrogen,; X is CH; Y is nitrogen; and Z is CRy in which Ry is methoxy; and
(b) a ring in which W is CRz in which Rz is methoxy; X is nitrogen; Y is nitrogen; and Z is CH;
and the substituent $R^1$ (in both (a) and (b)) is methyl, chloro or bromo. Of these, compounds which are most preferred include, for example, those compounds in which the para substituent on Ar is selected from carboxy(1–4C)alkoxy (such as 1-carboxyethoxy), (1–4C)alkyl (such as methyl, ethyl, propyl, isopropyl, isobutyl or tert-butyl), (1–4C)alkylamino (such as isopropylamino), di(1–4C)alkylamino (such as dimethylamino or diethylamino), (2–4C)alkanoyl (such as acetyl), (2–4C)alkenyl (such as allyl), hydroxy(1–4C)alkyl (such as 3-hydroxy-2-methyl)propyl, 1-hydroxyethyl or 2-hydroxy-2-methylpropyl) and (1–4C)alkoxycarbonyl (such as methoxycarbonyl) and those compounds in which the ring bearing W, X, Y and Z and $R^1$ is as defined under (a).

A further especially preferred group of compounds of the invention includes, for example, compounds of the formula II in which m is zero; Ar is a phenyl group bearing a para-substituent selected from (1–4C)alkyl (such as ethyl or isobutyl), hydroxy(1–4C)alkyl (such as 3-hydroxy-2-methylpropyl, 1-hydroxyethyl or 2-hydroxy-2-methylpropyl), (2–6C)alkenyl (such as allyl), 3-pyridyl, 2-pyrimidinyl, 1,3,4-oxadiazolyl, 1,2,4-oxadiazolyl, hydroxy(1–4)alkoxy(1–2C)alkyl (such as (2-hydroxyethoxy)methyl), hydroxy(1–4C)alkoxy (such as 2-hydroxyethoxy), (1–4C)alkylcarbonyloxy(1–4C)alkyl (such as 3-acetoxy-2-methylpropyl), carboxy(1–4C)alkyl (such as 2-carboxypropyl or (2-carboxy-2-methyl)propyl), (2–4C)alkanoyl (such as isopropanoyl), (3–6C)cycloalkyl (1–2C)alkyl (such as cyclopropylmethyl) and (1–4C) alkoxycarbonyl(1–4C)alkyl (such as (2-propoxycarbonyl-2-methyl)propyl), and the ring bearing W, X, Y and Z and $R^1$ is a ring in which W is nitrogen; X is CH; Y is nitrogen and Z is CRy in which Ry is methoxy, and the substituent $R^1$ is methyl, chloro or bromo (especially methyl).

Compounds of the invention which are of particular interest include, for example, the specific embodiments set out hereinafter in the accompanying Examples. Of these, the compounds of Formula I disclosed in Examples 1, 5, 8, 12, 13, 19, 21, 22, 23, 26, 33, 35, 36, 39, 41, 48, 52, 57, 58, 63, 64, 66, 67 isomer B and 69 are of special interest and these compounds, or a pharmaceutically-acceptable salt thereof, are provided as a further feature of the invention.

Examples of metabolically labile ester derivatives of a carboxy group are esters formed with alcohols such as (1–6C)alkanols, for example methanol, ethanol, propanol and isopropanol; indanol; adamantol; (1–6C)alkanoyloxy (1–4C)alkanols such as pivaloyloxymethyl; glycolamides; (S-methyl-2-oxo-1,3-dioxol-4-yl)methyl alcohol; and (1–4C)alkyloxycarbonyl(1–4)alkanols.

Examples of metabolically labile amide derivatives of a carboxy group include amides formed from ammonia and amines such as (1–4C)alkylamine, for example methylamine, di(1–4C)alkyl amines, (1–4C)alkoxy(1–4C) alkylamines such as methoxyethyl amine, phenyl(1–2C) alkylamines such as benzylamine; and amino acids such as glycine or an ester thereof.

It will be appreciated that where sub-groups of compounds of the invention, or particular or preferred groups of compounds of the invention or specific compounds of the invention are referred to, these groups include prodrugs of said compounds, such as metabolically labile esters or amides.

Suitable pharmaceutically-acceptable salts include, for example, salts with alkali metal (such as sodium, potassium or lithium), alkaline earth metals (such as calcium or magnesium), ammonium salts, and salts with organic bases affording physiologically acceptable cations, such as salts with methylamine, dimethylamine, trimethylamine, piperidine and morpholine. In addition, for those compounds which are sufficiently basic, suitable pharmaceutically-acceptable salts include, pharmaceutically-acceptable acid-addition salts with hydrogen halides, sulphuric acid, phosphoric acid and with organic acids such as citric acid, maleic acid, methanesulphonic acid and p-toluenesulphonic acid. Alternatively, the compounds of Formula I may exist in zwitterionic form.

The compounds of Formula I may be obtained by standard procedures of organic chemistry well known in the art for the production of structurally analogous compounds. Such procedures are provided as a further feature of the invention and include, by way of example, the following procedures in which the generic radicals have any of the values given above, unless stated otherwise.

(a) A compound of the Formula III in which P is a protecting group, is deprotected.

A suitable protecting group P includes, for example, an (1–6C)alkoxycarbonyl group (such as methoxycarbonyl, ethoxycarbonyl or isobutoxycarbonyl), benzyloxycarbonyl (in which the benz ring may be optionally substituted, for example it may bear a halogeno, (1–4C)alkyl or (1–4C) alkoxy substituent), 2-methoxyethoxymethyl and tri(1–4C) alkylsilylethoxymethyl (such as 2-(trimethylsilyl) ethoxymethyl). A protecting group P may be removed from the compound of Formula III by treatment with one or more deprotecting agents. It will be appreciated that the deprotecting agent or agents will depend on the particular value for P. Suitable deprotecting agents and procedures for their use are well known in the art. For example, an alkoxycarbonyl group may be removed under basic conditions, such as sodium hydroxide or alkoxide (e.g. methoxide) in a suitable solvent such as methanol; a 2-methoxyethoxymethyl group may be removed using acidic conditions, such as hydrochloric acid in a suitable solvent such as ethanol; and a tri(1–4C) alkylsilylethoxymethyl group may be removed by using tetrabutylammonium fluoride in tetrahydrofuran, by using trifluoroacetic acid or by using a mixture of hydrochloric acid in a suitable solvent such as ethanol.

A compound of the Formula III may be obtained by coupling a compound of the Formula IV where T is bromo, iodo, trifluoromethanesulphonyloxy or, if $A^1$ or $A^3$ is nitrogen, chloro, with an optionally substituted phenylboronic acid of the formula $Ar.B(OH)_2$ (or an anhydride or ester thereof) in the presence of a suitable base and in the presence of a palladium(0), palladium(II), nickel(0) or nickel(II) catalyst.

Suitable catalysts include, for example,tetrakis (triphenylphosphine)nickel(0), bis(triphenylphosphine) nickel(II)chloride, nickel(II)chloride, bis (triphenylphosphine)palladium(II)chloride, tetrakis (triphenylphosphine)palladium(0) and palladium(II) chloride.

A suitable base for use in the reaction is, for example, an alkali metal alkoxide such as sodium methoxide or sodium ethoxide, an alkali metal hydroxide such as sodium or potassium hydroxide, an alkali metal carbonate such as sodium or potassium carbonate, or an organic base such as tri(1–6C)alkylamine, for example, triethylamine.

The coupling is generally performed in the presence of a suitable solvent of diluent, for example, a hydrocarbon, such as toluene or xylene, an ether, such as dioxan or tetrahydrofuran, an (1–4C)alcohol such as methanol, ethanol or butanol, water, or mixtures thereof (for example, a mixture of toluene, ethanol and water).

The reaction is generally performed at a temperature in the range, for example, 50–150° C., and conveniently at or about the reflux temperature of the solvent or mixture of solvents used.

Alternatively, the coupling of a compound of Formula IV with $Ar.B(OH)_2$ (or an anhydride or ester thereof) may be carried out using a source of fluoride ion under aqueous conditions, for example using potassium fluoride in a mixture of toluene and water under reflux.

Compounds of Formula IV may be obtained, for example, by reacting a sulphonyl halide of the Formula V wherein Hal is a halogeno group (such as chloro, bromo or iodo) with an appropriately protected amine of the Formula VI wherein P is a protecting group, for example under basic conditions using sodium hydride in N,N-dimethylformamide (DMF). Alternatively, a sulphonyl halide of the Formula V may be reacted with an amine of the Formula VII to give a compound of the Formula VIII which is then protected to give a compound of the Formula IV. The protecting group P is chosen so that it allows formation of the compound of formula III under the conditions described. Suitable protecting groups and procedures for use thereof are generally known in the art. The protection of an amine of formula VII or a compound of formula VIII may be carried out using standard procedures of organic chemistry. For example, an amine of the formula VII may be protected with an alkoxycarbonyl group or benzyloxycarbonyl group by reaction with the corresponding alkylchloroformate or benzylchloroformate in the presence of a base, such as a tertiary amine (for example pyridine or triethylamine), and in the presence of a solvent such as dichloromethane. A compound of the formula VIII may be protected on the sulphonamide nitrogen by a 2-methoxyethoxymethyl group or a trialkylsilylethoxymethyl group by reaction with 2-methoxyethoxymethyl chloride or trialkylsilylethoxymethyl chloride respectively, in the presence of a base such as diisopropylethylamine or sodium hydride, and in a suitable solvent such as DMF. Sulphonyl halides of Formula V are known in the art or may be obtained, for example, by analogy therewith, for example by analogy with the procedures described in European Patent applications, publication nos. 558288 and 569193. A convenient method for obtaining sulphonyl halides of Formula V is from the corresponding amine of Formula IX, as illustrated in the Examples hereinafter or by analogy therewith. Amines of the Formula IX are commercially available or are well known in the art, being described in standard works of heterocyclic chemistry, and others may be obtained by analogy therewith using standard procedures of organic chemistry.

It will be appreciated that process (a) may be modified, for example, such that functional group interconversion and deprotection of a protecting group P may be carried out in one step, or stepwise with or with out isolation of the intermediate products, for example as illustrated in Examples 8, 26, 28, 29, 36, 39, 40, 42, 43, 44, 47, 55 and 56.

(b) An amine of the Formula VII (or an alkali metal salt thereof) is reacted with a sulphonyl halide of the Formula XI in which Hal. is a halogeno group (for example chloro, bromo or iodo) or a sulphonate of the Formula XIa in which Re is an electron deficient phenyl group, for example 4-nitrophenyl, in a suitable solvent.

When a compound of Formula XI is used, a convenient solvent includes, for example, pyridine. A catalyst, such as 4-dimethylaminopyridine or 4-pyrrolidinopyridine, may be added to assist the coupling reaction. The reaction is generally carried out at a temperature in the range of, for example, 0° C. to 120° C. and more generally 20° C. to 120° C. Alternatively a solvent such as dichloromethane, chloroform, dimethoxyethane, tetrahydrofuran, dioxan or DMF may be used in the presence of a suitable inorganic base, such as sodium or potassium carbonate (which may be present as an aqueous solution) or an organic base, for example a tertiary amine such as pyridine or triethylamine. When the alkali metal salt of the amine of Formula VII is used, this may be formed in situ, for example with the use of a suitable base such as lithium diisopropylamide at a temperature, for example, of about −60° C., or sodium hydride, for example, at ambient temperature, prior to the addition of the sulphonyl halide. It will be appreciated that the reaction of a sulphonyl halide with an amine to form a sulphonamide (and the type of solvents and conditions used therein) is well-known in the art.

When a compound of the Formula XIa is used, it is preferred to prepare the alkali metal salt of the amine of Formula VII in situ, as mentioned above, using, for example, DMF as solvent, prior to addition of the compound of Formula XIa. The reaction may then conveniently be carried out at or near ambient temperature.

A compound of Formula XIa may be obtained using a similar procedure to that described above for the preparation of a compound of Formula III, but using a compound of Formula X in place of the compound of Formula IV. A compound of Formula X may be obtained by reaction of a sulphonyl halide of Formula V with the appropriate phenol of Formula Re.OH, such as 4-nitrophenol, using conventional procedures, for example, by heating in pyridine or by using DMF as solvent in the presence of a tertiary amine, such as N,N-diisopropylethylamine, at a temperature in the range of, for example, 20–100° C.

Whereafter, a compound of the Formula I may be converted into another compound of Formula I by conventional functional group interconversion, for example as illustrated in Example 22, 33, 34, 37, 38, 45, 46, 57, 59, 60, 65, 68 and 69.

It will be appreciated that, in addition to the protecting group P referred to above, it may be convenient or necessary to protect one or more functional groups with a suitable protecting group prior to carrying out the process of (a) or (b) above, or prior to carrying out a functional group interconversion, followed by removal of the protecting group (for example, as illustrated in Examples 19, 48, 49 and 52). Suitable protecting groups and procedures for their use, together with procedure for removing the protecting group, are well known in the art, for example as described in "Protective Groups in Organic Syntheses" by Theodora Greene (John Wiley and Sons Inc., 1981).

Whereafter, when a pharmaceutically-acceptable salt of a compound of formula I is required, it may be obtained, for example, by reaction with the appropriate base affording a physiologically-acceptable cation, or with the appropriate acid affording a physiologically-acceptable anion, or by any other conventional salt formation procedure.

Additionally, a compound of the formula I may be converted into a prodrug (for example, a metabolically labile ester or amide) by methods well known in the art. For example, a pharmaceutically acceptable metabolically labile ester or amide may be formed respectively by esterifying a compound of the formula I bearing a carboxylic acid (or hydroxy) group or reacting the carboxylic acid group (or a reactive derivative thereof) with the appropriate amine, using conventional techniques.

Further, when an optically active form of a compound of formula I is required, one of the aforesaid processes may be carried out using an optically active starting material. Alternatively, the racemic form of a compound of formula I may be resolved, for example by reaction with a optically active form of a suitable organic base, for example, ephedrine, N,N,N-trimethyl(1-phenylethyl)ammonium hydroxide or 1-phenylethylamine, followed by conventional separation of the diastereoisomeric mixture of salts thus obtained, for example by fractional crystallisation from a suitable solvent, for example a (1–4C)alkanol, whereafter the optically active form of said compound of formula I may be liberated by treatment with acid using a conventional procedure, for example using an aqueous mineral acid such as dilute hydrochloric acid. Alternatively, a racemic compound may be separated into its individual isomers by chromatography using a chiral support, for example as illustrated in Example 67.

Certain of the intermediates defined or exemplified herein are novel, for example compounds of the formula III and IV, and are provided as a further feature of the invention.

As stated above, the compounds of formula I will have beneficial pharmacological effects in warm-blooded animals (including man) in diseases and medical conditions where elevated or abnormal levels of endothelin play a significant causative role. (References to studies supporting the implication of endothelin in various diseases or medical conditions are, for example, disclosed in International Patent Applications, Publication Nos. WO 93/21219 and WO 94/02474.) The compounds of the invention will thus be useful in the treatment of diseases or medical conditions such as hypertension, pulmonary hypertension, congestive heart failure, dyslipidaemia, atherosclerosis, restenosis, acute and chronic renal failure, ischaemic stroke, subarachnoid haemorrhage, intermittent claudication, critical limb ischaemia, asthma, and organ failure after general surgery or translantation. They may also be useful for the treatment of pre-eclampsia, premature labour, myocardial infarction, angina pectoris, dysrrhythmia, cardiogenic and endotoxin shock, diabetes mellitus, Raynaud's disease, scleroderma, Buerger's disease, systemic sclerosis, bronchitis, acute respiratory distress syndrome, liver cirrhosis, osteoporosis, Crohn's disease, ulcerative colitis, irritable bowel syndrome, urinary incontinence, migraine, glaucoma, arthritis and certain cancers.

The endothelin receptor antagonist activity of the compounds of the invention may be assessed using one or more of the following procedures:

Test A: The endothelin receptor antagonist activity of compounds of formula I may be assessed in vitro by their ability to inhibit binding of $[^{125}I]$-Endothelin-1 to its receptors. Human $ET_A$ or $ET_B$ receptors (sub-types of the endothelin receptor) were expressed in Mouse Erythroleukemic Cells (MEL cells) by using standard molecular techniques (for example, as described by Sambrook J., Fritsch E. F. & Maniatis T. (1989) Molecular Cloning: A Laboratory Manual, 2nd Edition, Cold Spring Harbor Press, U.S.A.). cDNA sequences encoding the human $ET_A$ and $ET_B$ receptor (Hosoda K. et al (1991), FEBS Lett., 287, 23–26 and Sakamoto A. et al, (1991), Biochem. Biophys Res. Comm., 178, 656–663) are subcloned into pBluescript vector followed by insertion into the MEL cell expression vector pEV as described by Needham et al (1992), Nuc. Acids Res., 20, 997–1003. The resultant expression vector was transfected into MEL cells by electroporation using procedures described by Shelton et al., (1993), Receptors and Channels, 1, 25–37. MEL cells expressing the recombinant human $ET_A$ or $ET_B$ receptor were grown in Dulbecco's Modified Eagle's Medium (DMEM) with 10% Fetal Calf Serum (FC S), 1% glutamine, 1% penicillin/streptomycin and 2 mg/ml Gibco Geneticin (G-418) sulphate. After 3–6 days induction with 1% N,N-dimethylsuphoxide, the MEL cells were harvested for membrane preparation. Freshly prepared MEL cell pellets ($3 \times 10^9$ cells) were homogenised in 30 ml of buffer containing 50 mM 2-amino-2-(hydroxymethyl)-1,3-propanediol hydrochloride (Tris HCl), 0.19M sucrose, 5 µg/ml soybean trypsin inhibitor, 100 µg/ml bacitracin, 1 mM benzamidine and 1 mM phenanthroline pH 7.4 at 5° C. Unbroken cells and nuclei were sedimented by centrifuging the homogenate at 1500×g for 15 minutes at 5° C. The membrane pellet was resuspended in buffer and stored in liquid nitrogen until use.

$[^{125}I]$-Endothelin-1 binding to MEL cell membranes was measured in incubation buffer containing 50 mM Tris HCl, 1 mM $CaCl_2$, 0.05% polyoxyethylenesorbitan monolaurate, 0.1% Bovine Serum Albumin (BSA), 0.02% sodium azide pH 7.4 at 30° C. after 180 minutes incubation. Membrane suspension (equivalent to 1.5 µg and 0.5 kg protein/tube $ET_A$ and $ET_B$ receptor respectively) was added to the incubation containing test compound and 30 pM$[^{125}I]$-Endothelin-1 in a total volume of 225 µl. Nonspecific binding was measured in the presence of 100 nM unlabelled Endothelin-1. The incubation was terminated by harvesting the incubation with 50 mM Tris pH 7.4 through a GF/B filter on a Brandel cell harvestor. The filter discs were punched out and counted in a gamma counter. Compounds are tested in triplicate over a range of concentrations and $IC_{50}$ (or $pIC_{50}$) values calculated.

In general, compounds of formula I as defined above show inhibition in Test A with a $pIC_{50}$ of 6 or more.

Test B: The endothelin receptor antagonist activity of compounds of formula I may be assessed in vitro in isolated tissues by their ability to inhibit the relaxant response to endothelin-1 in the guinea-pig isolated *Taenia coli*. Guinea pigs of either sex and weight >250 g are killed by cervical dislocation and the caecum removed and placed in cold oxygenated Krebs solution. Strips of *Taenia coli* are dissected out and approximately 4 cm lengths set up for isotonic recording in a 20 ml organ bath containing oxygenated Krebs solution at 32° C. After a 90–120 minute equilibration period to allow the tissue to spontaneously develop an increased tone, a cumulative concentration-response curve (relaxation) is constructed to endothelin-1 (0.3–10 nM). The tissue is then washed for a period of at least 90 minutes before construction of a second concentration-response curve to endothelin-1 in the presence of the test compound. The test compound is added to the organ bath (at an initial concentration of 20 µM) at least 30 minutes before constructing the second concentration-response curve to endothelin-1. The endothelin-1 concentration ratio for each experiment is determined by comparing the most parallel portions of the control and drug treated concentration-response curves. From this a $pA_2$ is calculated: $pA_2 = -\log[\text{molar drug concentration}] + \log[\text{concentration ratio} - 1]$.

Test C: This in vivo test involves the measurement of the antagonist effect of the test compound against the pressor response induced by intravenously-administered proendothelin-1 in a pithed rat preparation.

Male rats (280–330 g) are anaesthetised with halothane and artifically respired through a tracheal cannula. Rats are pithed by passing a 2 mm diameter needle through the orbit, through the foramen magnum, and down into the spinal canal. The left femoral vein and the right carotid artery are isolated and catheters filled with heparinised saline are implanted for administration of compounds and measurement of blood pressure respectively. Body temperature is maintained at 38° C. (as measured rectally) by a heated pad. Rats with an initial baseline mean arterial pressure of less than 55 mmHg or greater than 70 mmHg are excluded. Blood pressure is allowed to stabilize for approximately 10 minutes before a baseline reading is taken. Two initial challenges of proendothelin-1 (0.3 and 1.0 nmol $kg^{-1}$) are administered intravenously in a cumulative fashion and pressor responses recorded. Thereafter, a 55 minute recovery period is allowed and rats in which the blood pressure fails to return to within 20% of the baseline are excluded. Test compound is dosed intravenously at a dose volume of 1.0 ml $kg^{-1}$ body weight and further challenges of proendothelin-1 are administered 5 minutes later. Proendothelin-1 is administered cumulatively in increasing doses (starting at 0.3 $nmolkg^{-1}$) until pressor responses are observed. Endothelin receptor antagonism is quantified by calculating dose ratio shifts at the 30 mmHg change level.

Test D: This in vivo test involves the measurement of the antagonist effect of the test compound against the pressor response induced by intravenously-administered proendothelin-1 in a conscious rat preparation.

Male rats (260–290 g) are anaesthetised with Saffan administered via the tail vein. The right jugular vein and carotid artery are isolated and catheters filled with heparin implanted. These are exteriorised at the back of the neck using a metal trochar and the neck incision closed with autoclips. Rats are housed individually with free access to food and water during the recovery phase. Later in the day, food is removed and the rats are fasted overnight with free access to water. The following day the rats are placed in perspex restraining tubes and the arterial catheter drained and connected to a pressure transducer for measurement of mean arterial pressure. Following a ten minute stabilization period, proendothelin-1 (usually 0.3–1.0 nmol $kg^{-1}$) is administered cumulatively until a pressor response of 30 mmHg is achieved. The animals are then returned to their cages and allowed to recover for 2 hours. The test compound is administered orally (by gavage) at a known time point during the recovery period. The dose response curve to proendothelin-1 is then repeated at a fixed time after the oral dose (usually 0.5 or 1.0 hours) and again at a further time point (3 or 5 hours). Endothelin receptor antagonism is quantified by calculating dose ratio shifts at the 30 mmHg change level.

By way of illustration of the endothelin antagonist properties of compounds of the formula I, the compound of Example 3 showed a $pIC_{50}$ value of 8.6 in Test A and, when dosed orally to rats at 3 mg/kg, using the protocol of Test D, produced a mean dose ratio shift=2.93(n=5) on the pressor response to proendothelin-1, as determined one hour after administration of the test compound.

The compounds of formula I will generally be administered for therapeutic or prophylactic purposes to warm-blooded animals (including man) requiring such treatment in the form of a pharmaceutical composition, as is well known in the pharmaceutical art. According to a further feature of the invention there is provided a pharmaceutical composition comprising a compound of formula I, or a pharmaceutically acceptable salt thereof as defined above, together with a pharmaceutically acceptable diluent or carrier. Such compositions will conveniently be in a form suitable for oral administration (e.g. as a tablet, capsule, solution, suspension or emulsion) or parenteral administration (e.g. as an injectable aqueous or oily solution, or injectable emulsion).

The compounds of formula I, or a pharmaceutically acceptable salt thereof, may also be advantageously administered for therapeutic or prophylactic purposes together with another pharmacological agent known in the general art to be of value in treating one or more of the diseases or medical conditions referred to hereinabove, such as beta-adrenergic blocker (for example atenolol), a calcium channel blocker (for example nifedipine), an angiotensin converting enzyme (ACE) inhibitor (for example lisinopril), a diuretic (for example furosemide or hydrochlorothiazide), an endothelin converting enzyme (ECE) inhibitor (for example phosphoramidon), a neutral endopeptidase (NEP) inhibitor, an HMGCoA reductase inhibitor, a nitric oxide donor, an anti-oxidant, a vasodilator, a dopamine agonist, a neuroprotective agent, a steroid, a beta-agonist, an anti-coagulant, or a thrombolytic agent. It is to be understood that such combination therapy constitutes a further aspect of the invention.

In general a compound of formula I (or a pharmaceutically acceptable salt thereof as appropriate) will be administered to man so that, for example, a daily oral dose of up to 50 mg/kg body weight (and preferably of up to 10 mg/kg) or a daily parenteral dose of up to 5 mg/kg body weight (and preferably of up to 1 mg/kg) is received, given in divided doses as necessary, the precise amount of compound (or salt) administered and the route and form of administration depending on size, age and sex of the person being treated and on the particular disease or medical condition being treated according to principles well known in the medical arts.

In addition to their aforesaid use in therapeutic medicine in humans, the compounds of formula I are also useful in the veterinary treatment of similar conditions affecting commercially valuable warm-blooded animals, such as dogs, cats, horses and cattle. In general for such treatment, the compounds of the formula I will be administered in an analogous amount and manner to those described above for administration to humans. The compounds of formula I are also of value as pharmacological tools in the development and standardisation of test systems for the evaluation of the effects of endothelin in laboratory animals such as cats, dogs, rabbits, monkeys, rats and mice, as part of the continuing search for new and improved therapeutic agents.

The invention will now be illustrated by the following non-limiting Examples in which, unless otherwise stated:
(i) concentrations and evaporations were carried out by rotary evaporation in vacuo;
(ii) operations were carried out at room temperature, that is in the range 18–26° C.;
(iii) chromatography and flash column chromatography was performed on Merck Kieselgel 60 (Art. no. 9385) and thin layer chromatography (TLC) was performed on 0.2 mm thickness plates of Kieselgel 60 (Art. no. 5717) obtained from E Merck, Darmstadt, Germany;
(iv) where a silica gel Mega Bond Elut column is referred to, this means (unless otherwise stated) a column containing 10 g of silica of 40 micron particle size, the silica being contained in a 60 ml disposable syringe and supported by a porous disc, obtained from Varian, Harbor City, Calif., U.S.A. under the name "Mega Bond Elut SI";
(v) yields, where given, are intended for the assistance of the reader only and are not necessarily the maximum attainable by diligent process development; and
(vi) $^1H$ NMR spectra were normally determined at 250 MHz in $d_6$-dimethylsulphoxide ($d_6$-DMSO) or $CDCl_3$ using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d, doublet; dd, doublet of doublets.

EXAMPLE 1

1M sodium hydroxide solution (11.2 ml) was added to a solution of N-(isobutoxycarbonyl)-2-(4-isobutylphenyl)-N-(3-methoxy-5-methylpyrazin-2-yl)pyridine-3-sulphonamide (2.6 g) in methanol (50 ml) and the mixture was stirred and heated under reflux for 30 minutes. Water (100 ml) was added and the mixture was acidified to pH 3 with 2M hydrochloric acid. This mixture was extracted with ethyl acetate (5×30 ml) and the extracts were washed with water (30 ml) and saturated sodium chloride solution and dried ($MgSO_4$). Volatile material was removed by evaporation and the residue was purified by gradient elution with 0–15% ethyl acetate/hexane through a silica gel Mega Bond Elut column followed by trituration with ether to give 2-(4-isobutylphenyl)-N-(3-methoxy-5-methylpyrazin-2-yl) pyridine-3-sulphonamide (720 mg) as a solid, m.p. 128–129° C.; $^1H$ NMR ($CDCl_3$): 0.95 (d, 6H), 1.9 (m, 1H), 2.3 (s, 3H), 2.55 (d, 2H), 3.8 (s, 3H), 6.6 (s, 1H), 7.1–7.3 (m, 4H), 7.35 (s, 1H), 7.5 (dd, 1H), 8.7 (dd, 1H), 8.8 (dd, 1H); mass spectrum (positive electrospray (+ve ESP)): 413 $(M+H)^+$.

The starting material N-(isobutoxycarbonyl)-2-(4-isobutylphenyl)-N-(3-methoxy-5-methylpyrazin-2-yl)pyridine-3-sulphonamide was obtained as follows:

(i) A solution of sodium nitrite (6.5 g) in water (15 ml) was added gradually to a solution of 3-amino-2-chloropyridine (10 g) in acetic acid (100 ml) and concentrated hydrochloric acid (37 ml) at 0–5° C. This cold solution was then added portion-wise to a stirred and cooled (5° C.) mixture of copper(I) chloride (2.33 g) in acetic acid (160 ml) saturated with sulphur dioxide keeping the temperature below 10° C. After the addition was complete the cooling bath was removed and the mixture was stirred a further 90 minutes at ambient temperature. Volatile material was removed by evaporation and water (300 ml) was added to the residue to give a solid. The water was decanted off and the solid was dissolved in ether (500 ml) and washed with saturated aqueous sodium hydrogen carbonate solution (200 ml), water (200 ml) and saturated sodium chloride solution and was then dried ($MgSO_4$). Volatile material was removed by evaporation to give 2-chloropyridine-3-sulphonyl chloride (12.1 g) as an oil which solidified upon refrigeration and was used without further purification; $^1$H NMR ($CDCl_3$): 7.5 (dd, 1H), 8.5 (dd, 1H), 8.7 (dd, 1H).

(ii) Sodium hydride (60% dispersion in oil; 0.083 g) was added to a stirred solution of isobutyl N-(3-methoxy-5-methylpyrazin-2-yl)-carbamate (0.451 g) in dry N,N-dimethylformamide (DMF; 8 ml) at 4° C. The mixture was stirred whilst warming to ambient temperature over 1 hour, was recooled to 4° C. and 2-chloropyridine-3-sulphonyl chloride (0.40 g) was added in portions over 2 minutes. The mixture was allowed to warm to ambient temperature and stirred a further 30 minutes. Water (40 ml) was added, followed by 1M hydrochloric acid to acidify. This mixture was extracted with ethyl acetate (4×15 ml) and the organic extracts were washed with water (10 ml) and saturated sodium chloride solution (10 ml) and then dried ($MgSO_4$). Volatile material was removed by evaporation and the residue was purified by gradient elution with 0–35% ethyl acetate/hexane through a silica gel Mega Bond Elut column and triturated with ether to give 2-chloro-N-isobutoxycarbonyl-N-(3-methoxy-5-methylpyrazin-2-yl)-pyridine-3-sulphonamide (0.34 g) as a solid, m.p. 99–101° C.; $^1$H NMR ($CDCl_3$): 0.7 (d, 6H), 1.7 (m, 1H), 2.5 (s, 3H), 3.8 (d, 2H), 4.0 (s, 3H), 7.45 (dd, 1H), 7.9 (s, 1H), 8.6 (dd, 1H), 8.7 (dd, 1H); mass spectrum (+ve ESP): 415 $(M+H)^+$.

(iii) A solution of 2-chloro-N-isobutoxycarbonyl-N-(3-methoxy-5-methylpyrazin-2-yl)pyridine-3-sulphonamide (4.0 g), 4-isobutylphenylboronic acid (obtained as described in European Patent Application, publication No. 0569193) (1.72 g) and tetrakis(triphenylphosphine)palladium(0) (0.334 g) in toluene (80 ml) and ethanol (40 ml) was deoxygenated by evacuation and refilling with argon (4 cycles). 2M Sodium carbonate solution (25 ml) was then added. The mixture was stirred and heated under reflux for 16 hours. Water (100 ml) was added and the mixture was extracted with ethyl acetate (4×40 ml). The organic extracts were washed with water (50 ml) and saturated sodium chloride solution (50 ml) then dried ($MgSO_4$). Volatile material was removed by evaporation and the residue was purified by gradient elution with 0–20% ethyl acetate/hexane through a 20 g silica gel Mega Bond Elut column to give N-(isobutoxycarbonyl)-2-(4-isobutylphenyl)-N-(3-methoxy-5-methylpyrazin-2-yl)pyridine-3-sulphonamide (3.1 g) as a solid, m.p. 133–137° C.; $^1$H NMR ($CDCl_3$): 0.7 (d, 6H), 0.9 (d, 6H), 1.7 (m, 1H), 1.9 (m, 1H), 2.5 (m, 5H), 3.9 (d, 2H), 4.0 (s, 3H), 7.2 (d, 2H), 7.5 (m, 3H), 8.85 (dd, 1H), 8.9 (s, 1H); mass spectrum (+ve ESP): 513 $(M+H)^+$.

The isobutyl N-(3-methoxy-5-methylpyrazin-2-yl) carbamate used in step (ii) was obtained as follows:

(a) A solution of bromine (0.11 ml) in chloroform (20 ml) was added dropwise over 20 minutes to a solution of 2-amino-5-methylpyrazine (0.218 g) in chloroform (30 ml) which was protected from light. The reaction mixture was stirred for 90 minutes after addition was complete and was then washed with water (50 ml). The organic phase was dried ($MgSO_4$) and volatile material was removed by evaporation to give a yellow oil. The oil was purified by elution with dichloromethane through a silica gel Mega Bond Elut column to give 2-amino-3-bromo-5-methylpyrazine (0.286 g) as a white solid, m.p. 51–52° C.; mass spectrum (+ve CI): 188 $(M+H)^+$.

(b) 2-Amino-3-bromo-5-methylpyrazine (0.374 g) was added to a freshly prepared solution of sodium methoxide in methanol (made by addition of sodium (0.115 g) to methanol (6 ml)). The reaction was heated under reflux for 18 hours, cooled to ambient temperature and the solvent removed by evaporation. Water (5 ml) was added to the residue and extracted with dichloromethane (3×20 ml). The combined organic extracts were dried ($MgSO_4$) and the solvent removed by evaporation. The residue was purified by chromatography on silica gel, eluting with dichloromethane to give 2-amino-3-methoxy-5-methylpyrazine as a white crystalline solid (0.208 g, 75%), m.p. 67–69° C.; mass spectrum (+ve CI): 140 $(M+H)^+$.

c) Isobutylchloroformate (4.79 ml) was added to a stirred solution of 2-amino-3-methoxy-5-methylpyrazine (5 g) and pyridine (2.91 ml) in dichloromethane (10 ml) at ambient temperature. After 90 minutes the reaction mixture was diluted with dichloromethane (10 ml) and washed with 2M hydrochloric acid (3×20 ml), water (20 ml) and saturated sodium chloride solution (20 ml) and then dried ($MgSO_4$). Volatile material was removed by evaporation to give a solid which was recrystallised from hexane to give isobutyl N-(3-methoxy-5-methylpyrazin-2-yl)carbamate (6.5 g); $^1$H NMR ($CDCl_3$): 1.0 (d, 6H), 2.0 (m, 1H), 2.4 (s, 3H), 4.0 (d, 2H), 4.02 (s, 3H), 7.3 (s, 1H), 7.8 (s, 1H); mass spectrum (postive chemical ionisation (+ve CI)): 240 $(M+H)^+$.

EXAMPLES 2–3

Using an analogous procedure to that described in Example 1, the following compounds of formula I were obtained in yields of 10–37%:

EXAMPLE 2

N-(3-methoxy-5-methylpyrazin-2-yl)-2-phenylpyridine-3-sulphonamide $^1$H NMR ($d_6$-DMSO): 2.2 (s, 3H), 3.6 (s, 3H), 7.3–7.55 (m, 6H), 7.6 (dd, 1H), 8.4 (dd, 1H), 8.8 (dd, 1H), 10.5 (br s, 1H); mass spectrum (positive fast atom bombardment (+ve FAB), methanol/m-nitrobenzyl alcohol (NBA)): 357 $(M+H)^+$; starting from N-(isobutoxycarbonyl)-N-(3-methoxy-5-methylpyrazin-2-yl)-2-phenylpyridine-3-sulphonamide; 1H NMR ($d_6$-DMSO): 0.6 (d, 6H), 1.7 (m, 1H), 2.55 (s, 3H), 3.7 (d, 2H), 3.9 (s, 3H), 7.4–7.55 (m, 5H), 7.8 (dd, 1H), 8.9 (dd, 1H), 8.95 (dd, 1H); mass spectrum (+ve CI): 457 $(M+H)^+$; itself obtained using an analogous procedure to that described in Example 1, part (iii) but using phenylboronic acid.

EXAMPLE 3

2-(4-isopropoxyphenyl)-N-(3-methoxy-5-methylpyrazin-2-yl)pyridine-3-sulphonamide $^1$H NMR (CDCl$_3$): 1.40 (d, 6H), 2.3 (s, 3H), 3.8 (s, 3H), 4.6 (m, 1H), 6.7 (br s, 1H), 6.9 (d, 2H), 7.2–7.35 (m, 3H), 7.5 (dd, 1H), 8.7 (dd, 1H), 8.8 (dd, 1H); mass spectrum (+ve ESP): 415 (M+H)$^+$; starting from N-isobutoxycarbonyl-2-(4-isopropoxyphenyl)-N-(3-methoxy-5-methylpyrazin-2-yl) pyridine-3-sulphonamide; $^1$H NMR (CDCl$_3$): 0.7 (d, 6H), 1.40 (d, 6H), 1.7 (m, 1H), 2.5 (s, 3H), 3.8 (d, 3H), 4.0 (s, 3H), 4.6 (m, 1H), 6.9 (d, 2H), 7.45 (dd, 1H), 7.6 (d, 2H), 7.9 (s, 1H), 8.8 (dd, 1H), 8.95 (dd, 1H); mass spectrum (+ve ESP): 515 (M+H)$^+$; itself obtained using an analogous procedure to that described in Example 1, part (iii) but with the addition of potassium iodide (1 molar equivalent) and using 4-isopropoxyphenylboronic acid which was prepared as described in European Patent Application, publication no. 569193.

EXAMPLE 4

Tetrabutylammonium fluoride (0.7 ml of a 1.1M solution in THF) was added to a solution of N-(3-methoxy-5-methylpyrazin-2-yl)-2-(4-methylthiophenyl)-N-[2-(trimethylsilyl)ethoxymethyl]pyridine-3-sulphonamide (0.373 g) in dry THF (4 ml) and the solution was heated to 60° C. for 3 hours. More tetrabutylammonium fluoride solution (0.35 ml) was added and heating was continued for 5 hours. Further aliquots of tetrabutylammonium fluoride solution (a further 2.5 ml in total) were added until reaction was complete as judged by thin layer chromatography (eluting with ethyl acetate/hexane (1:1 v/v)). Volatile material was removed by evaporation and the residue was diluted with water and extracted three times with ethyl acetate. The organic extracts were washed with water and saturated sodium chloride solution and then dried (MgSO$_4$). Volatile material was removed by evaporation and the residue was purified by gradient elution with 0–40% ethyl acetate/hexane through a silica gel Mega Bond Elut column to give N-(3-methoxy-5-methylpyrazin-2-yl)-2-(4-methylthiophenyl)pyridine-3-sulphonamide (0.201 g) as a foam; $^1$H NMR (CDCl$_3$): 2.3 (s, 3H), 2.5 (s, 3H), 3.8 (s, 3H), 7.15–7.35 (m, 4H), 7.5 (m, 1H), 8.7 (dd, 1H), 8.8 (dd, 1H); mass spectrum (+ve ESP): 403 (M+H)$^+$.

The starting material N-(3-methoxy-5-methylpyrazin-2-yl)-2-(4-methylthiophenyl)-N-[2-(trimethylsilyl)ethoxymethyl]pyridine-3-sulphonamide was obtained as follows:

(i) 4-Dimethylaminopyridine (0.1 g) was added to a solution of 2-chloropyridine-3-sulphonyl chloride (1.06 g), 2-amino-3-methoxy-5-methylpyrazine (0.695 g) and pyridine (0.424 ml) in dichloromethane (5 ml) and the mixture was stirred at ambient temperature for 18 hours. The solution was then transferred to a silica gel Mega Bond Elut column. Elution with 0–40% ethyl acetate/hexane gave 2-chloro-N-(3-methoxy-5-methylpyrazin-2-yl)pyridine-3-sulphonamide (0.47 g) as an oil; $^1$H NMR (d$_6$-DMSO): 2.3 (s, 3H), 3.9 (s, 3H), 7.5 (s, 1H), 7.65 (dd, 1H), 8.45 (dd, 1H), 8.7 (dd, 1H); mass spectrum (+ve CI): 315 (M+H)$^+$.

(ii) 2-(Trimethylsilyl)ethoxymethyl chloride (0.315 ml) was added dropwise to a stirred solution of 2-chloro-N-(3-methoxy-5-methylpyrazin-2-yl)pyridine-3-sulphonamide (0.47 g) and N,N-diisopropylethylamine (0.347 ml) in dry DMF (7 ml) at −15° C. Stirring was continued for 40 minutes at this temperature after the addition was complete. Ethyl acetate (40 ml) was added and the mixture was washed with water (3×15 ml) and saturated sodium chloride solution and then dried (MgSO$_4$). Volatile material was removed by evaporation and the residue was purified by gradient elution with 0–30% ethyl acetate/hexane through a silica gel Mega Bond Elut column to give 2-chloro-N-(3-methoxy-5-methylpyrazin-2-yl)-N-[2-(trimethylsilyl)ethoxymethyl]pyridine-3-sulphonamide (0.462 g) as an oil; $^1$H NMR (CDCl$_3$): 0.0 (s, 9H), 0.85 (t, 2H), 2.5 (s, 3H), 3.75 (t, 2H), 3.8 (s, 3H), 5.3 (s, 2H), 7.3 (dd, 1H), 7.8 (s, 1H), 8.4 (dd, 1H), 8.5 (dd, 1H); mass spectrum (+ve ESP): 403 (M+H)$^+$.

(iii) Tetrakis(triphenylphosphine)palladium(0) (0.022 g) was added to a deoxygenated mixture of 2-chloro-N-(3-methoxy-5-methylpyrazin-2-yl)-N-[2-(trimethylsilyl)ethoxymethyl]pyridine-3-sulphonamide (0.405 g), 4-methylthiophenylboronic acid (obtained by the procedure described in *Tetrahedron Lett.*, 1993, 34, 8237) (0.148 g), toluene (4.5 ml), ethanol (2.5 ml) and 2M sodium carbonate solution (7 ml) and the mixture was stirred and heated under reflux for 18 hours. Water was added and the mixture was extracted three times with ethyl acetate. The organic extracts were combined, washed with saturated sodium chloride solution and then dried (MgSO$_4$). Volatile material was removed by evaporation and the residue was purified by gradient elution with 0–35% ethyl acetate/hexane through a silica gel Mega Bond Elut column to give N-(3-methoxy-5-methylpyrazin-2-yl)-2-(4-methylthiophenyl)-N-[2-(trimethylsilyl)ethoxymethyl]pyridine-3-sulphonamide (0.415 g) as an oil; $^1$H NMR (CDCl$_3$): 0.0 (s, 9H), 0.8 (t, 2H), 2.5 (s, 3H), 2.55 (s, 3H), 3.6 (t, 2H), 3.9 (s, 3H), 4.8 (s, 2H), 7.3–7.5 (m, 3H), 7.6–7.7 (m, 2H), 7.8 (s, 1H), 8.7 (dd, 1H), 8.8 (dd, 1H); mass spectrum (+ve ESP): 533 (M+H)$^+$.

EXAMPLE 5

Sodium hydride (60% dispersion in oil; 0.098 g) was washed with hexane (2×3 ml) under an atmosphere of argon. Dry DMF (1.5 ml) was added with stirring. The resultant suspension was cooled to 5° C. and a solution of 2-amino-5-chloro-3-methoxypyrazine (0.178 g) in dry DMF (3 ml) was added. After effervescence had ceased a solution of 4-nitrophenyl 2-(4-isobutylphenyl)pyridine-3-sulphonate (0.459 g) in dry DMF (3 ml) was added dropwise over 5 minutes. The cooling bath was removed and the reaction mixture was stirred for 40 minutes then poured into 2M hydrochloric acid (100 ml) and the product was extracted into ethyl acetate (2×200 ml). The extracts were washed with water (2×100 ml) and saturated sodium chloride solution, then combined and dried (MgSO$_4$). Volatile material was removed by evaporation and the residue was purified by elution with methanol/dichloromethane (1:99 v/v) through a 20 g silica gel Mega Bond Elut column to give N-(5-chloro-3-methoxypyrazin-2-yl)-2-(4-isobutylphenyl)pyridine-3-sulphonamide (0.339 g) as a solid, m.p. 156–157° C., $^1$H NMR (d$_6$-DMSO): 0.9 (d, 6H), 1.9 (m, 1H), 2.55 (d, 2H), 3.85 (s, 3H), 7.1 (d, 2H), 7.3 (d, 2H), 7.6 (dd, 1H), 7.7 (s, 1H), 8.4 (dd, 1H), 8.8 (dd, 1H), 10.9 (br s, 1H); mass spectrum (+ve ESP): 433 (M+H)$^+$.

The starting material 4-nitrophenyl 2-(4-isobutylphenyl)pyridine-3-sulphonate was obtained as follows:

(i) N,N-Diisopropylethylamine (0.45 ml) was added to a solution of 2-chloropyridine-3-sulphonyl chloride (0.53 g) and 4-nitrophenol (0.35 g) in DMF (5 ml). The mixture was stirred at ambient temperature for 30 minutes then diluted with ethyl acetate (25 ml) and washed with water (2×25 ml), saturated sodium carbonate solution (3×20 ml), water (20 ml) and saturated sodium chloride solution. Aqueous layers were back-extracted with ethyl acetate (25 ml) and the organic layers were combined and dried (MgSO$_4$). Volatile material was removed by evaporation to give 4-nitrophenyl 2-chloropyridine-3-sulphonate (0.52 g) as a solid, m.p. 127–128° C.; $^1$H NMR (d$_6$-DMSO): 7.5 (d, 2H), 7.7 (dd, 1H), 8.3 (d, 2H), 8.4 (dd, 1H), 8.8 (dd, 1H); mass spectrum (+ve FAB, NBA/DMSO): 315 (M+H)$^+$.

(ii) Tetrakis(triphenylphosphine)palladium(0) (0.076 g) was added to a deoxygenated mixture of 4-nitrophenyl 2-chloropyridine-3-sulphonate (0.69 g), 4-isobutylphenylboronic acid (0.47 g), potassium fluoride (0.38 g), toluene (15 ml) and water (2.5 ml) and the mixture was stirred and heated under reflux for 24 hours. Water (50 ml) was added and the mixture was extracted with ethyl acetate (2×80 ml). The organic extracts were washed with saturated sodium chloride solution and then combined and dried (MgSO$_4$). Volatile material was removed by evaporation and the residue was purified by gradient elution with dichloromethane/hexane (1:1–1:0 v/v) then dichloromethane/hexane/ethyl acetate (10:9:1 v/v) through a silica gel Mega Bond Elut column followed by recrystallisation from ethyl acetate/hexane to give 4-nitrophenyl 2-(4-isobutylphenyl)pyridine-3-sulphonate (0.50 g), m.p. 123–124° C.; $^1$H NMR (d$_6$-DMSO): 0.9 (d, 6H), 1.9 (m, 1H), 2.55 (d, 2H), 7.2–7.3 (m, 4H), 7.5 (d, 2H), 7.7 (dd, 1H), 8.2 (d, 2H), 8.4 (dd, 1H), 9.0 (dd, 1H); mass spectrum (+ve FAB, NBA/DMSO): 413 (M+H)$^+$.

The starting material 2-amino-5-chloro-3-methoxypyrazine was obtained as follows:

(a) Methyl 2-aminopyrazine-3-carboxylate (5.4 g) was suspended in acetic acid (40 ml) and water (140 ml) was added. The mixture was warmed to 40° C. and chlorine gas was bubbled through it. The resulting clear solution was then cooled to 0° C. and chlorine addition continued for 20 minutes, at which time the weight of the reaction mixture had increased by 4.8 g. The precipitate which had formed was collected by filtration and chlorine was bubbled through the filtrate for a further 10 minutes, whereby the weight of the filtrate increased by a further 2.2 g. A second precipitate was collected by filtration and the combined solids were stirred with a solution of sodium bisulphite (9 g) in water (60 ml) for 1.5 hours. The solid was collected by filtration and washed with ice/water (2×100 ml) and dried under vacuum to give methyl 2-amino-5-chloropyrazine-3-carboxylate (4.3 g); $^1$H NMR (d$_6$-DMSO): 3.87 (s, 3H), 7.5 (br s, 2H), 8.37 (s, 1H); mass spectrum (+ve CI): 188 (M+H)$^+$.

(b) Methyl 2-amino-5-chloropyrazine-3-carboxylate (3.75 g) was added to a solution of sodium hydroxide (2.0 g) in water (20 ml) and the solution was heated under reflux for 1.5 hours. The reaction mixture was cooled to 0° C. and the precipitate which had formed was collected by filtration. The solid was redissolved in water (60 ml) with heating and the solution was filtered. The filtrate was then acidified to pH 2 with 2M hydrochloric acid. The precipitate which formed was collected by filtration and washed with ice/water (2×20 ml) and dried under vacuum. The solid was suspended in diphenyl ether (15 ml) and heated at reflux under an argon atmosphere for 15 minutes. The reaction mixture was cooled to ambient temperature and diluted with hexane (15 ml). The precipitate which formed was collected by filtration and washed with hexane (3×25 ml) to give 2-amino-5-chloropyrazine (1.78 g); $^1$H NMR (d$_6$-DMSO): 6.55 (br s, 2H), 7.67 (d, 1H), 7.95 (d, 1H); mass spectrum (+ve CI): 130 (M+H)$^+$.

(c) 2-Amino-5-chloropyrazine (1.7 g) was dissolved in chloroform (190 ml) and pyridine (1.3 ml) was added under an argon atomosphere. The flask and its contents were protected from light and a solution of bromine (0.7 ml) in chloroform (85 ml) was added over a period of 1 hour. After stirring for 2 hours more bromine (0.07 ml) in chloroform (8.5 ml) was added. After stirring for 30 minutes, pyridine (0.2 ml) was added. The reaction mixture was stirred for a further 30 minutes then washed with water (50 ml) and the organic phase was separated. Volatile material was removed by evaporation and and the residue was purified by chromatography through a bed of silica (90 g), eluting with hexane (200 ml), followed by dichloromethane. Dichloromethane fractions containing the product were evaporated to give 2-amino-3-bromo-5-chloropyrazine (1.68 g); $^1$H NMR (d$_6$-DMSO): 6.94 (br s, 2H), 8.09 (s, 1H); mass spectrum (+ve CI): 208 (M+H)$^+$.

(d) Sodium (2.82 g) was dissolved in dry methanol (50 ml) under argon and 2-amino-3-bromo-5-chloropyrazine (1.68 g) was added in small portions with stirring. The stirred solution was heated at reflux under an atmosphere of argon for 4 hours. The solution was allowed to cool to ambient temperature and water (10 ml) was added. Volatile material was removed by evaporation and water (10 ml) was added to the residue. The mixture was extracted with dichloromethane (3×50 ml) and the combined extracts were dried (MgSO$_4$) and evaporated to give 2-amino-5-chloro-3-methoxypyrazine (1.28 g), m.p. 102–103° C.; $^1$H NMR (d$_6$-DMSO): 3.90 (s, 3H), 7.53 (s, 1H); mass spectrum (+ve CI): 160 (M+H)$^+$.

EXAMPLE 6

Using an analogous procedure to that described in Example 5, there was thus obtained (in 23% yield) N-(5-chloro-3-methoxypyrazin-2-yl)-2-[4-(N,N-dimethylamino)phenyl]pyridine-3-sulphonamide; $^1$H NMR (d$_6$-DMSO): 3.0 (s, 6H), 3.8 (s, 3H), 6.7 (d, 2H), 7.4 (d, 2H), 7.5 (dd, 1H), 7.7 (s, 1H), 8.4 (dd, 1H), 8.8 (dd, 1H); mass spectrum (+ve ESP): 420 (M+H)$^+$; starting from 4-nitrophenyl 2-[4-(N,N-dimethylamino)phenyl]pyridine-3-sulphonate; $^1$H NMR (d$_6$-DMSO): 3.0 (s, 6H), 6.8 (d, 2H), 7.3 (d, 2H), 7.6 (m, 3H), 8.2 (d, 2H), 8.4 (dd, 1H), 9.0 (dd, 1H); mass spectrum (+ve ESP): 400 (M+H)$^+$; itself obtained using an analogous procedure to that described in Example 5, part (ii) but using 4-(N,N-dimethylamino)phenylboronic acid (obtained by the procedure described in *Annalen der Chemie*, 1971, 753, 80).

EXAMPLE 7

Tetrabutylammonium fluoride (0.45 ml of a 1.0M solution in THF) was added to a solution of 4-(4-isobutylphenyl)-N-(3-methoxy-5-methylpyrazin-2-yl)-N-[2-(trimethylsilyl)ethoxymethyl]pyridine-3-sulphonamide (0.205 g) in dry THF (2 ml) and the solution was heated under reflux for 40 minutes. More tetrabutylammonium fluoride solution (0.95 ml) was added and heating was continued for 2 hours. The reaction mixture was diluted with water (15 ml) and extracted with ether (2×30 ml). The organic extracts were washed with water and saturated sodium chloride solution and then dried (MgSO$_4$). Volatile material was removed by evaporation and the residue was purified by gradient elution with 40–50% ethyl acetate/hexane through a silica gel Mega Bond Elut column followed by recrystallisation from ethyl acetate/hexane to give 4-(4-isobutylphenyl)-N-(3-methoxy-5-methylpyrazin-2-yl)pyridine-3-sulphonamide (0.014 g), m.p. 232–233° C.; $^1$H NMR (d$_6$-DMSO): 0.9 (d, 6H), 1.8 (br m, 1H), 2.1–2.5 (br m, 5H), 3.8 (s, 3H), 7.1–7.3 (m, 4H), 7.35 (d, 1H), 7.5 (s, 1H), 8.75 (d, 1H), 9.1 (s, 1H), 10.4 (s, 1H); mass spectrum (+ve ESP): 413 (M+H)+.

The starting material 4-(4-isobutylphenyl)-N-(3-methoxy-5-methylpyrazin-2-yl)-N-[2-(trimethylsilyl) ethoxymethyl]pyridine-3-sulphonamide was obtained as follows:

(i) 2-Amino-3-methoxy-5-methylpyrazine (0.346 g) was added to a suspension of sodium hydride (60% dispersion in oil; 0.25 g) in DMF (10 ml). After 30 minutes 4-chloropyridine-3-sulphonyl chloride (0.58 g) (obtained by the procedure described in *Ann. Pharm. Fr.*, 1973, 31, 467) was added as a solid, washed in with DMF (1 ml). The mixture was stirred at ambient temperature for a further 2 hours and was then poured into 1M sodium hydrogen sulphate solution (100 ml) and extracted with ethyl acetate (2×100 ml). The organic layers were washed with water (2×100 ml) and saturated sodium chloride solution then combined and dried ($MgSO_4$). Volatile material was removed by evaporation and the residue was purified by gradient elution with 30–50% ethyl acetate/ hexane through a silica gel Mega Bond Elut column followed by recrystallisation from ethyl acetate/hexane to give 4-chloro-N-(3-methoxy-5-methylpyrazin-2-yl) pyridine-3-sulphonamide (0.117 g) which decomposed without melting about 130° C.; $^1$H NMR ($d_6$-DMSO): 2.3 (d, 3H), 4.0 (s, 3H), 8.2 (d, 1H), 8.5 (d, 1H), 9.0 (d, 1H), 9.2 (s, 1H); mass spectrum (+ve ESP): 315 (M+H)+.

(ii) 2-(Trimethylsilyl)ethoxymethyl chloride (0.22 ml) was added dropwise over 5 minutes to a stirred solution of 4-chloro-N-(3-methoxy-5-methylpyrazin-2-yl)pyridine-3-sulphonamide (0.306 g) and N,N-diisopropylethylamine (0.21 ml) in dry DMF (1 ml) at −15° C. The resultant solution was allowed to warm to −5° C. over 40 minutes then ethyl acetate (30 ml) was added and the mixture was washed with 2M hydrochloric acid (30 ml), water (30 ml) and saturated sodium chloride solution and then dried ($MgSO_4$). Volatile material was removed by evaporation and the residue was purified by gradient elution with 30–50% ethyl acetate/hexane through a silica gel Mega Bond Elut column to give 4-chloro-N-(3-methoxy-5-methylpyrazin-2-yl)-N-[2-(trimethylsilyl)ethoxymethyl]pyridine-3-sulphonamide (0.266 g) as an oil; $^1$H NMR ($d_6$-DMSO): −0.1 (s, 9H), 0.7 (t, 2H), 2.45 (s, 3H), 3.6 (t, 2H), 3.85 (s, 3H), 5.2 (s, 2H), 7.8 (d, 1H), 8.0 (s, 1H), 8.8 (d, 1H), 9.1 (s, 1H); mass spectrum (+ve FAB, DMSO/Glycerol): 445 (M+H)+.

(iii) Tetrakis(triphenylphosphine)palladium(0) (0.018 g) was added to a deoxygenated mixture of 4-chloro-N-(3-methoxy-5-methylpyrazin-2-yl)-N-[2(trimethylsilyl)ethoxymethyl]pyridine-3-sulphonamide (0.225 g), 4-isobutylphenylboronic acid (0.109 g), toluene (4 ml), ethanol (2 ml) and 2M sodium carbonate solution (6 ml) and the mixture was stirred and heated under reflux for 18 hours. Ether (25 ml) was added and the mixture was washed with water (2×25 ml) and saturated sodium chloride solution. Aqueous layers were back-extracted with ether (25 ml). The organic extracts were combined and dried ($MgSO_4$). Volatile material was removed by evaporation and the residue was purified by gradient elution with 25–50% ethyl acetate/hexane through a silica gel Mega Bond Elut column to give 4-(4-isobutylphenyl)-N-(3-methoxy-5-methylpyrazin-2-yl)-N-[2-(trimethylsilyl) ethoxymethyl]-pyridine-3-sulphonamide (0.213 g) as an oil; $^1$H NMR ($d_6$-DMSO): −0.1 (s, 9H), 0.7 (t, 2H), 0.9 (d, 6H), 1.9 (m, 1H), 2.45 (s, 3H), 2.5 (d, 2H), 3.5 (t, 2H), 3.8 (s, 3H), 4.7 (s, 2H), 7.2 (d, 2H), 7.3 (d, 2H), 7.4 (d, 1H), 8.0 (s, 1H), 8.8 (d, 1H), 9.2 (s, 1H); mass spectrum (+VE esp): 543 (M+H)+.

EXAMPLE 8

2M Sodium hydroxide solution (1 ml) was added to a solution of N-(isobutoxycarbonyl)-2-(4-[1-(methoxycarbonyl)ethoxy]phenyl)-N-(3-methoxy-5-methylpyrazin-2-yl)pyridine-3-sulphonamide (0.302 g) in methanol (5 ml) and dimethoxyethane (5 ml) and the solution was stirred for 3 days. Volatile material was removed by evaporation and the residue was dissolved in water (15 ml). The solution was washed with ethyl acetate (2×15 ml) and acidified to pH3 with 6M hydrochloric acid. The mixture was extracted with ethyl acetate (2×10 ml) and the extracts were re-extracted with saturated sodium bicarbonate solution (2×10 ml). The aqueous solution was acidified with 2M hydrochloric acid and extracted with ethyl acetate (2×10 ml). The extracts were washed with water (10 ml) and dried ($MgSO_4$). Volatile material was removed by evaporation and the residue was recrystallised from ethyl acetate to give 2-[4-(1-carboxyethoxy)phenyl]-N-(3-methoxy-5-methylpyrazin-2-yl)pyridine-3-sulphonamide (0.098 g), m.p. 149–151 ° C.; microanalysis found: C, 53.6; H, 4.9; N, 11.7%; $C_{18}H_{18}N_4O_6S.02C_4H_8O_2$ requires C, 5.41; H, 4.7; N, 12.1%.

The starting material N-(isobutoxycarbonyl)-2-[4-(1-methoxycarbonyl)ethoxyphenyl]-N-(3-methoxy-5-methylpyrazin-2-yl)pyridine-3-sulphonamide was obtained as follows:

(i) A solution of 4-bromophenol (86.5 g), 3,4-dihydro-2H-pyran (46.2 g) and pyridinium p-toluenesulphonate (1.25 g) in dichloromethane (500 ml) was stirred under argon for 24 hours. The solution was washed with 2M sodium hydroxide solution (200 ml) and water (2×200 ml) and then dried ($MgSO_4$). Volatile material was removed by evaporation and the residue was triturated with hexane to give 2-(4-bromophenoxy)-2H-tetrahydropyran (94.3 g), m.p. 51–53° C.

(ii) tert-Butyl lithium in pentane (1.7M, 200 ml) was added over 20 minutes to a solution of 2-(4-bromophenoxy)-2 H-tetrahydropyran (38.6 g) in dry tetrahydrofuran (450 ml) at −90° C. under argon. The solution was stirred at −90° C. for 30 minutes and then a solution of trimethyl borate (30 ml) in dry tetrahydrofuran (50 ml) was added over 15 minutes. The solution was stirred at −90° C. for 30 minutes and then allowed to warm to −30° C. Saturated ammonium chloride solution (100 ml) was added and the mixture was left to warm to room temperature. Water (100 ml) was added and the mixture was extracted with ether (2×250 ml). The extracts were washed with water (2×200 ml) and dried ($MgSO_4$). Volatile material was removed by evaporation and the residue was recrystallised from a mixture of ether and hexane to give 4-(2 H-tetrahydropyran-2-yloxy)phenylboronic acid (23.4 g), m.p. 140–142° C.

(iii) A solution of potassium fluoride (6.5 g) in water (100 ml) was added to a solution of 2-chloro-N-isobutoxycarbonyl-N-(3-methoxy-5-methylpyrazin-2-yl) pyridine-3-sulphonamide (7.8 g), 4-(2-(2 H)-tetrahydropyranyloxy)phenylboronic acid (10.0 g), tri-o-tolyl phosphine (0.73 g) and palladium acetate (0.25 g) in toluene (100 ml) and the mixture was heated under reflux under argon for 18 hours. Ethyl acetate (150 ml) was added and the organic phase was separated. The solution was washed with 2M sodium hydroxide solution (100 ml) and water (250 ml) and then dried ($MgSO_4$). Volatile material was removed by evaporation and the residue was purified by flash chromatography, eluting with 25–50% ethyl acetate/hexane. The residue was crystallised from ethyl acetate/hexane to give N-(isobutoxycarbonyl)-2-[4-(2H-tetrahydropyran-2-yloxy)phenyl]-N-(3-methoxy-5-methylpyrazin-2-yl)pyridine-3-sulphonamide (4.0 g), m.p. 142–144° C.

(iv) A solution of N-(isobutoxycarbonyl)-2-[4-(2H-tetrahydropyran-2-yloxy)phenyl]-N-(3-methoxy-5-methylpyrazin-2-yl)pyridine-3-sulphonamide (5.9 g) and pyridinium p-toluenesulphonate (0.27 g) in ethanol (150 ml) was heated at 60° C. for 3 hours. Volatile material was removed by evaporation and the residue was purified by flash chromatography, eluting with ethyl acetate/hexane (2:3 v/v). The residue was triturated with ethyl acetate/hexane (1:9 v/v) to give 2-(4-hydroxyphenyl)-N-(isobutoxycarbonyl)-N-(3-methoxy-5-methylpyrazin-2-yl)pyridine-3-sulphonamide (4.7 g), m.p. 144–146° C.

(v) A mixture of 2-(4-hydroxyphenyl)-N-(isobutoxycarbonyl)-N-(3-methoxy-5-methylpyrazin-2-yl)pyridine-3-sulphonamide (0.472 g), methyl 2-bromopropionate (217 mg) and potassium carbonate (166 mg) in acetone (20 ml) was heated under reflux for 15 hours. Volatile material was removed by evaporation and water (25 ml) was added to the residue. The mixture was extracted with ethyl acetate (25 ml) and the extracts were washed with 2M sodium hydroxide solution (10 ml) and water (20 ml). The solution was dried ($MgSO_4$) and the solvent was removed by evaporation. The residue was purified by flash chromatography, eluting with ethyl acetate/hexane (1:1 v/v), to give N-(isobutoxycarbonyl)-2-(4-[1-(methoxycarbonyl)ethoxy]phenyl)-N-(3-methoxy-5-methylpyrazin-2-yl)pyridine-3-sulphonamide (0.32 g); $^1$H NMR (DMSO-$d_6$): 0.6 (d, 6H), 1.5–1.7 (m, 4H), 2.5 (s, 3H), 3.7 (s, 3H), 3.8 (d, 2H), 4.0 (s, 3H), 5.1 (q, 1H), 6.95 (d, 2H), 7.5 (d, 2H), 7.7–7.8 (m, 1H), 8.2 (s, 1H), 8.85 (d, 1H), 8.9 (d, 1H).

EXAMPLE 9

Sodium methoxide (0.115 g) was added to a solution of 2-[4-(N,N-dimethylamino)phenyl]-N-(isobutoxycarbonyl)-N-(3-methoxy-5-methylpyrazin-2-yl)pyridine-3-sulphonamide (0.212 g) in methanol (10 ml) and the mixture was stirred and heated under reflux for 90 minutes. The reaction mixture was cooled, poured into saturated aqueous ammonium chloride solution (30 ml) and extracted with ethyl acetate (3×30 ml). The organic extracts were combined and dried ($MgSO_4$). Volatile material was removed by evaporation and the residue was triturated with ether to give 2-[4-(N,N-dimethylamino)phenyl]-N-(3-methoxy-5-methylpyrazin-2-yl)pyridine-3-sulphonamide (104 mg) as a solid, m.p. 183–184.5° C.; $^1$H NMR ($d_6$-DMSO): 2.2 (s, 3H), 2.95 (s, 6H), 3.8 (s, 3H), 6.7 (br s, 2H), 7.3–7.5 (m, 4H), 8.37 (dd, 1H), 8.7 (dd, 1H), 10.1 (br s, 1H); mass spectrum (+ve FAB, DMSO/methanol/NBA): 400 (M+H)$^+$.

The starting material 2-[4-(N,N-dimethylamino)phenyl]-N-(isobutoxycarbonyl)-N-3-methoxy-5-methylpyrazin-2-yl)pyridine-3-sulphonamide was obtained in 51% yield using an analogous procedure to that described in Example 8, part (iii) but using 4-(N,N-dimethylamino)phenylboronic acid; $^1$H NMR ($d_6$-DMSO): 0.6 (d, 6H), 1.6 (m, 1H), 2.55 (s, 3H), 3.0 (s, 6H), 3.8 (d, 2H), 4.0 (s, 3H), 6.7 (d, 2H), 7.45 (d, 2H), 7.6 (dd, H), 8.2 (s, 1H), 8.85 (m, 2H); mass spectrum (+ve FAB, DMSO/NBA): 500 (M+H)$^+$.

EXAMPLE 10

Using an analogous procedure to that described in Example 1, there was thus obtained (in 32% yield) 2-(4-chlorophenyl)-N-(3-methoxy-5-methylpyrazin-2-yl)pyridine-3-sulphonamide; $^1$H NMR (CDCl$_3$): 2.3 (s, 3H), 3.85 (s, 3H), 6.7 (s, 1H), 7.25–7.45 (m, 5H), 7.5 (dd, 1H), 8.65 (d, 1H), 8.8 (d, 1H); mass spectrum (+ve ESP): 391 (M+H)$^{30}$; starting from 2-(4-chlorophenyl)-N-isobutoxycarbonyl-N-(3-methoxy-5-methylpyrazin-2-yl)pyridine-3-sulphonamide; $^1$H NMR (CDCl$_3$): 0.65 (d, 6H), 1.7 (m, 1H), 2.5 (s, 3H), 3.8 (d, 2H), 4.0 (s, 3H), 7.35–7.6 (m, 5H), 7.9 (s, 1H), 8.85 (dd, 1H), 8.95 (dd, 1H); mass spectrum (+ve ESP): 491 (M+H)$^+$; itself obtained using an analogous procedure to that described in Example 1, part (iii) but using 4-chlorophenylboronic acid.

EXAMPLE 11

2M Sodium hydroxide solution (1 ml) was added to a solution of N-(isobutoxycarbonyl)-2-(4-propylphenyl)-N-(3-methoxy-5-methylpyrazin-2-yl)pyridine-3-sulphonamide (0.7 g) in methanol (2 ml) and the reaction mixture stirred for 17 hours at ambient temperature. The methanol was removed by evaporation and water (20 ml) was added. The reaction mixture was extracted with ethyl acetate (4×15 ml), the combined organic extracts were dried ($MgSO_4$) and then the solvent was removed by evaporation. The resultant oil was purified by eluting with 30% ethyl acetate/isohexane through a silica gel Mega Bond Elut column, followed by trituration with isohexane/diethyl ether to give 2-(4-propylphenyl)-N-(3-methoxy-5-methylpyrazin-2-yl)pyridine-3-sulphonamide (0.4 g) as a solid, m.p. 70–72° C.; mass spectrum (+ve ESP): 399 (M+H)$^+$.

The starting material N-(isobutoxycarbonyl)-2-(4-propylphenyl)-N-(3-methoxy-5-methylpyrazin-2-yl)pyridine-3-sulphonamide was obtained as follows:

(i) n-Butyl lithium (34 ml of a 1.6 M solution in hexanes) was added dropwise to a stirred solution of 1-bromo-4-propylbenzene (9.96 g) in dry THF (30 ml) at −70° C. under argon. The reaction was stirred for 1 hour at −70° C. before addition of triisopropyl borate (12.7 ml) and then stirred for a further 90 minutes at −70° C. before addition of saturated aqueous ammonium chloride solution (30 ml). The reaction was stirred at −70° C. for a further 10 minutes, water (100 ml) was added and the reaction was allowed to warm to ambient temperature. The reaction mixture was extracted with diethyl ether (3×50 ml), the combined organic layers were dried ($MgSO_4$) and then the solvent was removed by evaporation. Trituration of the resultant clear oil with isohexane gave 4-propylphenylboronic acid as a white solid, 6.7 g, mass spectrum (negative electrospray (−ve ESP)): 163 (M−H)$^-$.

(ii) Tetrakis(triphenylphosphine)palladium(0) (60 mg) was added to a deoxygenated solution of sodium carbonate (212 mg), 4-propylphenylboronic acid (328 mg) and 2-chloro-N-(isobutoxycarbonyl)-N-(3-methoxy-5-methylpyrazin-2-yl)pyridine-3-sulphonamide (828 mg) in a mixture of water (5 ml), ethanol (8 ml) and toluene (16 ml). The mixture was stirred and heated under argon at 80° C. for 17 hours and then allowed to cool to ambient temperature. Ice water (25 g) was added and the reaction extracted with ethyl acetate (3×50 ml). The combined organic layers were dried ($MgSO_4$) and evaporated to afford an amber oil. This was purified by chromatography on a silica gel Mega Bond Elut column, eluting with 20% ethyl acetate/isohexane to give N-(isobutoxycarbonyl)-2-(4-propylphenyl)-N-(3-methoxy-5-methylpyrazin-2-yl)pyridine-3-sulphonamide (760 mg) as a solid, mass spectrum (+ve ESP): 499 (M+H)$^+$.

EXAMPLE 12

Using an analogous procedure to that described in Example 11, there was thus obtained (in 72% yield) 2-(4- ethylphenyl)-N-(3-methoxy-5-methylpyrazin-2-yl)pyridine-3-sulphonamide as a white crystalline solid, m.p. 73–75° C.; $^1$H NMR (DMSO-$d_6$); 1.2 (t, 3H), 2.25 (s, 3H), 2.65 (q, 2H), 3.8 (s, 3H), 7.2 (d, 2H), 7.4 (d, 2H), 7.6 (dd, 1H), 8.45 (dd, 1H), 8.8 (dd, 1H); mass spectrum (+ve ESP): 385 (M+H)$^+$; starting from N-(isobutoxycarbonyl)-2-(4-ethylphenyl)-N-(3-methoxy-5-methylpyrazin-2-yl)pyridine-3-sulphonamide.

The starting material N-(isobutoxycarbonyl)-2-(4-ethylphenyl)-N-(3-methoxy-5-methylpyrazin-2-yl)pyridine-3-sulphonamide was obtained as follows:
(i) Using an analogous procedure to that described in Example 11 part (i) but using 1-bromo-4-ethylbenzene as starting material, there was thus obtained (in 93% yield) 4-ethylphenylboronic acid as a white solid, mass spectrum (−ve ESP): 149 (M−H)$^−$.
(ii) Using an analogous procedure to that described in Example 11 part (ii) but using 4-ethylphenylboronic acid, there was thus obtained (in 36% yield) N-(isobutoxycarbonyl)-2-(4-ethylphenyl)-N-(3-methoxy-5-methylpyrazin-2-yl)pyridine-3-sulphonamide as a white crystalline solid, mass spectrum (+ve ESP): 485 (M+H)$^+$.

EXAMPLE 13

Using an analogous procedure to that described in Example 11, there was thus obtained (in 48% yield) 2-(4-tert-butylphenyl)-N-(3-methoxy-5-methylpyrazin-2-yl)pyridine-3-sulphonamide as a white crystalline solid, m.p. 150–151° C.; $^1$H NMR (DMSO-$d_6$); 1.3 (s, 9H), 2.25 (s, 3H), 3.8 (s, 3H), 7.4 (m, 4H), 7.6 (dd, 1H), 8.4 (d, 1H), 8.8 (d, 1H); mass spectrum (+ve ESP): 413 (M+H)$^+$; starting from N-(isobutoxycarbonyl)-2-(4-tert-butylphenyl)-N-(3-methoxy-5-methylpyrazin-2-yl)pyridine-3-sulphonamide.

The starting material N-(isobutoxycarbonyl)-2-(4-tert-butylphenyl)-N-(3-methoxy-5-methylpyrazin-2-yl)pyridine-3-sulphonamide was obtained as follows:
i) Using an analogous procedure to that described in Example 11 part (i) but using 1-bromo-4-tert-butylbenzene as starting material, there was thus obtained (in 81% yield) 4-tert-butylphenylboronic acid (81%) as a white solid, mass spectrum (−ve ESP): 177 (M−H)$^−$.
ii) Using an analogous procedure to that described in Example 11 part (ii) but starting from 4-tert-butylphenylboronic acid, there was thus obtained (in 33% yield) N-(isobutoxycarbonyl)-2-(4-tert-butylphenyl)-N-(3-methoxy-5-methylpyrazin-2-yl)pyridine-3-sulphonamide as a white crystalline solid, mass spectrum (+ve ESP): 513 (M+H)$^+$.

EXAMPLE 14

Using an analogous procedure to that described in Example 11, there was thus obtained (in 42% yield) 2-(4-isopropylphenyl)-N-(3-methoxy-5-methylpyrazin-2-yl)pyridine-3-sulphonamide as a white crystalline solid, m.p.74–75° C.; mass spectrum (+ve ESP): 399 (M+H)$^+$; starting from N-(isobutoxycarbonyl)-2-(4-isopropylphenyl)-N-(3-methoxy-5-methylpyrazin-2-yl)pyridine-3-sulphonamide.

The starting material N-(isobutoxycarbonyl)-2-(4-isopropylphenyl)-N-(3-methoxy-5-methylpyrazin-2-yl)pyridine-3-sulphonamide was obtained as follows:
(i) Using an analogous procedure to that described in Example 11 part (i) but using 1-bromo-4-isopropylbenzene as starting material, there was thus obtained (in 93% yield) 4-isopropylphenylboronic acid as a white solid, mass spectrum (−ve ESP): 163 (M−H)$^−$.
(ii) Using an analogous procedure to that described in Example 11 part (ii) but using 4-isopropylphenylboronic acid, there was thus obtained (in 45% yield) N-(isobutoxycarbonyl)-2-(4-isopropylphenyl)-N-(3-methoxy-5-methylpyrazin-2-yl)pyridine-3-sulphonamide as a white crystalline solid, mass spectrum (+ve ESP): 499 (M+H)$^+$.

EXAMPLE 15

Using an analogous procedure to that described in Example 11, there was thus obtained (in 33% yield) 2-(4-vinylphenyl)-N-(3-methoxy-5-methylpyrazin-2-yl)pyridine-3-sulphonamide as a white crystalline solid, m.p. 110–112° C.; mass spectrum (+ve ESP): 383 (M+H)$^+$; starting from N-(isobutoxycarbonyl)-2-(4-vinylphenyl)-N-(3-methoxy-5-methylpyrazin-2-yl)pyridine-3-sulphonamide.

The starting material N-(isobutoxycarbonyl)-2-(4-vinylphenyl)-N-(3-methoxy-5-methylpyrazin-2-yl)pyridine-3-sulphonamide was obtained as follows:
(i) Using an analogous procedure to that described in Example 11 part (i) but using 1-bromo-4-vinylbenzene as starting material, there was thus obtained (in 82% yield) 4-vinylphenylboronic acid as a white solid, mass spectrum (−ve ESP): 149 (M−H)$^−$.
(ii) Using an analogous procedure to that described in Example 11 part (ii) but using 4-vinylphenylboronic acid, there was thus obtained (in 27% yield) N-(isobutoxycarbonyl)-2-(4-vinylphenyl)-N-(3-methoxy-5-methylpyrazin-2-yl)pyridine-3-sulphonamide as a white crystalline solid, mass spectrum (+ve ESP): 483 (M+H)$^+$.

EXAMPLE 16

Using an analogous procedure to that described in Example 11, there was thus obtained (in 30% yield) 2-(4-(N,N-diethylamino)phenyl)-N-(3-methoxy-5-methylpyrazin-2-yl)pyridine-3-sulphonamide as a white crystalline solid, m.p. 115–117° C.; mass spectrum (+ve ESP): 428 (M+H)$^+$; starting from N-(isobutoxycarbonyl)-2-(4-(N,N-diethylamino)phenyl)-N-(3-methoxy-5-methylpyrazin-2-yl)pyridine-3-sulphonamide.

The starting material N-(isobutoxycarbonyl)-2-(4-(N,N-diethylamino)phenyl)-N-(3-methoxy-5-methylpyrazin-2-yl)pyridine-3-sulphonamide was obtained as follows:
(i) Using an analogous procedure to that described in Example 11 part (i) but using 4-bromo-N,N-diethylaniline as starting material, there was thus obtained (in 76% yield) 4-(N,N-diethylamino)phenylboronic acid as a white solid, mass spectrum (−ve ESP): 192 (M−H)$^−$.
(ii) Using an analogous procedure to that described in Example 11 part (ii) but using 4-(N,N-diethylamino)phenylboronic acid as starting material, there was thus obtained (in 31% yield) N-(isobutoxycarbonyl)-2-(4-(N,N-diethylamino)phenyl)-N-(3-methoxy-5-methylpyrazin-2-yl)pyridine-3-sulphonamide as a white crystalline solid, mass spectrum (+ve ESP): 528 (M+H)$^+$.

EXAMPLE 17

Using an analogous procedure to that described in Example 11, there was thus obtained (in 50% yield) 2-(4-propoxyphenyl)-N-(3-methoxy-5-methylpyrazin-2-yl)pyridine-3-sulphonamide as a white crystalline solid, m.p. 134–135° C.; mass spectrum (+ve ESP): 415 (M+H)$^+$; starting from N-(isobutoxycarbonyl)-2-(4-propoxyphenyl)-N-(3-methoxy-5-methylpyrazin-2-yl)pyridine-3-sulphonamide.

The starting material N-(isobutoxycarbonyl)-2-(4-propoxyphenyl)-N-(3-methoxy-5-methylpyrazin-2-yl)pyridine-3-sulphonamide was obtained as follows:
(i) A mixture of 4-bromophenol (8.65 g), potassium iodide (83 mg), potassium carbonate (6.9 g) and propyl bromide (6.15 g) was heated under reflux in acetone (100 ml) for 48 hours. The reaction was cooled to ambient temperature, filtered and the acetone removed in vacuo to give an amber oil. This was purified by gradient elution with 20% ethyl acetate/isohexane through a silica gel Mega Bond Elut column to give 1-bromo-4-propoxybenzene (9.4 g) as a clear oil, mass spectrum (+ve CI): 214 $(M+H)^+$.
(ii) Using an analogous procedure to that described in Example 11 part (i) but starting from 1-bromo-4-propoxybenzene, there was thus obtained (in 95% yield) 4-propoxyphenylboronic acid as a white solid, mass spectrum (−ve ESP): 179 $(M-H)^-$.
(iii) Using an analogous procedure to that described in Example 11 part (ii) but starting from 4-propoxyphenylboronic acid, there was thus obtained (in 46% yield) N-(isobutoxycarbonyl)-2-(4-propoxyphenyl)-N-(3-methoxy-5-methylpyrazin-2-yl)pyridine-3-sulphonamide as a white crystalline solid, mass spectrum (+ve ESP): 515 $(M+H)^+$.

EXAMPLE 18

Using an analogous procedure to that described in Example 11, there was thus obtained (in 46% yield) 2-(4-ethoxyphenyl)-N-(3-methoxy-5-methylpyrazin-2-yl)pyridine-3-sulphonamide as a white crystalline solid, m.p.162–163° C.; mass spectrum (+ve ESP): 401 $(M+H)^+$; starting from N-(isobutoxycarbonyl)-2-(4-ethoxyphenyl)-N-(3-methoxy-5-methylpyrazin-2-yl)pyridine-3-sulphonamide.

The starting material N-(isobutoxycarbonyl)-2-(4-ethoxyphenyl)-N-(3-methoxy-5-methylpyrazin-2-yl)pyridine-3-sulphonamide was obtained as follows:
(i) Using an analogous procedure to that described in Example 17 part (i) but using ethyl bromide as starting material, there was thus obtained (in 76% yield) 1-bromo-4-ethoxybenzene as a clear oil, mass spectrum (+ve CI): 200 $(M+H)^+$.
(ii) Using an analogous procedure to that described in Example 11 part (i) but starting from 1-bromo-4-ethoxybenzene, there was thus obtained (in 96% yield) 4-ethoxyphenylboronic acid as a white solid, mass spectrum (−ve ESP): 165 $(M-H)^-$.
(iii) Using an analogous procedure to that described in Example 11 part (ii) but starting from 4-ethoxyphenylboronic acid, there was thus obtained (in 36% yield) N-(isobutoxycarbonyl)-2-(4-ethoxyphenyl)-N-(3-methoxy-5-methylpyrazin-2-yl)pyridine-3-sulphonamide as a white crystalline solid, mass spectrum (+ve ESP): 501 $(M+H)^+$.

EXAMPLE 19

Tetrabutylammonium fluoride (0.4 ml of a 1.0 M solution in THF) was added to a solution of 2-[4-(2-((tert-butyldimethylsiloxy)methyl)propyl)phenyl]-N-(3-methoxy-5-methylpyrazin-2-yl)pyridine-3-sulphonamide (118 mg) in THF (5 ml) at ambient temperature. More tetrabutylammonium fluoride solution was added after 0.25 hour (0.4 ml), after 0.75 hour (1.0 ml) and finally after 1.5 hours (0.2 ml). The reaction mixture was stirred for a further 0.5 hour, diluted with water (10 ml) and the reaction mixture was extracted with dichloromethane (4×10 ml). The combined organic extracts were dried over $MgSO_4$ and evaporated to give an amber oil. This was purified by gradient elution with 0–50% methanol/dichloromethane through a silica gel Mega Bond Elut column to give 2-[4-(3-hydroxy-2-methylpropyl)phenyl]-N-(3-methoxy-5-methylpyrazin-2-yl)pyridine-3-sulphonamide (75 mg) as a white crystalline solid, m.p. 118–119° C.; $^1H$ NMR (DMSO-$d_6$): 0.95 (d, 3H), 1.35 (m, 1H), 2.0 (m, 1H), 2.3 (s, 3H), 2.5 (m, 1H), 2.9 (m, 1H), 3.5 (m, 2H), 3.8 (s, 3H), 6.65 (s, 1H), 7.2 (m, 4H), 7.35 (s, 1H), 7.5 (m, 1H), 8.7 (d, 1H), 8.8 (dd, 1H); mass spectrum (+ve ESP): 429 $(M+H)^+$.

The starting material 2-[4-(2-((tert-butyldimethylsiloxy)methyl)propyl)phenyl]-N-(3-methoxy-5-methylpyrazin-2-yl)pyridine-3-sulphonamide was obtained as follows:
(i) Sodium ethoxide was generated by the addition of sodium (9.45 g) to ethanol (370 ml). The resulting solution was cooled to 5° C. and diethyl 2-methylmalonate (68.8 ml) added over 2 minutes. The reaction mixture was stirred at 5° C. for 20 minutes and then 4-bromobenzyl bromide (97.0 g) was added over 20 minutes. The reaction mixture was then heated under reflux for 16 hours. The reaction mixture was cooled to ambient temperature, filtered through diatomaceous earth and evaporated. The residue was partitioned between water (500 ml) and diethyl ether (1000 ml). The diethyl ether was separated and the aqueous layer was extracted with diethyl ether (2×500 ml). The combined organic layers were dried ($MgSO_4$) and evaporated to give an amber oil. This was purified by vacuum distillation, affording diethyl 2-(4-bromobenzyl)-2-methylmalonate (84.4 g), b.p.122–125° C./0.1–0.2 mm Hg; mass spectrum (+ve CI): 343 $(M+H)^+$.
(ii) A solution of sodium hydroxide (34.0 g) in water (155 ml) was added to a solution of diethyl 2-(4-bromobenzyl)-2-methylmalonate (29.2 g) in ethanol (165 ml), and then heated under reflux for 9 hours. The reaction mixture was cooled, the solvent was evaporated and the residue taken up in water (150 ml). Sodium hydroxide pellets were added (25.4 g) and the reaction mixture was heated under reflux for 2 hours. The reaction mixture was then cooled and acidified to pH<1 with concentrated hydrochloric acid, which caused precipitation of a solid. The reaction mixture was extracted with diethyl ether (3×150 ml), the combined organic layers were dried ($MgSO_4$) and then the solvent was evaporated to give a white solid. This solid was heated at 205° C. for 20 minutes, cooled to ambient temperature, dissolved in 1.0 M sodium hydroxide solution (150 ml), treated with activated charcoal and then filtered through diatomaceous earth. The resulting clear solution was re-acidified and then extracted with diethyl ether (3×150 ml). The combined organic layers were dried ($MgSO_4$) and evaporated to give a yellow oil which crystallised on standing to give 2-methyl-3-(4-bromophenyl)propanoic acid as a white solid (18.2 g), m.p. 69–70° C.; mass spectrum (+ve CI): 243 $(M+H)^+$.
(iii) Diborane (192 ml of a 1.0 M solution in THF) was added dropwise over 25 minutes to a solution of 2-methyl-3-(4-bromophenyl)propanoic acid (38.9 g) in THF (240 ml) at 0° C. The reaction mixture was stirred for 45 minutes at 0° C. and then allowed to warm to ambient temperature over 2 hours. Water (120 ml) was added followed by solid potassium carbonate (144 g) and then more water (80 ml). The reaction mixture was extracted with diethyl ether (3×250 ml), the combined organic layers were dried ($MgSO_4$) and the solvent was evaporated to give 2-methyl-3-(4-bromophenyl)propanol as a yellow oil (37.4 g), mass spectrum (+ve CI): 248 $(M+NH4)^+$.

(iv) A solution of imidazole (27.2 g) in DMF (100 ml) was added to a stirred solution of 2-methyl-3-(4-bromophenyl)propanol (37.4 g) and tert-butyldimethylsilyl chloride (28.9 g) in dry DMF (100 ml) at 0° C. The reaction mixture was allowed to stir, warming to ambient temperature, over 21 hours and was then poured onto ice (500 g). The reaction mixture was extracted with diethyl ether (3×500 ml), the combined organic layers were dried (MgSO$_4$) and the solvent was evaporated to give 1-(tert-butyldimethylsiloxy)-2-methyl-3-(4-bromophenyl)propane as a yellow oil (53.3 g), mass spectrum (+ve CI): 343 (M+H)$^+$.

(v) Using an analogous procedure to that described in Example 11 part (i) but using1-(tert-butyldimethylsiloxy)-2-methyl-3-(4-bromophenyl) propane as starting material, there was thus obtained (in 93% yield) 4-[2-((tert-butyldimethylsiloxy)methyl) propyl]-phenylboronic acid as a white solid, mass spectrum (−ve ESP): 149 (M−H)$^−$.

(vi) Using an analogous procedure to that described in Example 11 part (ii) but using 4-[2-((tert-butyldimethylsiloxy)methyl)propyl)phenylboronic acid as starting material, there was thus obtained (in 36% yield) N-(isobutoxycarbonyl)-2-[4-(2-((tert-butyldimethylsilyl)methyl)propyl)phenyl]-N-(3-methoxy-5-methylpyrazin-2-yl)pyridine-3-sulphonamide as a white crystalline solid, mass spectrum (+ve ESP): 485 (M+H)$^+$.

(vii) Using an analogous procedure to that described in Example 11 but using N-(isobutoxycarbonyl)-2-[4-(2-((tert-butyldimethylsiloxy)methyl)propyl)phenyl]-N-(3-methoxy-5-methylpyrazin-2-yl)pyridine-3-sulphonamide as starting material, there was thus obtained (in 55% yield) 2-[4-(2-((tert-butyldimethylsiloxy)methyl)propyl) phenyl]-N-(3-methoxy-5-methylpyrazin-2-yl)pyridine-3-sulphonamide as a clear oil, $^1$H NMR (DMSO-d$_6$); 0.0 (s, 6H), 0.60 (d, 6H), 0.8 (d, 3H), 0.9 (s, 9H), 1.6 (m, 1H), 1.9 (m, 1H), 2.4–2.6 (m, 4H), 2.75 (m, 1H), 3.4 (dd, 2H), 3.8 (d, 2H), 3.95 (s, 3H), 7.2 (d, 2H), 7.4 (d, 2H), 7.8 (s, 1H), 8.15 (s, 1H), 8.8–8.9 (m, 2H); mass spectrum (+ve ESP):643 (M+H)$^+$.

EXAMPLE 20

Using an analogous procedure to that described in Example 9, there was thus obtained (in 52% yield) 2-(4-acetamidophenyl)-N-(3-methoxy-5-methylpyrazin-2-yl) pyridine-3-sulphonamide as a solid, m.p. 208–209° C.; $^1$H NMR (d$_6$-DMSO): 2.1 (s, 3H), 2.2 s, 3H), 3.8 (s, 3H), 7.4 (d, 2H), 7.4–7.6 (m, 4H), 8.4 (d, 1H), 8.8 (d, 1H), 10.0 (br s, 1H), 10.4 (br s, 1H); mass spectrum (+ve ESP): 414 (M+H)$^+$; starting from 2-(4-acetamidophenyl)-N-isobutoxycarbonyl-N-(3-methoxy-5-methylpyrazin-2-yl) pyridine-3-sulphonamide; $^1$H NMR (d$_6$-DMSO): 0.6 (d, 6H), 1.6 (m, 1H), 2.1 (s, 3H), 2.6 (s, 3H), 3.8 (d, 2H), 4.0 (s, 3H), 7.4 (d, 2H), 7.6 (d, 2H), 7.8 (dd, 1H), 8.15 (s, 1H), 8.85 (dd, 1H), 8.9 (dd, 1H), 10.0 (s, 1H); mass spectrum (+ve ESP): 514 (M+H)$^+$; which was itself obtained using an analogous procedure to that described in Example 11, part (ii) but using 4-acetamidophenylboronic acid; $^1$H NMR (d$_6$-DMSO): 2.1 (s, 3H), 7.5 (d, 2H), 7.7 (d, 2H), 7.8 (s, 2H), 9.9 (br s, 1H). 4-Acetamidophenylboronic acid was obtained using an analogous procedure to that described in Example 11, part (i), except that 4'-bromoacetanilide was used, one equivalent of sodium hydride was added before cooling to −78° C. and ethyl acetate was used for extraction of the product.

EXAMPLE 21

Using an analogous procedure to that described in Example 1, there was thus obtained (in 45% yield) 2-(4-acetylphenyl)-N-(3-methoxy-5-methylpyrazin-2-yl) pyridine-3-sulphonamide; $^1$H NMR (CDCl$_3$): 2.3 (s, 3H), 2.65 (s, 3H), 3.8 (s, 3H), 6.7 (s, 1H), 7.35 (s, 1H), 7.4 (d, 2H), 7.5 (dd, 1H), 7.95 (d 2H), 8.7 (d, 1H), 8.8 (d, 1H); mass spectrum (+ve ESP): 399 (M+H)$^+$; starting from 2-(4-acetylphenyl)-N-isobutoxycarbonyl-N-(3-methoxy-5-methylpyrazinyl)pyridine-3-sulphonamide; $^1$H NMR (CDCl$_3$): 0.7 (d, 6H), 1.7 (m, 1H),2.5 (s, 3H), 2.65 (s, 3H), 3.85 (d, 2H), 4.0 (s, 3H), 7.5 (dd, 1H), 7.7 (d, 2H), 7.9 (s, 1H), 8.0 (d, 2H), 8.85 (dd, 1H), 8.95 (dd, 1H); mass spectrum (+ve ESP): 499 (M+H)$^+$; itself obtained using an analogous procedure to that described in Example 1, part (iii) but using 4-acetylphenylboronic acid (obtained as described in *British Patent Application,* publication no. 2276160).

EXAMPLE 22

Sodium tetrahydridoborate (0.051 g) was added portionwise over 5 minutes to a solution of 2-(4-acetylphenyl)-N-(3-methoxy-5-methylpyrazin-2-yl)pyridine-3-sulphonamide (0.135 g) in ethanol (5 ml). The mixture was stirred for 45 minutes at ambient temperature and was then poured into water (20 ml) and acidified to pH 3 with 2M hydrochloric acid. The mixture was extracted with ethyl acetate (3×20 ml). The extracts were combined, washed with water and saturated sodium chloride solution and dried (MgSO$_4$). Volatile material was removed by evaporation and the residue was purified by gradient elution with 10–70% ethyl acetate/hexane through a silica gel Mega Bond Elut column to give 2-[4-(1-hydroxyethyl)phenyl]-N-(3-methoxy-5-methylpyrazin-2-yl)pyridine-3-sulphonamide (0.096 g) as a foam; $^1$H NMR (CDCl$_3$+CD$_3$COOD): 1.55 (d, 3H), 2.3 (s, 3H), 3.85 (s, 3H), 4.95 (q, 1H), 7.25 (s, 1H), 7.3 (d, 2H), 7.35 (d, 2H), 7.55 (dd, 1H), 8.7 (d, 1H), 8.85 (d, 1H); mass spectrum (+ve ESP): 401 (M+H)$^+$.

EXAMPLE 23

Using an analogous procedure to that described in Example 1 except that dimethoxyethane was added to dissolve reactants, there was thus obtained (in 69% yield) 2-(4-allylphenyl)-N-(3-methoxy-5-methylpyrazin-2-yl) pyridine-3-sulphonamide; $^1$H NMR (CDCl$_3$): 2.25 (s, 3H), 3.5 (d, 2H), 3.8 (s, 3H), 5.15 (m, 2H), 6.0 (m, 1H), 6.65 (s, 1H), 7.15–7.3 (m, 4H), 7.35 (s, 1H), 7.45 (dd, 1H), 8.65 (dd, 1H), 8.8 (dd, 1H); mass spectrum (+ve ESP): 397 (M+H)$^+$; starting from 2-(4-allylphenyl)-N-isobutoxycarbonyl-N-(3-methoxy-5-methylpyrazin-2-yl)pyridine-3-sulphonamide.

The starting 2-(4-allylphenyl)-N-isobutoxycarbonyl-N-(3-methoxy-5-methylpyrazin-2-yl)pyridine-3-sulphonamide was obtained as follows:

(i) Using an analogous procedure to that described in Example 11, part (i), there was thus obtained (in 37% yield) 4-allylphenylboronic acid, $^1$H NMR (CDCl$_3$): 3.38–3.53 (m, 2H), 5.03–5.18 (m, 2H), 5.88–6.10 (m, 1H), 7.34 (d, 2H), 8.15 (d, 2H); mass spectrum (−ve ESP 161 (M−H)$^−$; starting from 4-allyl-1-bromobenzene (obtained as described in *J. Org. Chem.,* 1970,35, 1777.

(ii) Using an analogous procedure to that described in Example 11, part (ii) but starting from 4-allylphenylboronic acid, there was thus obtained (in 48% yield) 2-(4-allylphenyl)-N -isobutoxycarbonyl-N-(3-methoxy-5-methylpyrazin-2-yl)pyridine-3-sulphonamide, $^1$H NMR (CDCl$_3$): 0.7 (d, 6H), 1.7 (m, 1H), 2.5 (s, 3H), 3.45 (d, 2H), 3.8 (d, 2H), 4.0 (s, 3H), 5.1 (m, 2H), 6.0 (m, 1H), 7.23 (d, 2H), 7.5 (dd, 1H), 7.55 (d, 2H), 7.9 (s, 1H), 8.85 (dd, 1H), 9.0 (dd, 1H); mass spectrum (+ve ESP): 497 (M+H)$^+$.

EXAMPLE 24

Using an analogous procedure to that described in Example 9, there was thus obtained (in 79% yield) N-(3-methoxy-5-methylpyrazin-2-yl)-2-[4-(isopropylamino) phenyl]pyridine-3-sulphonamide as a solid, m.p. 105–107° C.; $^1$H NMR (d$_6$-DMSO): 1.2 (d, 6H), 2.3 (s, 3H), 3.8 (s, 3H), 3.6 (m, 1H), 6.6 (br s, 2H), 7.4 (br s, 1H), 7.45 (dd, 1H), 8.4 (dd, 1H), 8.7 (dd, 1H), 10.1 (br s, 1H); mass spectrum (+ve ESP): 414 (M+H)$^+$; starting from N-isobutoxycarbonyl-N-(3-methoxy-5-methyl-pyrazin-2-yl)-2-[4-(isopropylamino)phenyl]pyridine-3-sulphonamide.

The starting material N-isobutoxycarbonyl-N-(3-methoxy-5-methylpyrazin-2-yl)-2-[4-(isopropylamino) phenyl]pyridine-3-sulphonamide was obtained as follows:

(i) Using an analogous procedure to that described in Example 11 part (ii), but using twice the proportionate amount of 4-aminophenyl boronic acid as starting material, there was thus obtained (in 50% yield) 2-(4-aminophenyl)-N-(isobutoxycarbonyl)-N-(3-methoxy-5-methylpyrazin-2-yl)pyridine-3-sulphonamide as a solid; $^1$H NMR (d$_6$-DMSO): 0.6 (d, 6H), 1.6 (m, 1H), 2.55 (s, 3H), 3.8 (d, 2H), 4.0 (s, 3H), 5.45 (br s, 2H), 6.5 (d, 2H) 7.3 (d, 2H), 7.6 (dd, 1H), 8.2 (s, 1H), 8.8 (m, 2H); mass spectrum (+ve ESP): 472 (M+H)$^+$.

(ii) A solution of 2-(4-aminophenyl)-N-(isobutoxycarbonyl)-N-(3-methoxy-5-methylpyrazin-2-yl)pyridine-3-sulphonamide (0.17 g) in acetone (3 ml) and water (3 ml) was acidified to pH 4 with glacial acetic acid. Sodium cyanotrihydridoborate (0.045 g) was added and the mixture was stirred at ambient temperature for 16 hours. The mixture was then poured into 2M hydrochloric acid (10 ml) and extracted with ethyl acetate (2×25 ml). The aqueous layer was basified to pH 10 with 2M sodium hydroxide and re-extracted with ethyl acetate (2×25 ml). All of the organic extracts were combined, washed with brine and dried (MgSO$_4$). Volatile material was removed by evaporation and the residue was purified by gradient elution with 35–50% ethyl acetate/hexane through a silica gel Mega Bond Elut column to give N-isobutoxycarbonyl-N-(3-methoxy-5-methylpyrazin-2-yl)-2-[4-(isopropylamino)phenyl]pyridine-3-sulphonamide (0.11 g) as a gum; $^1$H NMR (d$_6$-DMSO): 0.6 (d, 6H), 1.2 (d, 6H), 1.6 (m, 1H), 3.6 (m, 1H), 3.8 (d, 2H), 4.0 (s, 3H), 5.8 (d, 1H), 6.6 (d, 2H), 7.35 (d, 2H), 7.6 (m, 1H), 8.2 (s, 1H), 8.8 (m, 2H); mass spectrum (+ve ESP): 514 (M+H)$^+$.

EXAMPLE 25

Using an analogous procedure to that described in Example 5, there was thus obtained (in 29% yield) N-(5-chloro-3-methoxypyrazin-2-yl)-2-(4-methoxycarbonylphenyl)pyridine-3-sulphonamide: $^1$H NMR (CDCl$_3$): 3.8 (s, 3H), 4.0 (s, 3H), 6.7 (br s, 1H), 7.4 (d, 2H), 7.55 (s, 1H), 7.57 (dd, 1H), 8.1 (d, 2H), 8.7 (dd, 1H), 8.65 (dd, 1H); mass spectrum (+ve FAB, DMSO/NBA): 435 (M+H)$^+$; starting from 4-nitrophenyl 2-(4-methoxycarbonylphenyl)pyridine-3-sulphonate; $^1$H NMR (d$_6$-DMSO): 3.8 (s, 3H), 7.3 (d, 2H), 7.7 (d, 2H), 7.75 (dd, 1H), 8.05 (d, 2H), 8.25 (d, 2H), 8.45 (dd, 1H), 9.05 (dd, 1H); mass spectrum (+ve ESP): 414 (M+H)$^+$; itself obtained using an analogous procedure to that described in Example 5, part (ii) but using 4-(methoxycarbonyl)phenylboronic acid.

EXAMPLE 26

Lithium tetrahydridoaluminate (20.5 ml of a 1M solution in ether) was added over 10 minutes to a solution of 2-[4-(2,3-epoxy-2-methylpropyl)phenyl]-N-(isobutoxycarbonyl)-N-(3-methoxy-5-methylpyrazin-2-yl) pyridine-3-sulphonamide (1.8 g) in anhydrous THF at 0° C. After 30 minutes the reaction mixture was poured into saturated aqueous ammonium chloride solution (50 ml) and was extracted with ethyl acetate (4×50 ml). The extracts were washed with brine and dried (MgSO$_4$). Volatile material was removed by evaporation and the residue was purified by gradient elution with 0–80% ethyl acetate/ hexane through a silica gel Mega Bond Elut column to give 2-[4-(2-hydroxy-2-methylpropyl)phenyl]-N-(3-methoxy-5-methylpyrazin-2-yl)pyridine-3-sulphonamide (0.115 g) as a foam; $^1$H NMR (CDCl$_3$+CD$_3$COOD): 1.3 (s, 6H), 2.3 (s, 3H), 2.8 (s, 2H), 3.8 (s, 3H), 7.2–7.3 (m, 5H), 7.55 (dd, 1H), 8.7 (dd, 1H), 8.85 (dd, 1H); mass spectrum (+ve ESP): 429 (M+H)$^+$.

The starting material 2-[4-(2,3-epoxy-2-methylpropyl)-phenyl]-N-(isobutoxycarbonyl)-N-(3-methoxy-5-methylpyrazin-2-yl)pyridine-3-sulphonamide was obtained as follows:

(i) Using an analogous procedure to that described in Example 11 part (i), but using 1-bromo-4-(2-methylprop-2-enyl)benzene (obtained as described in *Chemische Berichte*, 1962, 95, 1921) and with purification by gradient elution with 0–70% ethyl acetate/hexane through a silica gel ega Bond Elut column, there was thus obtained (in 32% yield) 4-(2-methylprop-2-enyl)phenylboronic acid as a solid, $^1$H NMR (CDCl$_3$): 1.7 (s, 3H), 3.4 (s, 2H), 4.8 (d, 2H), 7.35 (d, 2H), 8.15 (d, 2H); mass spectrum (−ve ESP): 175 (M−H)$^−$.

(ii) Using an analogous procedure to that described in Example 11 part (ii) but using 4-(2-methylprop-2-enyl) phenylboronic acid, there was thus obtained (in 61% yield) N-(isobutoxycarbonyl)-N-(3-methoxy-5-methylpyrazin-2-yl)-2-[4-(2-methylprop-2-enyl)phenyl] pyridine-3-sulphonamide, $^1$H NMR (CDCl$_3$): 0.7 (d, 6H), 1.7 (s, 3H), 1.75 (m, 1H), 2.5 (s, 3H), 3.35 (s, 2H), 3.8 (d, 2H), 4.0 (s, 3H), 4.8 (d, 2H), 7.25 (d, 2H), 7.5 (dd, 1H), 7.6 (d, 2H), 7.9 (s, 1H), 8.85 (dd, 1H), 8.95 (dd, 1H); mass spectrum (+ve ESP): 511 (M+H)$^+$.

(iii) 3-Chloroperoxybenzoic acid (50%, 2.4 g) was added over 5 minutes to a solution of N-(isobutoxycarbonyl)-N-(3-methoxy-5-methylpyrazin-2-yl)-2-[4-(2-methylprop-2-enyl)phenyl]pyridine-3-sulphonamide (1.8 g) in dichloromethane (75 ml) at 0° C. The reaction mixture was allowed to warm to ambient temperature and stirred a further 1 hour. The mixture was washed with saturated aqueous sodium hydrogen carbonate solution (20 ml), water and saturated sodium chloride solution then dried (MgSO$_4$). Volatile material was removed by evaporation and the residue was purified by suction flash chromatography followed by gradient elution with 0–40% ethyl acetate/hexane through a silica gel Mega Bond Elut column to give 2-[4-(2,3-epoxy-2-methylpropyl)phenyl]-N-(isobutoxycarbonyl)-N-(3-methoxy-5-methylpyrazin-2-yl)pyridine-3-sulphonamide (0.16 g) as a solid, $^1$H NMR (CDCl$_3$): 0.65 (d, 6H), 1.3 (s, 3H), 1.7 (m, 1H), 2.5 (s, 3H), 2.65 (dd, 2H), 2.9 (q, 2H), 3.85 (d, 2H), 4.0 (s, 3H), 7.3 (d, 2H), 7.5 (dd, 1H), 7.6 (d, 2H), 7.95 (s, 1H), 8.85 (dd, 1H), 8.95 (dd, 1H); mass spectrum (+ve ESP): 527 (M+H)$^+$.

EXAMPLE 27

Using an analogous procedure to that described in Example 1, but starting from N-(isobutoxycarbonyl)-N-(3-methoxy-5-methylpyrazin-2-yl)-2-(4-methylphenyl) pyridine-3-sulphonamide, there was thus obtained (in 35% yield) N-(3-methoxy-5-methylpyrazin-2-yl)-2-(4-methylphenyl)pyridine-3-sulphonamide, m.p. 184–185° C.; microanalysis found: C, 58.0; H, 4.9; N, 14.9%; $C_{18}H_{18}N_4O_3S$ requires: C, 58.4; H, 4.9; N, 15.1%.

The starting material N-(isobutoxycarbonyl)-N-(3-methoxy-5-methylpyrazin-2-yl)-2-(4-methylphenyl)pyridine-3-sulphonamide, m.p. 143–145° C., was obtained in 72% yield using an analogous procedure to that described in Example 1, part (iii), but starting from 4-methylphenylboronic acid.

EXAMPLE 28

Oil-free sodium hydride (240 mg) was added to methanol (20 ml) with stirring. When evolution of hydrogen ceased, 2-(4-bromomethylphenyl)-N-(isobutoxycarbonyl)-N-(3-methoxy-5-methylpyrazin-2-yl)pyridine-3-sulphonamide (549 mg) was added and the mixture was stirred for 2 hours. Volatile material was removed by evaporation and saturated ammonium chloride solution (10 ml) was added to the residue. The mixture was extracted with ethyl acetate (3×20 ml) and the extracts were dried (MgSO$_4$). Volatile material was removed by evaporation and the residue was purified by flash chromatography, eluting with ethyl acetate/hexane (13:7 v/v), to give 2-(4-methoxymethylphenyl)-N-(3-methoxy-5-methylpyrazin-2-yl)pyridine-3-sulphonamide (170 mg), m.p. 129–130° C. (after trituration with ether); microanalysis found: C, 56.9; H, 4.9; N, 13.9%; $C_{19}H_{20}N_4O_4S$ requires: C, 57.0; H, 5.0; N, 14.0%.

The starting material 2-(4-bromomethylphenyl)-N-(isobutoxycarbonyl)-N-(3-methoxy-5-methylpyrazin-2-yl)pyridine-3-sulphonamide was obtained as follows:

N-Bromosuccinimide (2.99 g) and azobisisobutyronitrile (275 mg) were added to a solution of N-(isobutoxycarbonyl)-N-(3-methoxy-5-methylpyrazin-2-yl)-2-(4-methylphenyl)pyridine-3-sulphonamide (7.9 g) in carbon tetrachloride (150 ml) and the mixture was heated under reflux for 4 hours. Insoluble material was removed by filtration and the fitrate was concentrated by evaporation. The residue was redissolved in ethyl acetate (200 ml) and the solution was washed with water (100 ml) and saturated sodium chloride solution (100 ml). The solution was dried (MgSO$_4$) and the solvent was removed by evaporation. The residue was triturated with ethyl acetate/hexane (3:7 v/v, 80 ml) to give 2-(4-bromomethylphenyl)-N-(isobutoxycarbonyl)-N-(3-methoxy-5-methylpyrazin-2-yl)-pyridine-3-sulphonamide (6.5 g), m.p. 125–128° C.

EXAMPLE 29

Using an analogous procedure to that described in Example 28, but using isopropanol as solvent, there was thus obtained (in 39% yield) 2-(4-isopropoxymethylphenyl)-N-(3-methoxy-5-methylpyrazin-2-yl)pyridine-3-sulphonamide, m.p. 123–124° C.; $^1$H NMR (DMSO-d$_6$): 1.2 (d, 6H), 2.25 (s, 3H), 3.65–3.75 (m, 1H), 3.85 (s, 3H), 4.5 (s, 2H), 7.25–7.5 (m, 5H), 7.6 (dd, 1H), 8.45 (dd, 1H). 8.8 (dd, 1H).

EXAMPLE 30

A solution of N-(isobutoxycarbonyl)-2-(4-methoxycarbonylphenyl)-N-(3-methoxy-5-methylpyrazin-2-yl)pyridine-3-sulphonamide (830 mg) and sodium methoxide (433 mg) in methanol (25 ml) was heated under reflux for 1 hour. Volatile material was removed by evaporation and saturated ammonium chloride solution (20 ml) was added to the residue. The mixture was extracted with ethyl acetate (2×20 ml) and the extracts were washed with water (2×15 ml) and dried (MgSO$_4$). The solvent was removed by evaporation and the residue was purified by flash chromatography, eluting with 25–50% ethyl acetate/hexane, to give 2-(4-methoxycarbonylphenyl)-N-(3-methoxy-5-methylpyrazin-2-yl)pyridine-3-sulphonamide (190 mg), m.p. 144–146° C.; microanalysis found: C, 55.2; H, 4.3; N, 13.3%; $C_{23}H_{24}BrN_4O_4S$ requires: C, 55.1; H, 4.4; N, 13.5%.

The starting material N-(isobutoxycarbonyl)-2-(4-methoxycarbonylphenyl)-N-(3-methoxy-5-methylpyrazin-2-yl)pyridine-3-sulphonamide was obtained as follows:

(i) A solution of 4-carboxyphenylboronic acid (25 g) and concentrated sulphuric acid (1 ml) in methanol (250 ml) was heated under reflux for 36 hours. Volatile material was removed by evaporation and the residue was dissolved in ethyl acetate (200 ml). Water (100 ml) was added and the mixture was stirred for 1 hour. The organic phase was separated and washed with saturated sodium bicarbonate solution (50 ml), water (100 ml) and saturated sodium chloride solution (50 ml). The solution was dried (MgSO$_4$) and the solvent was removed by evaporation to give 4-methoxycarbonylphenylboronic acid (27.7 g), m.p. 227–229° C.

(ii) A solution of potassium fluoride (7.0 g) in water (150 ml) was added to a solution of 2-chloro-N-isobutoxycarbonyl-N-(3-methoxy-5-methylpyrazin-2-yl)pyridine-3-sulphonamide (8.3 g), 4-methoxycarbonylphenylboronic acid (7.9 g) and tetrakis(triphenylphosphine)palladium(0) (1.0 g) in toluene (150 ml) and the mixture was heated under reflux under argon for 18 hours. Ethyl acetate (150 ml) was added and the organic phase was separated. The solution was washed with 2M sodium hydroxide solution (100 ml) and water (250 ml) and then dried (MgSO$_4$). Volatile material was removed by evaporation and the residue was triturated with ethyl acetate/hexane (1:3 v/v) to give N-(isobutoxycarbonyl)-2-(4-methoxycarbonylphenyl)-N-(3-methoxy-5-methylpyrazin-2-yl)pyridine-3-sulphonamide (8.5 g), m.p. 134–136° C.

EXAMPLES 31–32

By an analogous procedure to that described in Example 5 but using the appropriate aminoheterocycle of formula VII the following compounds were obtained in yields of 23–27%:

EXAMPLE 31

N-(5-bromo-3-methoxypyrazin-2-yl)-2-(4-isobutylphenyl)pyridine-3-sulphonamide microanalysis found: C, 50.0; H, 4.4; N, 11.5%; $C_{20}H_{21}BrN_4O_3S$ requires: C, 50.3; H, 4.4; N, 11.7%; $^1$H NMR (CDCl$_3$): 0.95 (d, 6H), 1.9 (m, 1H), 2.5 (d, 2H), 3.8 (s, 3H), 6.65 (br s, 1H), 7.2 (d, 2H), 7.3 (d, 2H), 7.5 (dd, 1H), 7.6 (s, 1H), 8.6 (dd, 1H), 8.8 (dd, 1H); starting from 2-amino-5-bromo-3-methoxypyrazine (obtained as described in *Gazz. Chem. Ital.* 1960, 90, 1807).

EXAMPLE 32

N-(2-chloro-4-methoxypyrimidin-5-yl)-2-(4-isobutylphenyl)pyridine-3-sulphonamide $^1$H NMR (CDCl$_3$): 0.95 (d, 6H), 1.9 (m, 1H), 2.5 (d, 2H), 3.8 (s, 3H), 6.15 (s, 1H), 7.25 (d, 2H), 7.4–7.5 (m, 3H), 8.1 (s, 1H), 8.5 (dd, 1), 8.85 (dd, 1H); mass spectrum (+ve ESP): 433 (M+H)$^+$; starting from 5-amino-2-chloro-4-methoxypyrimidine, itself obtained as follows:

A mixture of 5-amino-2,4-dichloropyrimidine (0.32 g) (obtained as described in *Chem. Pharm. Bull.*, (JAPAN), 1958, 6, 343–346) and a solution of sodium methoxide in methanol (from sodium (0.05 g) and methanol (25 ml)) was heated at reflux for 15 minutes and allowed to cool. Volatile material was removed by evaporation and a small volume of water added. The mixture was extracted twice with ether and the combined extracts were dried (MgSO$_4$) and evaporated to give 5-amino-2-chloro-4-methoxypyrimidine (0.2 g) as an oil; $^1$H NMR (d$_6$-DMSO): 3.92 (s, 3H), 5.25 (s, 2H), 7.72 (s, 1H); mass spectrum (+ve CI): 160 (M+H)$^+$.

EXAMPLE 33

Tetrakis(triphenylphosphine)palladium (0) (25 mg) was added to a deoxygenated solution of sodium carbonate (223 mg), dimethoxy-(3-pyridyl)borane (116 mg) and 2-(4-iodophenyl)-N-(3-methoxy-5-methylpyrazin-2-yl)pyridine-3-sulphonamide (828 mg) in a mixture of water (1.8 ml), ethanol (3 ml) and toluene (6 ml). The mixture was stirred and heated under argon at 85° C. for 17 hours and then allowed to cool to ambient temperature. Water was added and the reaction mixture was washed three times with ethyl acetate. The aqueous layer was acidified to pH 7 with 2M hydrochloric acid and extracted six times with ethyl acetate. These extracts were combined, washed with saturated sodium chloride solution then dried (MgSO$_4$). Volatile material was removed by evaporation and the residue was purified by chromatography on a silica gel Mega Bond Elut column, eluting with 0–8% methanol/dichloromethane to give N-(3-methoxy-5-methylpyrazin-2-yl)-2-(4-[3-pyridyl]phenyl)pyridine-3-sulphonamide (123 mg) as a solid; $^1$H NMR (CDCl$_3$): 2.3 (s, 3H), 3.7 (s, 3H), 7.3–7.7 (m, 7H), 7.92 (m, 1H), 8.55–8.75 (m, 2H), 8.8 (dd, 1H), 8.9 (d, 1H); mass spectrum (+ve ESP): 434 (M+H)$^+$.

The starting material 2-(4-iodophenyl)-N-(3-methoxy-5-methylpyrazin-2-yl)pyridine-3-sulphonamide was obtained as follows:

(i) Using an analogous procedure to that described in Example 11, part (i), except that 1-bromo-4-(trimethylsilyl)benzene (prepared as described in *J. Am. Chem. Soc.*, 1994, 116, 11723) was used as starting material, there was thus obtained (in 58% yield) 4-trimethylsilylphenylboronic acid as a solid, mass spectrum (–ve ESP): 193 (M–H)$^-$.

(ii) Using an analogous procedure to that described in Example 11, part (ii), except that 4-trimethylsilylphenylboronic acid was used as starting material and the crude product was purified by trituration with 20% ethyl acetate/isohexane, there was thus obtained (in 81% yield) N-(isobutoxycarbonyl)-N-(3-methoxy-5-methylpyrazin-2-yl)-2-(4-trimethylsilylphenyl)pyridine-3-sulphonamide as a solid, m.p. 132–134° C.; mass spectrum (+ve ESP): 529 (M+H)$^+$.

(iii) N-Iodosuccinimide (0.84 g) was added to a solution of N-(isobutoxycarbonyl)-N-(3-methoxy-5-methylpyrazin-2-yl)-2-(4-trimethylsilylphenyl)pyridine-3-sulphonamide (1.58 g) in acetonitrile (15 ml) and the reaction mixture was stirred and heated at 65° C. for 17 hours. A further portion of N-iodosuccinimide (50 mg) was added and heating continued for 24 hours, then more N-iodosuccinimide (100 mg) was added and heating continued a further 24 hours. The mixture was cooled and volatile material was removed by evaporation. The residue was purified by chromatography on a silica gel Mega Bond Elut column, eluting with 0–25% ethyl acetate/hexane, followed by trituration with hexane (2×25 ml) to give 2-(4-iodophenyl)-N-isobutoxycarbonyl-N-(3-methoxy-5-methylpyrazin-2-yl)pyridine-3-sulphonamide as a solid, m.p. 156–158° C.; $^1$H NMR (CDCl$_3$): 0.7 (d, 6H), 1.7 (m, 1H), 2.5 (s, 3H), 3.8 (d, 2H), 4.0 (s, 3H), 7.4 (d, 2H), 7.5 (dd, 1H), 7.7 (d, 2H), 7.9 (s, 1H), 8.8 (dd, 1H), 8.0 (dd, 1H); mass spectrum (+ve ESP): 583 (M+H)$^+$.

(iv) Using an analogous procedure to that described in Example 9, except that 2-(4-iodophenyl)-N-isobutoxycarbonyl-N-(3-methoxy-5-methylpyrazin-2-yl)pyridine-3-sulphonamide was used as starting material and the crude product was purified by trituration with ethyl acetate, there was thus obtained (in 72% yield) 2-(4-iodophenyl)-N-(3-methoxy-5-methylpyrazin-2-yl)pyridine-3-sulphonamide as a solid, m.p. 180–183° C.; $^1$H NMR (CDCl$_3$): 2.3 (s, 3H), 3.9 (s, 3H), 6.7 (br s, 1H), 7.1 (d, 2H), 7.3 (br s, 1H), 7.5 (dd, 1H), 7.7 (br d, 2H), 8.7 (br d, 1H), 8.8 (d, 1H).

Dimethoxy-(3-pyridyl)borane was prepared as follows:

n-Butyl lithium (31.3 ml of a 1.6M solution in hexane) was added to a stirred solution of 3-bromopyridine (4.8 ml) and trimethyl borate (6.2 ml) in dry THF (100 ml) at a rate such that the temperature did not exceed –65° C. The mixture was allowed to warm to ambient temperature over 16 hours and was filtered. The solid was washed with ether, combined with more solid obtained from the filtrate and rewashed with ether to give dimethoxy-(3-pyridyl)borane (3.5 g) as a solid, $^1$H NMR (CD$_3$OD): 3.4 (s, 6H), 7.2 (m, 1H), 7.9 (m, 1H), 8.2 (dd, 1H), 8.6 (s, 1H); mass spectrum (+ve CI): 152 (M+H)$^+$.

EXAMPLE 34

Using an analogous procedure to that described in Example 33 but using dimethoxy-(4-pyridyl)borane as starting material, there was thus obtained (in 28% yield) N-(3-methoxy-5-methylpyrazin-2-yl)-2-(4-[4-pyridyl]phenyl)pyridine-3-sulphonamide as a solid, m.p. 218–220° C. (decomp.); $^1$H NMR (DMSO-d$_6$): 2.1 (s, 3H), 3.8 (s, 3H), 7.3 (br s, 1H), 7.5–7.7 (m, 4H), 7.7–7.9 (m, 4H), 8.45 (dd, 1H), 8.7 (d, 2H) 8.8 (dd, 1H); mass spectrum (+ve ESP): 434 (M+H)$^+$.

The starting material dimethoxy-(4-pyridyl)borane was obtained as follows:

Anhydrous potassium carbonate (7.6 g) was added to a solution of 4-bromopyridine hydrochloride (9.73 g) in water (50 ml). The mixture was extracted with ether (100 ml) and dried (MgSO$_4$). Volatile material was removed by evaporation and the residue was then redissolved in anhydrous ether (100 ml). The resultant solution was cooled to –100° C. under argon and treated dropwise with n-butyl lithium (31.3 ml of a 1.6M solution in hexane) keeping the temperature below –90° C. Trimethyl borate (6.2 ml) was added and the mixture was stirred for 16 hours whilst warming to –40° C. The resultant precipitate was collected, washed with ether containing a few drops of ethereal hydrochloric acid and dried in vacuo to give dimethoxy-(4-pyridyl)borane as a solid (6.2 g), mass spectrum (+ve CI): 152 (M+H)$^+$.

EXAMPLE 35

Using an analogous procedure to that described in Example 9, except that N-isobutoxycarbonyl-N-(3-methoxy-5-methylpyrazin-2-yl)-2-(4-[2-pyridyl]phenyl)pyridine-3-sulphonamide was used as starting material and the product was purified by chromatography on a silica gel Mega Bond Elut column, eluting with 0–10% methanol/dichloromethane, there was thus obtained (in 76% yield) N-(3-methoxy-5-methylpyrazin-2-yl)-2-(4-[2-pyridyl]phenyl)pyridine-3-sulphonamide as a solid; $^1$H NMR (CDCl$_3$): 2.3 (br s, 3H), 3.6 (br s, 3H), 6.7 (br s, 1H), 7.2–7.6 (m, 4H), 7.7 (dd, 1H), 7.8 (d, 2H), 8.05 (m, 2H), 8.6–8.9 (m, 2H), 8.8 (br d, 1H); mass spectrum (+ve ESP): 434 (M+H)$^+$.

The starting material N-isobutoxycarbonyl-N-(3-methoxy-5-methylpyrazin-2-yl)-2-(4-[2-pyridyl]phenyl) pyridine-3-sulphonamide was obtained as follows:

Tetrakis(triphenylphosphine)palladium (0) (45 mg) was added to a deoxygenated solution of (2-pyridyl) tributylstannane (294 mg) and N-isobutoxycarbonyl-N-(3-methoxy-5-methylpyrazin-2-yl)-2-(4-iodophenyl)pyridine-3-sulphonamide(465-mg) in xylene (15 ml). The mixture was stirred and heated under argon at 125° C. for 17 hours and then allowed to cool to ambient temperature. Water was added and the mixture was extracted with ethyl acetate. The organic layers were combined, washed with saturated sodium chloride solution then dried (MgSO$_4$). Volatile material was removed by evaporation and the residue was purified by chromatography on a silica gel Mega Bond Elut column, eluting with 0–65% ethyl acetate/hexane to give N-isobutoxycarbonyl-N-(3-methoxy-5-methylpyrazin-2-yl)-2-(4-(2-pyridyl)phenyl)pyridine-3-sulphonamide (135 mg) as a foam; $^1$H NMR (CDCl$_3$): 0.7 (d, 6H), 1.7 (m, 1H), 2.5 (s, 3H), 3.8 (d, 2H), 4.0 (s, 3H), 7.5 (dd, 2H), 7.6–7.8 (m, 4H), 7.9 (s, 1H), 8.1 (dd, 2H), 8.7 (dd, 1H), 8.9 (dd, 1H), 9.0 (dd, 1H); mass spectrum (+ve ESP): 534 (M+H)$^+$.

EXAMPLE 36

Hydrazine hydrate (1.2 ml) was added to a solution of N-(isobutoxycarbonyl)-2-(4-methoxycarbonylphenyl)-N-(3-methoxy-5-methylpyrazin-2-yl)pyridine-3-sulphonamide (1.54 g) in methanol (15 ml) and the mixture was heated and stirred under reflux for 24 hours then cooled. The solid was collected and dried under reduced pressure to give the free sulphonamido-acylhydrazide (0.857 g); $^1$H NMR (d$_6$-DMSO): 2.2 (s, 3H), 3.7 (s, 3H), 6.7 (br s, 2H), 7.3 (s, 1H), 7.5 (m, 3H), 7.8 (d, 2H), 8.4 (d, 1H), 8.75 (dd, 1H), 9.8 (br s, 1H). A solution of this acylhydrazide (207 mg) in triethylorthoformate (5 ml) was heated under reflux for 17 hours then cooled. The resultant solid was collected and purified by chromatography on a silica gel Mega Bond Elut column, eluting with 0–10% methanol/dichloromethane to give N-(3-methoxy-5-methylpyrazin-2-yl)-2-(4-[1,3,4-oxadiazol-2-yl]phenyl)pyridine-3-sulphonamide (39 mg) as a solid; $^1$H NMR (DMSO-d$_6$): 2.2 (br s, 3H), 3.8 (s, 3H), 7.4 (br s, 1H), 7.6–7.8 (m, 3H), 8.0 (m, 2H), 8.5 (dd, 1H), 8.9 (dd, 1H), 9.4 (s, 1H); mass spectrum (+ve ESP): 425 (M+H)$^+$.

EXAMPLE 37 n-Butyl lithium (1.63 ml of a 1.6M solution in pentane) was added to a stirred solution of acetone oxime (95 mg) in dry THF (5 ml) at 0° C. After 1 hour a solution of 2-(4-methoxycarbonylphenyl)-N-(3-methoxy-5-methylpyrazin-2-yl)pyridine-3-sulphonamide (414 mg) in THF (5 ml) was added. The solution was allowed to warm up over 17 hours. The mixture was poured into a stirred solution of concentrated sulphuric acid (0.6 g) in THF (2.8 ml) and water (0.7 ml) and heated under reflux for 1 hour. The cooled solution was treated with saturated sodium carbonate solution to pH 5 then extracted three times with ethyl acetate. The organic extracts were washed with water and saturated sodium chloride solution then dried (MgSO$_4$). Volatile material was removed by evaporation and the residue was purified by chromatography on a silica gel Mega Bond Elut column, eluting with 0–45% ethyl acetate/hexane to give N-(3-methoxy-5-methylpyrazin-2-yl)-2-(4-[3-methylisoxazol-5-yl]phenyl)pyridine-3-sulphonamide (37 mg) as a solid; $^1$H NMR (DMSO-d$_6$ at 373K); 2.2 (s, 3H), 2.3 (s, 3H), 3.8 (s, 3H), 6.7 (s, 1H), 7.4 (br s, 1H), 7.5–7.7 (m, 4H), 7.8 (d, 2H), 8.5 (dd, 1H), 8.8 (dd, 1H); mass spectrum (+ve ESP): 438 (M+H)$^+$.

EXAMPLE 38

Sodium hydride (60% dispersion in oil; 132 mg) was washed with hexane and suspended in dry THF (5 ml). 4A Molecular sieves (250 mg) were added, followed by acetamide oxime hydrochloride (133 mg) and the mixture was stirred and heated at 60° C. for 1 hour. A solution of 2-(4-methoxycarbonylphenyl)-N-(3-methoxy-5-methylpyrazin-2-yl)pyridine-3-sulphonamide (414 mg) in dry THF (2 ml) was added and heating was continued for a further 2 hours. The resultant mixture was cooled, filtered and concentrated by evaporation. The residue was treated with water and extracted three times with ethyl acetate. The organic extracts were washed with water and saturated sodium chloride solution and then dried (MgSO$_4$). Volatile material was removed by evaporation and the residue was purified by chromatography on a silica gel Mega Bond Elut column, eluting with 0–35% ethyl acetate/hexane to give N-(3-methoxy-5-methylpyrazin-2-yl)-2-(4–13-methyl-1,2,4-oxadiazol-5-yl]phenyl)pyridine-3-sulphonamide (115 mg) as a solid; $^1$H NMR (CDCl$_3$): 2.3 (br s, 3H), 2.5 (s, 3H), 3.8 (s, 3H), 6.7 (br s, 1H), 7.4 (br s, 1H), 7.4–7.7 (m, 3H), 8.2 (br d, 2H), 8.7 (br d, 1H), 8.8 (dd, 1H); mass spectrum (+ve ESP): 439 (M+H)$^+$.

EXAMPLE 39

A mixture of 2-(4-cyanophenyl)-N-isobutoxycarbonyl-N-(3-methoxy-5-methylpyrazin-2-yl)pyridine-3-sulphonamide (1.96 g), hydroxylamine hydrochloride (0.849 g) and anhydrous potassium carbonate (2.2 g) in ethanol (40 ml) was heated under reflux with stirring for 18 hours then cooled and filtered. The filtrate was concentrated by evaporation and purified by chromatography on a 20 g silica gel Mega Bond Elut column, eluting with 0–8% methanol/dichloromethane to give the free sulphonamido-N-hydroxyamidine (1.3 g) as a foam; $^1$H NMR (CDCl$_3$): 2.3 (s, 3H), 3.8 (s, 3H), 4.9 (br s, 2H), 7.2 (br s, 1H), 7.4 (dd, 2H), 7.45–7.6 (m, 2H), 7.6 (d, 2H), 8.7 (dd, 1H), 8.8 (dd, 1H); mass spectrum (+ve ESP): 415 (M+H)$^+$. A mixture of this hydroxyamidine (1.3 g) and triethylorthoformate (20 ml) was stirred and heated under reflux for 7 hours then cooled. Volatile material was removed by evaporation and the residue was purified by chromatography on a silica gel Mega Bond Elut column, eluting with 0–50% ethyl acetate/dichloromethane to give N-(3-methoxy-5-methylpyrazin-2-yl)-2-(4-[1,2,4-oxadiazol-3-yl]phenyl)pyridine-3-sulphonamide (405 mg) as a solid, m.p. 179–180.5° C.; $^1$H NMR (CDCl$_3$): 2.3 (s, 3H), 3.7 (s, 3H), 6.7 (br s, 1H; exch. with CD$_3$COOD), 7.4 (br s, 1H), 7.45–7.7 (m, 3H), 8.2 (br d, 2H), 8.7 (br d, 1H), 8.8 (m, 2H); mass spectrum (+ve ESP): 425 (M+H)$^+$.

The starting material 2-(4-cyanophenyl)-N-isobutoxycarbonyl-N-(3-methoxy-5-methylpyrazin-2-yl) pyridine-3-sulphonamide was obtained as follows:

A stirred mixture of 1,1'-bis(diphenylphosphino)ferrocene (0.532 g) and palladium (II) acetate (0.162 g) in deoxygenated toluene (95 ml) was heated at 50° C. under argon for 30 minutes then cooled to ambient temperature. 2-Chloro-N-(isobutoxycarbonyl)-N-(3-methoxy-5-methylpyrazin-2-yl) pyridine-3-sulphonamide (10 g), 4-cyanophenylboronic acid (8.47 g), potassium fluoride (8.37 g) and water (95 ml) were added and the resultant mixture was stirred and heated under reflux for 8 hours then cooled. Water (100 ml) was added and the mixture was extracted with ethyl acetate (100 ml) then filtered through diatomaceous earth. The aqueous layer was separated and extracted further with ethyl acetate (2×100 ml). The organic extracts were combined, washed with aqueous sodium carbonate (100 ml of a 2M solution) and water (100 ml) then treated with charcoal and dried (MgSO$_4$). Volatile material was removed by evaporation and the residue was recrystallised from ether/isohexane to give 2-(4-cyanophenyl)-N-isobutoxycarbonyl-N-(3-methoxy-5-methylpyrazin-2-yl)pyridine-3-sulphonamide (9.58 g) as a solid, $^1$H NMR (DMSO-d$_6$): 0.6 (d, 6H), 1.6 (m, 1H), 2.6 (s, 3H), 3.8 (d, 2H), 4.0 (s, 3H), 7.7 (d, 2H), 7.9 (m, 3H), 8.2 (s, 1H), 8.9 (d, 1H),9.0 (d, 1H); mass spectrum (+ve ESP): 482 (M+H)$^+$.

EXAMPLE 40

A solution of the hydroxyamidine intermediate of the preceeding example (173 mg, prepared from 2-(4-cyanophenyl)-N-isobutoxycarbonyl-N-(3-methoxy-5-methylpyrazin-2-yl)pyridine-3-sulphonamide, 288 mg) in pyridine (2 ml) was treated with acetyl chloride (0.034 ml) and heated at 60° C. for 3 hrs. The mixture was cooled, dihlted with water and extracted three times with ethyl acetate. The organic extracts were washed with water and saturated sodium chloride solution then dried (MgSO$_4$). Volatile material was removed by evaporation and the residue was purified by chromatography on a silica gel Mega Bond Elut column, eluting with 0–10% methanol/dichloromethane to give a gum (104 mg); mass spectrum (+ve ESP): 457 (M+H)$^+$. This gum (95 mg) was redissolved in pyridine (3 ml) and heated under reflux under argon for 4 hours. The mixture was cooled, diluted with water and extracted three times with ethyl acetate. Volatile material was removed by evaporation and the residue was purified by chromatography on a silica gel Mega Bond Elut column, eluting with 0–60% ethyl acetate/hexane to give N-(3-methoxy-5-methylpyrazin-2-yl)-2-(4-[5-methyl-1,2,4-oxadiazol-3-yl]phenyl)pyridine-3-sulphonamide (56 mg) as a solid; $^1$H NMR (CDCl$_3$): 2.3 (s, 3H), 2.7 (s, 3H), 3.7 (s, 3H), 6.7 (br s, 1H), 7.3–7.6 (m, 4H), 8.1 (br d, 2H), 8.7 (br d, 1H), 8.8 (br d, 1H); mass spectrum (+ve ESP): 439 (M+H)$^+$.

EXAMPLE 41

Using an analogous procedure to that described in Example 9, but using N-isobutoxycarbonyl-N-(3-methoxy-5-methylpyrazin-2-yl)-2-(4-[pyrimidin-2-yl]phenyl) pyridine-3-sulphonamide as starting material, there was thus obtained (in 40% yield) N-(3-methoxy-5-methylpyrazin-2-yl)-2-(4-[pyrimidin-2-yl]phenyl)pyridine-3-sulphonamide as a solid; $^1$H NMR (d$_6$-DMSO): 2.2 (br s, 3H), 3.8 (s, 3H), 7.4 (t, 1H), 7.5– 7.6 (br m, 3H), 7.65 (dd, 1H), 8.4 (br s, 2H), 8.5 (dd, 1H), 8.8 (dd, 1H), 8.9 (d, 2H), 10.5 (br s, 1H); mass spectrum (+ve ESP): 435 (M+H)$^+$.

The starting material N-isobutoxycarbonyl-N-(3-methoxy-5-methylpyrazin-2-yl)-2-(4-[pyrimidin-2-yl] phenyl)pyridine-3-sulphonamide was obtained as follows:

Tetrakis(triphenylphosphine)palladium (0) (60 mg) was added to a deoxygenated solution of sodium carbonate (233 mg), 1,4-benzenediboronic acid (165 mg), 2-chloropyrimidine (114.5 mg) and 2-chloro-N-(isobutoxycarbonyl)-N-(3-methoxy-5-methylpyrazin-2-yl) pyridine-3-sulphonamide (414 mg) in a mixture of water (1.6 ml), ethanol (4 ml) and toluene (8 ml). The mixture was stirred and heated under argon under reflux for 16 hours and then allowed to cool to ambient temperature. Water (15 ml) was added and the mixture was extracted with ethyl acetate (2×20 ml). The combined organic layers were washed with saturated sodium chloride solution and dried (MgSO$_4$). Volatile material was removed by evaporation and the residue was purified by chromatography on a silica gel Mega Bond Elut column, eluting with 25–100% ethyl acetate/hexane to give N-isobutoxycarbonyl-N-(3-methoxy-5-methylpyrazin-2-yl)-2-(4-[pyrimidin-2-yl]phenyl)pyridine-3-sulphonamide (95 mg) as a solid, mass spectrum (+ve ESP): 535 (M+H)$^+$.

EXAMPLE 42

Oil-free sodium hydride (240 mg) was added to a stirred solution of 3-pyridyl carbinol (1.09 g) in dry THF (20 ml). When evolution of hydrogen ceased, 2-(4-bromomethylphenyl)-N-(isobutoxycarbonyl)-N-(3-methoxy-5-methylpyrazin-2-yl)pyridine-3-sulphonamide (549 mg) was added and the mixture was stirred for 2 hours. Volatile material was removed by evaporation and saturated ammonium chloride solution (10 ml) was added to the residue. The mixture was extracted with ethyl acetate (3×20 ml) and the extracts were dried (MgSO$_4$). Volatile material was removed by evaporation and the residue was purified by flash chromatography, eluting with methanol/ethyl acetate (1:19 v/v), to give after trituration with ether N-(3-methoxy-5-methylpyrazin-2-yl)-2-{4-[(3-pyridyl)methoxymethyl] phenyl}pyridine-3-sulphonamide (187 mg), m.p. 183–185° C.; microanalysis found: C, 60.9; H, 4.9; N, 14.2%; C$_{24}$H$_{23}$N$_5$O$_4$S requires: C, 60.4; H, 4.85; N, 14.7%.

EXAMPLE 43

Using an analogous procedure to that described in Example 42, but using allyl alcohol as starting material, there was thus obtained (in 38% yield) 2-[4-(allyloxymethyl)phenyl]-N-(3-methoxy-5-methylpyrazin-2-yl)pyridine-3-sulphonamide, m.p. 72–76° C.; microanalysis found: C, 59.1; H, 5.3; N, 13.2%; C$_{21}$H$_{22}$N$_4$O$_4$S requires: C, 59.1; H, 5.2; N, 13.1%.

EXAMPLE 44

Using an analogous procedure to that described in Example 42, but using methyl 2-hydroxy-2-methylpropionate as starting material, there was thus obtained (in 30% yield) 2-[4-([(1-methoxycarbonyl-1methyl)ethoxylmethyl]phenyl]-N-(3-methoxy-5-methylpyrazin-2-yl)pyridine-3-sulphonamide, m.p. 125–127° C.; microanalysis found: C, 56.8; H, 5.6; N, 11.4%; C$_{23}$H$_{26}$N$_4$O$_6$S requires: C, 56.8; H, 5.4; N, 11.5%.

EXAMPLE 45

A solution of lithium hydroxide (150 mg) in water (2 ml) was added to a solution of 2-[4-([(1-methoxycarbonyl-1-methyl)ethoxy]methyl]phenyl]-N-(3-methoxy-5-methylpyrazin-2-yl)pyridine-3-sulphonamide (340 mg) in THF (8 ml) and methanol (2 ml) and the solution was stirred for 20 hours. Volatile material was removed by evaporation and the residue was dissolved in water (25 ml). The solution was washed with ethyl acetate (2×25 ml) and acidified with 20% aqueous citric acid. The mixture was extracted with ethyl acetate (2×25 ml) and the extracts were re-extracted with saturated sodium bicarbonate solution (2×10 ml). The aqueous solution was acidified with 20% aqueous citric acid and extracted with ethyl acetate (2×25 ml). The extracts were washed with water (10 ml) and saturated sodium chloride solution (50 ml) and dried (MgSO$_4$). Volatile material was removed by evaporation and the residue was triturated with ether to give 2-[4-([(1-carboxy-1-methyl) ethoxy]methyl)phenyl]-N-(3-methoxy-5-methylpyrazin-2-yl)pyridine-3-sulphonamide (255 mg), $^1$H NMR (d$_6$-DMSO): 1.4 (s, 6H), 2.2 (s, 3H), 3.8 (s, 3H), 4.5 (s, 2H), 7.2–7.5 (m, 5H), 7.6 (d, 1H), 8.4 (d, 1H), 8.8 (d, 1H), 10.4 (s, 1H) 12.45 (br s, 1H); mass spectrum (+ve ESP): 473 (M+H)$^+$.

EXAMPLE 46

A 1.0M solution of diborane in tetrahydrofuran (5.6 ml) was added over 10 minutes to a solution of 2-[4-([(1-methoxycarbonyl-1-methyl)ethoxy]methyl)phenyl]-N-(3-methoxy-5-methylpyrazin-2-yl)pyridine-3-sulphonamide (500 mg) in THF (10 ml) at 0° C. The mixture was allowed to warm to room temperature and stirred for 20 hours. Saturated ammonium chloride solution (15 ml) was added and the solution was acidfied to pH 3 with 2M hydrochloric acid. The mixture was extracted with ether (2×20 ml) and the extracts were dried (MgSO$_4$) and concentrated. The residue was purified by elution with ethyl acetate through a silica gel Mega Bond Elut column followed by recystallisation from ether to give 2-[4-([(2-hydroxy-1,1-dimethyl) ethoxylmethyl)phenyl]-N-(3-methoxy-5-methylpyrazin-2-yl)pyridine-3-sulphonamide (60 mg), m.p. 72–73° C.; microanalysis found: C, 57.1; H, 6.1; N, 11.9%; C$_{22}$H$_{26}$N$_4$O$_5$S requires: C, 57.1; H, 5.7; N, 12.2%.

EXAMPLE 47

Using an analogous procedure to that described in Example 45, but starting from N-isobutoxycarbonyl-2-{4-[(4-methoxycarbonylphenyl)methoxy]phenyl}-N-(3-methoxy-5-methylpyrazin-2-yl)pyridine-3-sulphonamide there was thus obtained (in 71% yield) 2-{4-[(4-carboxyphenyl)methoxy]phenyl}-N-(3-methoxy-5-methylpyrazin-2-yl)pyridine-3-sulphonamide, m.p. 204–205° C.; $^1$H NMR (d$_6$-DMSO): 2.25 (s, 3H), 3.8 (s, 3H), 4.5 (s, 2H), 7.0 (d, 1H), 7.5 (d, 2H), 7.5–7.55 (m, 1H), 7.6 (d, 2H), 8.0 (d, 2H), 8.8 (d, 2H), 10.4 (s, 1H), 12.9 (br s, 1H).

The starting material N-(isobutoxycarbonyl)-2-{4-[(4-methoxycarbonylphenyl)methoxy]phenyl}-N-(3-methoxy-5-methylpyrazin-2-yl)pyridine-3-sulphonamide was obtained, using an analogous procedure to that described in Example 8 part (v), in 68% yield, m.p. 134–135° C.; using methyl 4-bromomethylbenzoate in place of methyl 2-bromopropionate.

EXAMPLE 48

Using an analogous procedure to that described in Example 19, but starting from 2-{4-[2-(tert-butyldiphenylsilyloxy)ethoxymethyl]phenyl}-N-(3-methoxy-5-methylpyrazin-2-yl)pyridine-3-sulphonamide, there was thus obtained (in 42% yield) 2-{4-[(2-hydroxyethoxy)methyl]phenyl}-N-(3-methoxy-5-methylpyrazin-2-yl)pyridine-3-sulphonamide, m.p. 106–108° C.; microanalysis found: C, 55.3; H, 5.1; N, 12.7%; C$_{20}$H$_{22}$N$_4$O$_5$S requires: C, 55.8; H, 5.15; N, 13.0%.

The starting material 2-{4-[2-(tert-butyldiphenylsilyloxy) ethoxymethyl]phenyl}-N-(3-methoxy-5-methylpyrazin-2-yl)pyridine-3-sulphonamide was obtained, using an analogous procedure to that described in Example 42, in 46% yield; $^1$H NMR (d$_6$-DMSO): 1.0 (s, 9H), 2.25 (s, 3H), 3.6–3.7 (m, 2H), 3.75–3.9 (m, 5H), 4.6 (s, 2H), 7.3–7.5 (m, 6H), 8.45 (dd, 1H), 8.85 (d, 1H), 10.3–10.45 (br s, 1H) 12.9; but using 2-(tert-butyldiphenylsilyloxy)ethanol (obtained as described in J. Org. Chem, (1992), 57, 1707) in place of 3-pyridylcarbinol.

EXAMPLE 49

A solution of 2-{4-[(2-tert-butoxy-1-methylethoxy) methyl]phenyl}-N-(3-methoxy-5-methylpyrazin-2-yl) pyridine-3-sulphonamide (248 mg) in trifluoroacetic acid (1 ml) was left to stand for 30 minutes. Saturated ammonium chloride solution (20 ml) was added and the mixture was extracted with ethyl acetate (2×20 ml). The extracts were dried (MgSO$_4$) and concentrated and the residue was dissolved in dichloromethane (10 ml). The solution was washed with water (2×10 ml) and dried (MgSO$_4$). Volatile material was removed by evaporation and the residue was purified by flash chromatography, eluting with methanol/ethyl acetate (1:24 v/v), to give 2-[4-([2-hydroxy-1-methyl)ethoxy] methyl)phenyl]-N-(3-methoxy-5-methylpyrazin-2-yl) pyridine-3-sulphonamide (82 mg), $^1$H NMR (d$_6$-DMSO): 1.15 (s, 3H), 2.25 (s, 3H), 3.3–3.7 (s, 3H), 3.8 (s, 3H), 4.6 (s, 2H), 7.3–7.55 (m, 5H), 7.6 (dd, 1H), 8.45 (dd, 1H), 8.8 (dd, 1H), 10.35–10.45 (br s, 1H); mass spectrum (+ve ESP): 445 (M+H)$^+$.

The starting material 2-{4-[1-(2-tert-butoxy-1-methylethoxy)methyl]phenyl}-N-(3-methoxy-5-methylpyrazin-2-yl)pyridine-3-sulphonamide was obtained, using an analogous procedure to that described in Example 42, in 57% yield; $^1$H NMR (d$_6$-DMSO): 1.2 (d+s, 12H), 2.3 (s, 3H), 3.3 (dd, 1H), 3.45 (dd, 1H), 3.55–3.65 (m, 1H), 3.8 (s, 3H), 4.6 (br s, 2H), 7.3–7.5 (m, 5H), 7.6 (dd, 1H), 8.4–8.5 (m, 1H), 8.8–8.9 (m, 1H); starting from 1-tert-butoxy-2-propanol in place of 3-pyridyl carbinol.

EXAMPLE 50

Using an analogous procedure to that described in Example 11, but starting from N-(isobutoxycarbonyl)-N-(3-methoxy-5-methylpyrazin-2-yl)-2-[4-morpholinophenyl] pyridine-3-sulphonamide, there was thus obtained (in 55% yield) N-(3-methoxy-5-methylpyrazin-2-yl)-2-[4-morpholinophenyl]pyridine-3-sulphonamide, m.p. 197–198° C.; microanalysis found: C, 56.6; H, 5.3; N, 15.5%; C$_{21}$H$_{23}$N$_5$O$_4$S require: C, 5.71; H, 5.25; N, 15.9%.

The starting material N-(isobutoxycarbonyl)-N-(3-methoxy-5-methylpyrazin-2-yl)-2-[4-morpholinophenyl] pyridine-3-sulphonamide was obtained as follows:
(i) Using an analogous procedure to that described in Example 11 part (i), there was thus obtained (in 90% yield) 4-morpholinophenylboronic acid, $^1$H NMR (CDCl$_3$): 3.2–3.3 (m, 4H), 4.8–4.9 (m, 4H), 7.0 (d, 2H), 8.1 (d, 2H); starting from 4-(4-bromophenyl)morpholine (obtained as described in J. Chem.Soc (C), (1971),132)
(ii) Using an analogous procedure to that described in Example 11 part (ii), but using 4-morpholinophenylboronic acid there was thus obtained (in 56% yield) N-(isobutoxycarbonyl)-N-(3-methoxy-5-methylpyrazin-2-yl)-2-[4-morpholinophenyl]pyridine-3-sulphonamide, $^1$H NMR (CDCl$_3$): 0.7 (d, 6H), 1.5–1.7 (m, 1H), 2.5 (s, 3H), 3.2–3-3 (m, 4H), 3.8–3.9 (m, 4H) 4.0 (s, 3H), 6.95 (d, 2H), 7.4 (dd, 1H), 7.6 (d, 2H), 7.95 (s, 1H), 8.8 (dd, 1H), 8.95 (dd, 1H).

EXAMPLE 51

Using an analogous procedure to that described in Example 11, but staring from 2-(4-neopentylphenyl)-N-(isobutoxycarbonyl)-N-(3-methoxy-5-methylpyrazin-2-yl)

pyridine-3-sulphonamide, there was thus obtained (in 56% yield) 2-(4-neopentylphenyl)-N-(3-methoxy-5-methylpyrazin-2-yl)pyridine-3-sulphonamide, m.p. 159–160° C.; microanalysis found: C, 62.0; H, 6.3; N, 13.0%; $C_{22}H_{26}N_4O_3S$ requires: C, 62.0; H, 6.1; N, 13.1%.

The starting material 2-(4-neopentylphenyl)-N-(isobutoxycarbonyl)-N-(3-methoxy-5-methylpyrazin-2-yl)pyridine-3-sulphonamide was obtained as follows:

(i) Using an analogous procedure to that described in Example 11 part (i), there was thus obtained (in 92% yield) 4-neopentylphenylboronic acid, $^1$H NMR (CDCl$_3$): 0.9 (s, 9H), 2.6 (s, 2H), 7.3 (d, 2H), 8.15 (d, 2H); starting from 1-bromo-4-neopentylbenzene (obtained as described in J. C. S Perkin I, (1982),181).

(ii) Using an analogous procedure to that described in Example 11, part (ii), but starting from 4-neopentylphenylboronic acid, there was obtained (in 59% yield) 2-(4-neopentylphenyl)-N-(isobutoxycarbonyl)-N-(3-methoxy-5-methylpyrazin-2-yl)pyridine-3-sulphonamide, $^1$H NMR (CDCl$_3$): 0.7 (d, 6H), 0.95 (s, 9H), 1.6–1.8 (m, 1H), 2.5 (s, 3H), 3.85 (d, 2H), 4.0 (s, 3H), 7.2 (d, 2H), 7.5 (dd, 1H), 7.55 (d, 2H), 7.95 (s, 1H), 8.85 (dd, 1H), 9.0 (dd, 1H).

EXAMPLE 52

Using an analogous procedure to that described in Example 8, part (iv), but starting from N-(3-methoxy-5-methylpyrazin-2-yl)-2-{4-[2 H-tetrahydropyran-2-yloxy)ethoxy]phenyl}pyridine-3-sulphonamide, there was thus obtained (in 65% yield) 2-[4-(2-hydroxyethoxy)phenyl]-N-(3-methoxy-5-methylpyrazin-2-yl)pyridine-3-sulphonamide, m.p. 180–182° C.; microanalysis found: C, 54.9; H, 5.0; N, 13.2%; $C_{21}H_{23}N_5O_4S$ requires: C, 54.8; H, 4.8; N, 13.5%.

The starting material N-(3-methoxy-5-methylpyrazin-2-yl)-2-{4-[2-(2 H-tetrahydropyran-2-yloxy)ethoxy]phenyl}pyridine-3-sulphonamide was obtained as follows:

(i) Using an analogous procedure to that described in Example 8, part (i), there was thus obtained (in 95% yield) 2-[2-(4-bromophenoxy)ethoxy]-2H-tetrahydropyran, $^1$H NMR (d$_6$-DMSO): 1.4–1.8 (m, 6H), 3.4–3.5 (m, 1H), 3.65–3.85 (m, 2H), 3.9–4.0 (m, 1H), 4.1 (t, 2H), 4.65 (t, 1H), 6.9 (d, 2H), 7.4 (d, 2H); starting from 2-(4-bromophenoxy)ethanol.

(ii) Using an analogous procedure to that described in Example 8, part (ii), but using 2-[2-(4-bromophenoxy)ethoxy]-2H-tetrahydropyran, there was thus obtained (in 51% yield) 4-[2-(2 H-tetrahydropyran-2-yloxy)ethoxy]phenylboronic acid, $^1$H NMR (d$_6$-DMSO): 1.4–1.8 (m, 6H), 3.4–3.5 (m, 1H), 3.65–3.85 (m, 2H), 3.9–4.0 (m, 1H), 4.2 (t, 2H), 4.65 (t, 1H), 6.9 (d, 2H), 7.75 (d, 2H), 7.8 (s, 2H).

(iii) Using an analogous procedure to that described in Example 11 part (ii), but using 4-[2-(2 H-tetrahydropyran-2-yloxy)ethoxy]phenylboronic acid, there was thus obtained (in 42% yield) N-(isobutoxycarbonyl)-N-(3-methoxy-5-methylpyrazin-2-yl)-2-{4-[2-(2 H-tetrahydropyran-2-yloxy)ethoxy]phenyl}pyridine-3-sulphonamide, $^1$H NMR (d$_6$-DMSO): 0.6 (d, 6H), 1.4–1.8 (m, 7H), 2.5 (s, 3H), 3.4–3.5 (m, 1H), 3.7–3.8 (m, 2H), 3.85 (d, 2H) 3.9–4.0 (m, 1H), 4.05 (s, 3H), 4.2 (t, 2H), 4.7 (t, 1H), 7.0 (d, 2H), 7.5 (d, 2H), 7.75 (dd, 1H), 8.15 (s, 1H), 8.85 (d, 1H), 8.9 (d, 1H).

(iv) Using an analogous procedure to that described in Example 45, but using N-(isobutoxycarbonyl)-N-(3-methoxy-5-methylpyrazin-2-yl)-2-{4-[2-(2 H-tetrahydropyran-2-yloxy)ethoxy]phenyl}pyridine-3-sulphonamide there was thus obtained (in 39% yield) N-(3-methoxy-5-methylpyrazin-2-yl)-2-{4-[2-(2 H-tetrahydropyran-2-yloxy)ethoxy]phenyl}pyridine-3-sulphonamide, $^1$H NMR (d$_6$-DMSO): 1.4–1.8 (m, 6H), 2.3 (s, 3H), 3.4–3.5 (m, 1H), 3.65–3.85 (m, 5H), 3.9–4.0 (m, 1H), 4.15 (s, 2H), 4.7 (s, 1H), 6.9 (d, 2H), 7.4 (d, 2H), 7.55–7.6 (m, 2H), 8.4 (d, 1H), 8.8 (d, 1H), 10.3 (s, 1H).

EXAMPLE 53

Using an analogous procedure to that described in Example 45, but starting from 2-[4-(2-hydroxy-2-methylpropoxy)phenyl]-N-(isobutoxycarbonyl)-N-(3-methoxy-5-methylpyrazin-2-yl)pyridine-3-sulphonamide, there was thus obtained (in 49% yield) 2-[4-(2-hydroxy-2-methylpropoxy)phenyl]-N-(3-methoxy-5-methylpyrazin-2-yl)pyridine-3-sulphonamide, m.p. 156–157° C.; microanalysis found: C, 56.7; H, 5.6; N, 12.7%; $C_{21}H_{24}N_4O_5S$ requires: C, 56.7; H, 5.4; N, 12.6%.

The starting material 2-[4-(2-hydroxy-2-methylpropoxy)phenyl]-N-(isobutoxycarbonyl)-N-(3-methoxy-5-methylpyrazin-2-yl)pyridine-3-sulphonamide was obtained as follows:

(i) 3.0M Methyl magnesium iodide in ether (14.0 ml) was added dropwise over 10 minutes to a solution of ethyl 4-bromophenoxyacetate (5.2 g) in ether (50 ml) at 0° C. under argon. The solution was stirred at 0° C. for 1 hour and then saturated ammonium chloride solution (50 ml) was added. The mixture was stirred for 10 minutes and the organic phase was separated. The aqueous phase was further extracted with ether (50 ml) and the organic extracts were combined. The extracts were washed with water (50 ml) and saturated sodium chloride solution (50 ml) and dried (MgSO$_4$). Volatile material was removed by evaporation to give 1-(4-bromophenoxy)-2-methylpropan-2-ol (4.7 g) as an oil, $^1$H NMR (d$_6$-DMSO): 1.2 (s, 6H), 3.7 (s, 2H), 4.55 (s, 1H), 6.9 (d, 2H), 7.4 (d, 2H).

(ii) A solution of 1-(4-bromophenoxy)-2-methylpropan-2-ol (1.23 g) in tetrahydrofuran (25 ml) was added to oil-free sodium hydride (132 mg) under an atmosphere of argon. The mixture was stirred for 30 minutes and then cooled to −78° C. 1.6M Butyl lithium in hexane (6.9 ml) was added over 5 minutes and the solution was stirred at −78° C. for 30 minutes. Trimethylborate (1.14 g) was added over 1 minute and the mixture was stirred at −78° C. for 1 hour. Saturated ammonium chloride solution (25 ml) was added and the mixture was allowed to warm to room temperature. Water (25 ml) was added and the mixture was extracted with ether (2×25 ml). The extracts were washed with water (25 ml) and saturated sodium chloride solution (25 ml) and dried (MgSO$_4$). Volatile material was removed by evaporation and the residue was purified by flash chromatography, eluting with ethyl acetate/hexane (7:3 v/v), to give 4-(2-hydroxy-2-methylpropoxy)phenylboronic acid (355 mg), $^1$H NMR (d$_6$-DMSO): 1.2 (s, 6H), 3.7 (s, 2H), 4.5 (br s, 1H), 6.85 (d, 2H), 7.6–7.8 (m, 4H).

(iii) Using an analogous procedure to that described in Example 11, part (ii), but using 4-(2-hydroxy-2-methylpropoxy)phenylboronic acid, there was thus obtained (in 36% yield) 2-[4-(2-hydroxy-2-methylpropoxy)phenyl]-N-(isobutoxycarbonyl)-N-(3-methoxy-5-methylpyrazin-2-yl)pyridine-3-sulphonamide, $^1$H NMR (d$_6$-DMSO): 0.6 (d, 6H), 1.25 (s, 6H), 1.5–1.7 (m, 1H), 2.55 (s, 3H), 3.75 (s, 2H), 3.8 (d, 2H), 3.95 (s, 3H), 4.6 (s, 1H), 7.0 (d, 2H), 7.5 (d, 2H), 7.75 (dd, 1H), 8.15 (s, 1H), 8.8–8.95 (m, 2H).

EXAMPLE 54

Using an analogous procedure to that described in Example 45, but using 2-[4-(2-hydroxy-1,1-dimethylethoxy)phenyl]-N-(isobutoxycarbonyl)-N-(3-methoxy-5-methylpyrazin-2-yl)pyridine-3-sulphonamide, there was thus obtained (in 49% yield) 2-[4-(2-hydroxy-1,1-dimethylethoxy)phenyl]-N-(3-methoxy-5-methylpyrazin-2-yl)pyridine-3-sulphonamide, m.p. 182–184° C.; $^1$H NMR ($d_6$-DMSO): 1.25 (s, 6H), 2.25 (s, 3H), 3.4 (d, 2H), 3.8 (s, 3H), 4.85 (t, 1H), 6.95 (d, 2H), 7.35 (d, 2H), 7.4–7.5 (m, 1H), 7.55 (dd, 1H), 8.4 (dd, 1H), 8.75 (d, 1H), 10.25–10.5 (br, 1H).

The starting material 2-[4-(2-hydroxy-1,1-dimethylethoxy)phenyl]-N-(isobutoxy carbonyl)-N-(3-methoxy-5-methylpyrazin-2-yl)pyridine-3-sulphonamide was obtained as follows:

(i) Using an analogous procedure to that described in Example 46, but starting from 2-(4-bromophenoxy)-2-methylpropanoic acid, there was obtained (in 87% yield) 2-(4-bromophenoxy)-2-methylpropanol as an oil, $^1$H NMR ($d_6$-DMSO): 1.2 (s, 6H), 3.35 (d, 2H), 4.85 (t, 1H), 7.0 (d, 2H), 7.4 (d, 2H).

(ii) Using an analogous procedure to that described in Example 53, part (ii), but using 2-(4-bromophenoxy)-2-methylpropanol, there was thus obtained (in 23% yield) 4-(2-hydroxy-1,1-dimethylethoxy)phenylboronic acid (355 mg), $^1$H NMR ($d_6$-DMSO): 1.15 (s, 6H), 3.4 (d, 2H), 4.8 (t, 1H), 6.95 (d, 2H), 7.65 (d, 2H), 7.8 (s, 2H).

(iii) Using an analogous procedure to that described in Example 11, part (ii), but using 4-(2-hydroxy-1,1-dimethylethoxy)phenylboronic acid, there was thus obtained (in 40% yield) 2-[4-(2-hydroxy-1,1-dimethylethoxy)phenyl]-N-(isobutoxycarbonyl)-N-(3-methoxy-5-methylpyrazin-2-yl)pyridine-3-sulphonamide, $^1$H NMR ($d_6$-DMSO): 0.6 (d, 6H), 1.25 (s, 6H), 1.5–1.7 (m, 1H), 2.55 (s, 3H), 3.45 (d, 2H), 3.8 (d, 2H), 3.95 (s, 3H), 4.85 (t, 1H), 7.05 (d, 2H), 7.45 (d, 2H), 7.7–7.8 (m, 1H), 8.15 (s, 1H), 8.8–8.95 (m, 2H).

EXAMPLE 55

A 1M solution of acetic acid in dimethoxyethane (5.6 ml) was added dropwise over 3 hours to a mixture of 2-[4-(2-[methoxycarbonyl]vinyl)phenyl]-N-isobutoxycarbonyl-N-(3-methoxy-5-methylpyrazin-2-yl)pyridine-3-sulphonamide (250 mg) and potassium azodicarboxylate (1.4 g) in dry dimethoxyethane (20 ml) at 45° C. The mixture was heated at 45° C. for 18 hours. Insoluble material was removed by filtration and the filtrate was concentrated. The residue was eluted through a pad of silica gel with ethyl acetate/hexane (1:3 v/v) and the resulting solid (230 mg) was dissolved in a mixture of tetrahydrofuran (16 ml) and methanol (4 ml). A solution of lithium hydroxide (118 mg) in water (4 ml) was added and the solution was stirred for 18 hours. Volatile material was removed by evaporation and the residue was dissolved in water (15 ml). The solution was washed with ethyl acetate (2×15 ml) and acidified with 20% aqueous citric acid. The mixture was extracted with ethyl acetate (2×15 ml) and the extracts were washed with water (10 ml) and saturated sodium chloride solution (50 ml) and dried (MgSO$_4$). Volatile material was removed by evaporation and the residue was triturated with ether to give 2-[4-(2-carboxyethyl)phenyl]-N-(3-methoxy-5-methylpyrazin-2-yl)pyridine-3-sulphonamide (42 mg), m.p. 166–168° C.; $^1$H NMR (CDCl$_3$): 2.25 (s, 3H), 2.6 (t, 2H), 3.0 (t, 2H), 3.8 (s, 3H), 7.2–7.3 (m, 5H), 7.45–7.55 (m, 1H), 8.65 (d, 1H), 8.8 (d, 1H), 10.25–10.5 (br, 1H).

The starting material N-isobutoxycarbonyl-2-[4-(2-[methoxycarbonyl]vinyl)phenyl]-N-(3-methoxy-5-methylpyrazin-2-yl)pyridine-3-sulphonamide was obtained as follows:

A solution of 2-(4-iodophenyl)-N-isobutoxycarbonyl-N-(3-methoxy-5-methylpyrazin-2-yl)pyridine-3-sulphonamide (1.5 g), methyl acrylate (0.25 ml), palladium acetate (58 mg) and triethylamine (1.79 ml) in dimethyl formamide (45 ml) and water (5 ml) was heated at 100° C. for 1 hour. Volatile material was removed by evaporation and water (50 ml) was added to the residue. The mixture was acidified to pH 3 with 1M hydrochloric acid and extracted with ethyl acetate (2×50 ml). The extracts were washed with water (50 ml) and saturated sodium chloride solution (50 ml), treated with charcoal and dried (MgSO$_4$). The solvent was removed by evaporation and the residue was triturated with ether/hexane (1:1 v/v) to give N-isobutoxycarbonyl-2-[4-(2-[methoxycarbonyl]vinyl)phenyl]-N-(3-methoxy-5-methylpyrazin-2-yl)pyridine-3-sulphonamide (0.99 g), m.p. 149–151° C.; microanalysis found: C, 57.7; H, 5.2; N, 10.6%; C$_{26}$H$_{28}$N$_4$O$_7$S requires: C, 57.8; H, 5.2; N, 10.4%.

EXAMPLE 56

Lithium hydroxide monohydrate (87 mg) was added to a solution of N-isobutoxycarbonyl-2-[4-(2-[methoxycarbonyl]vinyl)phenyl]-N-(3-methoxy-5-methylpyrazin-2-yl)pyridine-3-sulphonamide (250 mg) in tetrahydrofuran (6.2 ml) followed by methanol (2.5 ml) and water (2.5 ml). The reaction mixture was stirred at ambient temperature for 18 hours then evaporated to dryness. The residue was dissolved in water (50 ml), washed with ethyl acetate (50 ml), acidified with 8% aqueous citric acid to pH 3–4 and extracted with ethyl acetate (100 ml). The organic layer was extracted with saturated sodium bicarbonate solution (50 ml) and the aqueous phase separated, acidified with 8% aqueous citric acid and extracted with ethyl acetate (3×30 ml). The combined organic extracts were dried (MgSO$_4$) and evaporated to give 2-[-4-(2-carboxyvinyl)phenyl]-N-(3-methoxy-5-methylpyrazin-2-yl)pyridine-3-sulphonamide (108 mg) as a solid, m.p. 233–235° C.: $^1$H NMR ($d_6$-DMSO): 2.2 (s, 3H), 3.8 (s, 3H), 6.55 (d, 1H), 7.35 (br s, 1H), 7.45 (d, 2H), 7.55–7.75 (m, 4H), 8.45 (dd, 1H), 8.8 (dd, 1H), 10.1 (br s, 1H); mass spectrum (+ve ESP) 427 (M+H)$^+$.

The starting material N-isobutoxycarbonyl-2-[4-(2-[methoxycarbonyl]vinyl)phenyl]-N-(3-methoxy-5-methylpyrazin-2-yl)pyridine-3-sulphonamide was made as follows:

(i) Using an analogous procedure to that described in Example 11, part (ii), but starting from 4-formylphenylboronic acid, there was thus obtained (in 51% yield) N-isobutoxycarbonyl-2-(4-formylphenyl)-N-(3-methoxy-5-methylpyrazin-2-yl)pyridine-3-sulphonamide, m.p. 154–156° C.; $^1$H NMR (CDCl$_3$): 0.68 (d, 6H), 1.7 (septet, 1H), 2.53 (s, 3H), 3.83 (d, 2H), 4.0 (s, 3H), 7.58 (dd, 1H), 7.79 (d, 2H), 7.9 (s, 1H), 7.95 (d, 2H), 8.87 (dd, 1H), 8.97 (dd, 1H), 10.1 (s, 1H); mass spectrum (+ve ESP) 485 (M+H)$^+$.

(ii) N-isobutoxycarbonyl-2-(4-formylphenyl)-N-(3-methoxy-5-methylpyrazin-2-yl)pyridine-3-sulphonamide (500 mg) was added to carboxymethyl triphenylphosphonium bromide (429 mg) in a mixture of saturated aqueous sodium hydroxide (1.25 ml) and methylene chloride (4 ml) and stirred vigorously at ambient temperature for 1.5 hours. Water (20 ml) was added and the mixture extracted with dichloromethane (2×20 ml). The combined organic extracts were, washed with water (5 ml), dried (MgSO$_4$) and evaporated. The residue was purified by chromatography on a Mega Bond Elut column, eluting with a gradient of 0–30% ethyl acetate in hexane. Fractions containing the product were combined, evaporated and the residue was triturated with diethyl ether/isohexane (1:1 v/v) and filtered to give N-isobutoxycarbonyl-2-[4-(2-[methoxycarbonyl]vinyl)phenyl]-N-(3-methoxy-5-methylpyrazin-2-yl)pyridine-3-sulphonamide (366 mg), m.p 155–156° C.; $^1$H NMR (CDCl$_3$): 0.65 (d, 6H), 1.7 (septet, 1H), 2.5 (s, 3H), 3.82 (s, 3H), 3.85 (d, 2H), 3.98 (s, 3H), 6.48 (d, 1H), 7.4–7.8 (m, 7H), 7.9 (s, 1H), 8.86 (dd, 1H), 8.98 (dd, 1H).

EXAMPLE 57

2-[4-(3-hydroxy-2-methylpropyl)phenyl]-N-(3-methoxy-5-methylpyrazin-2-yl)pyridine-3-sulphonamide from Example 19 (100 mg) was heated in a mixture of acetic acid (0.5 ml) and acetic anhydride (0.5 ml) to 80° C. for 10 minutes and allowed to cool to ambient temperature. After 16 hours excess saturated aqueous sodium hydrogen carbonate was added cautiously and the product extracted into ethyl acetate (3×20 ml). The combined organic extract was dried (MgSO$_4$) and evaporated. The residue was purifed by elution with a gradient of 0–30% ethyl acetate/hexane through a silica gel Mega Bond Elut column (1 g) to give 2-[4-(3-acetoxy-2-methylpropyl)phenyl]-N-(3-methoxy-5-methylpyrazin-2-yl)pyridine-3-sulphonamide (70 mg) as a white foam; $^1$H NMR (CDCl$_3$): 0.98 (d, 3H), 1.58 (s, 3H), 2.11 (s, 3H), 2.1–2.3 (m, 1H), 2.51 (q, 1H), 2.85 (q, 1H), 3.80 (s, 3H), 3.97 (m, 2H), 6.69 (s, 1H), 7.2 (d, 2H), 7.29 (d, 2H), 8.67 (d, 1H), 8.80 (dd, 1H); mass spectrum (+ve ESP): 471.1 (M+H)$^+$.

EXAMPLE 58

Using an analogous procedure to that described in Example 9, but starting from 2-(4-(2-carboxypropyl)phenyl)-N-(isobutoxycarbonyl)-N-(3-methoxy-5-methylpyrazin-2-yl)pyridine-3-sulphonamide, there was thus obtained (in 31% yield) 2-[4-(2-carboxypropyl)phenyl] N-(3-methoxy-5-methylpyrazin-2-yl)pyridine-3-sulphonamide as a white powder; $^1$H NMR (CDCl$_3$): 1.23 (d, 3H), 2.28 (s, 3H), 2.80 (m, 1H), 3.13 (m, 1H), 3.83 (s, 3H), 7.71–7.33 (m, 5H), 7.51 (q, 1H), 8.68 (dd, 1H), 8.80 (dd, 1H); mass spectrum (+ve ESP): 443.1 (M+H)$^+$.

The starting material 2-[4-(2-carboxypropyl)phenyl]-N-(isobutoxycarbonyl)-N-(3-methoxy-5-methylpyrazin-2-yl)pyridine-3-sulphonamide was obtained as follows:
(i) A solution of diethyl methylmalonate (87 g) in absolute ethanol (100 ml) was added to a pre-formed solution of sodium (11.5 g) in ethanol (400 ml) under argon. A hot solution of p-bromobenzylbromide (125 g) in absolute alcohol (200 ml) was added rapidly with vigorous stirring, which was continued for 3 days and the solid so formed was removed by filtration. The filtrate was evaporated and the residue dissolved in ethyl acetate (1 l), washed with brine (250 ml), dried (MgSO$_4$) and evaporated. The residual oil was distilled under vacuum to give diethyl (4-bromophenyl)methylmalonate (150.7 g) b.p. 130–133/ 0.03 mm Hg; $^1$H NMR (d$_6$-DMSO): 1.33 (t, 6H), 1.4 (s, 3H), 3.27 (s, 2H), 4.30 (q, 4H), 7.23 (d, 2H), 7.6 (d, 2H).
(ii) A solution of sodium hydroxide (175 g) in water (800 ml) was added to a solution of diethyl (4-bromophenyl)

methylmalonate (150 g) in ethanol (850 ml) and the mixture was heated under reflux for 9 hours. Volatile material was removed by evaporation and the residue was dissolved in a solution of sodium hydroxide (130 g) in water (250 ml). The solution was heated under reflux for 2.5 hours, filtered through a bed of diatomaceous earth and the filtrate was acidified with 6M sulphuric acid. The mixture was extracted with ether (4×500 ml) and the extracts were dried (MgSO$_4$). The solution was concentrated and the residue was heated at 200° C. until evolution of carbon dioxide ceased. The residue was dissolved in 1M sodium hydroxide solution (500 ml) and the solution was acidified with 6M sulphuric acid. The mixture was extracted with ether (4×500 ml) and the extracts were dried (MgSO$_4$). The solvent material was removed by evaporation to give 3-(4-bromophenyl)-2-methylpropionic acid (91 g), m.p. 72–73 ° C.; $^1$H NMR (d$_6$-DMSO): 1.0 (d, 3H), 2.05–2.15 (m, 2H), 2.85–2.9 (m, 1H), 7.1 (d, 2H), 7.4 (d, 2H).
(iii) 3-(4-Bromophenyl)-2-methylpropionic acid (40 g) was finely divided and added portionwise over 30 minutes to thionyl chloride (75 ml). The mixture was stirred for 48 hours and then toluene (300 ml) was added. Volatile material was removed by evaporation and the residue was redissolved in toluene (300 ml). The solution was treated with charcoal and concentrated. The residual oil (36.6 g) was dissolved in dichloromethane (150 ml) and the solution was added dropwise over 1 hour to a solution of 2-amino-2-methylpropanol (25 g) in dichloromethane (300 ml) and toluene (300 ml) at –20° C. The mixture was stirred for 17 hours and water (300 ml) was added. The organic layer was separated, dried (MgSO$_4$) and concentrated. The residue was recrystallised from ethyl acetate to give N-(1-hydroxy-2-methylpropan-2-yl)-3-(4-bromophenyl)-2-methylpropionamide (34.4 g), m.p. 120–121 ° C.; microanalysis found: C, 53.9; H, 6.5; N, 4.5%; C$_{14}$H$_{20}$BrNO$_2$ requires: C, 53.5; H, 6.4; N, 4.5%.
(iv) A solution of methanesulphonyl chloride (11.4 g) in dichloromethane (50 ml) was added dropwise over 1 hour to a stirred mixture of N-(1-hydroxy-2-methylpropan-2-yl)-3-(4-bromophenyl)-2-methylpropionamide (31.4 g) and triethylamine (20.2 g) in dichloromethane (400 ml). The mixture was stirred for 2.5 hours and then water (300 ml) was added. The organic phase was separated, washed with water (200 ml) and saturated sodium chloride solution (200 ml) and dried (MgSO$_4$). Volatile material was removed by evaporation to give 2-[1-(4-bromophenyl)propan-2-yl]-4,4-dimethyloxazoline(26.4 g) as a syrup; $^1$H NMR (CDCl$_3$): 1.15 (d, 3H), 1.2 (s, 3H), 1.25 (s, 3H), 2.25–2.35 (m, 2H), 2.95–3.0 (m, 1H), 3.85 (s, 2H), 7.05 (d, 2H), 7.4 (d, 2H).
(v) Using an analogous procedure to that described in Example 8, part (ii), but starting from 2-[1-(4-bromophenyl)propan-2-yl]-4,4-dimethyloxazoline, there was obtained in 51% yield 4-[2-(4,4-dimethyloxazolin-2-yl)propyl]phenylboronic acid, m.p. 155–1 56° C.; $^1$H NMR (d$_6$-DMSO): 1.05 (s, 6H), 1.15 (d, 3H), 2.6–2.7 (m, 2H), 2.8–2.9 (m-1H), 3.85 (s, 2H), 7.15 (d, 2H), 7.7 (d,2H), 7.9 (s, 2H).
(vi) 4-[2-(4,4-dimethyloxazolin-2-yl)propyl]phenylboronic acid (2.68 g) was added to 3M hydrochloric acid (200 ml) and heated to 90° C. with stirring for 45 minutes. After cooling to ambient temperature, the solution was saturated with sodium chloride and extracted with ethyl acetate (3×100 ml). The combined organic extracts were dried (MgSO$_4$) and evaporated. The residue was triturated with isohexane to give 4-(2-carboxypropyl)

phenylboronic acid (1.59 g); $^1$H NMR (d$_6$-DMSO): 1.02 (d, 3H), 2.55–2.68 (m, 2H), 2.83–2.97 (m, 1H), 7.15 (d, 2H), 7.68 (d, 2H), 7.85 (s, 2H), 11.98 (br s, 1H).

(vii) Tetrakis(triphenylphosphine)palladium (0) (500 mg) was added to a deoxygenated solution of sodium carbonate (3.74 g), 4-(2-carboxypropyl)phenyl boronic acid (3.67 g) and 2-chloro-N-(isobutoxycarbonyl)-N-(3-methoxy-5-methyl-pyrazin-2-yl)pyridine-3-sulphonamide (6.1 g) in a mixture of water (30 ml), ethanol (75 ml) and toluene (75 ml). The mixture was stirred and heated under argon at 80° C. for 17 hours and then allowed to cool to ambient temperature. Ice water (5 g) was added and the reaction extracted with ethyl acetate (75 ml). The combined organic layers were extracted with saturated aqueous sodium carbonate solution (2×15 ml) and combined aqueous extracts were acidified to pH 2 with 2M hydrochloric acid and extracted with ethyl acetate (3×100 ml). The combined organic extracts were dried (MgSO$_4$) and evaporated to low volume affording crystalline material which was filtered and washed with diethyl ether to give N-(isobutoxycarbonyl)-2-(4-(2-carboxypropyl)phenyl)-N-(3-methoxy-5-methylpyrazin-2-yl)pyridine-3-sulphonamide (3.11 g); NMR $^1$H (d$_6$-DMSO): 0.61 (d, 6H), 1.09 (d, 3H), 1.50–1.73 (m, 1H), 2.55 (partly obscured by DMSO, 3H), 2.6–2.77 (m, 2H), 2.72–3.09 (m, 1H), 2.83 (d, 2H), 3.96 (s, 3H), 7.25 (d, 2H), 7.43 (d, 2H), 7.78 (dd, 1H), 8.15 (s, 1H), 8.83–8.96 (m, 2H), 12.14 (br s, 1H); mass spectrum (–ve ESP) 541.1 (M–H)$^-$.

EXAMPLE 59

2-[4-(3-hydroxy-2-methylpropyl)phenyl]-N-(3-methoxy-5-methylpyrazin-2-yl)pyridine-3-sulphonamide from Example 19 (100 mg) in dichloromethane (1 ml) was treated with trifluoroacetic acid (133 mg) followed by n-butylisocyanate (254 mg) under argon. The reaction was allowed to stand for 16 hour. Excess saturated sodium hydrogen carbonate was added and the mixture extracted with dichloromethane (2×10 ml). The combined organic extracts were washed with brine (10 ml), dried (MgSO$_4$) and evaporated. The residue was purifed by chromatography through a silica gel Mega Bond Elut column (1 g) eluting with a gradient of 0–100% ethyl acetate/hexane. Fractions enriched in the product were further purified by preparative reverse phase HPLC on a Dynamax 60A C18 column eluting with a gradient of 10–80% acetonitrile in water. There was thus obtained 2-[4-(2-methyl-3-[N-butylcarbamoyloxy]propyl)phenyl]-N-(3-methoxy-5-methyl-pyrazin-2-yl)pyridine-3-sulphonamide as a colourless oil (17.1 mg); $^1$H NMR (CDCl$_3$): 0.94 (m, 6H), 1.25–1.60 (m, 4H), 2.15 (broad m, 1H), 2.50 (q, 1H), 2.81 (q, 1H), 3.19 (t, 2H), 3.83 (s, 3H), 4.0 (d, 2H), 7.13–7.32 (m, 5H), 7.62 (q, 1H), 8.78 (dd, 1H), 8.85 (d, 1H); mass spectrum (+ve ESP) 528.2 (M+H)$^+$.

EXAMPLE 60

2-[4-(3-hydroxy-2-methylpropyl)phenyl]-N-(3-methoxy-5-methylpyrazin-2-yl)pyridine-3-sulphonamide (100 mg), obtained as described in Example 19, was dissolved in pyridine (3 ml) and pivaloyl chloride (309 mg; 0.32 ml) was added. After 2 hours at ambient temperature an excess of 8% aqueous citric acid was added and the reaction mixture was extracted with ethyl acetate (2×15 ml). The combined organic extracts were washed with brine (15 ml), dried (MgSO$_4$) and evaporated. The residue was purified by preparative reverse phase HPLC on a Dynamax 60A C18 column, eluting with a gradient of 20–80% acetonitrile in water, to give 2-[4-(2-methyl-3-pivaloyloxypropyl)phenyl]-N-(3-methoxy-5-methylpyrazin-2-yl)pyridine-3-sulphonamide (64 mg); $^1$H NMR (CDCl$_3$): 0.95 (d, 3H), 1.23 (s, 12H), 2.05–2.25 (br m, 1H), 2.6–2.9 (br m, 1H), 2.3 (s, 3H), 2.75–2.9 (br m, 1H), 3.80 (s, 3H), 3.90–4.08 (m, 2H), 6.55–6.8 (br, 1H), 7.1–7.4 (m, 5H), 7.5 (q, 1H), 8.68 (dd, 1H), 8.80 (dd, 1H); mass spectrum (+ve ESP) 513.3 (M+H)+, 535.3 (M+Na)$^+$.

EXAMPLE 61

Using an analogous procedure to that described in Example 9 but starting from N-(isobutoxycarbonyl)-2-(4-propanoylphenyl)-N-(3-methoxy-5-methylpyrazin-2-yl)pyridine-3-sulphonamide there was thus obtained (in 13% yield) 2-(4-propanoylphenyl)-N-(3-methoxy-5-methylpyrazin-2-yl)pyridine-3-sulphonamide, m.p. 125.5–127.3° C.; $^1$H NMR (CDCl$_3$): 1.25 (t, 3H), 2.27 (s, 3H), 3.04 (q, 2H), 3.77 (s, 3H), 6.7 (s, 1H), 7.35–7,6 (m, 4H), 8.0 (d, 2H), 8.7 (d, 1H), 8.8 (d, 1H); mass spectrum (CI$^+$) 413 (M.)$^+$.

The starting material N-(isobutoxycarbonyl)-2-(4-propanoylphenyl)-N-(3-methoxy-5-methylpyrazin-2-yl) pyridine-3-sulphonamide was made as follows:

Using an analogous procedure to that described in Example 11, part (ii), but starting from 4-propanoylphenylboronic acid (prepared by the method described in UK Patent Application GB2276161) there was thus obtained (in 51% yield) N-(isobutoxycarbonyl)-2-(4-propanoylphenyl)-N-(3-methoxy-5-methylpyrazin-2-yl) pyridine-3-sulphonamide; $^1$H NMR (CDCl$_3$): 0.65 (d, 6H), 1.25 (t, 3H), 1.6–1.85 (m, 1H), 2.5 (s, 3H), 3.02 (q, 2H), 3.82 (d, 2H), 4.0 (s, 3H), 7.55 (dd, 1H), 7.7 (d, 2H), 7.9 (s, 1H), 8.02 (d, 2H), 8.86 (dd, 1H), 8.95 (dd, 1H); mass spectrum (+ve ESP) 513 (M+H)$^+$.

EXAMPLE 62

Using an analogous procedure to that described in Example 9 but starting from N-(isobutoxycarbonyl)-2-(4-butanoylphenyl)-N-(3-methoxy-5-methylpyrazin-2-yl) pyridine-3-sulphonamide there was thus obtained (in 39% yield) 2-(4-butanoylphenyl)-N-(3-methoxy-5-methylpyrazin-2-yl)pyridine-3-sulphonamide, m.p. 130–131° C.; $^1$H NMR (CDCl$_3$): 1.05 (t, 3H) 1.8 (m, 2H), 2.25 (s, 3H), 2.95 (t, 2H), 3.8 (s, 3H), 6.68 (br s, 1H), 7.3–7.6 (m, 4H), 7.85–8.05 (m, 2H), 8.7 (d, 1H), 8.8 (dd, 1H); mass spectrum (+ve ESP) 427 (M+H)$^+$.

The starting material N-(isobutoxycarbonyl)-2-(4-butanoylphenyl)-N-(3-methoxy-5-methylpyrazin-2-yl) pyridine-3-sulphonamide was made as follows:

(i) 1-Bromo-4-butanoylbenzene (4.8 g), 1,2-ethanediol (4.48 ml) and p-toluenesulphonic acid were heated to reflux in benzene (50 ml) for 6 days. The reaction mixture was cooled and poured into a saturated aqueous solution of sodium bicarbonate (50 ml) and extracted with toluene (3×50 ml). The combined organic extracts were washed with brine (50 ml), dried (MgSO$_4$) and evaporated. The residual oil was distilled under vacuum to give 2-(4-bromophenyl)-2-propyl-1,3-dioxalane (4.25 g), b.p. 102° C. at 0.2 mm Hg; $^1$H NMR (acid free CDCl$_3$): 0.85 (t, 3H), 1.2–1.4 (m, 2H), 1.75–1.9 (m, 2H), 3.65–3.8 (m, 2H), 3.85–4.05 (m, 2H), 7.27–7.35 (m, 2H), 7.4–7.5 (m, 2H).

(ii) 2-(4-bromophenyl)-2-propyl-1,3-dioxalane (4.2 g) was dissolved in anhydrous tetrahydrofuran (50 ml) and cooled to −78° C. under an argon atmosphere. A 1.25M solution of n-butyl lithium in hexane (12.65 ml) was added with stirring, maintaining the temperature below −70° C. After a further 30 minutes, trimethyl borate (1.96 ml) was added slowly and the solution was stirred for a further 4 hours at −78° C. After allowing to warm to −5° C., 2M hydrochloric acid (50 ml) was added and the mixture was stirred for 18 hours. The organic phase was separated and the aqueous layer extracted with ethyl acetate (50 ml). The combined organic phases were washed with a saturated aqueous solution sodium bicarbonate (50 ml), brine (50 ml), dried (MgSO$_4$) and evaporated. The resulting solid was recrystallised from diethyl ether/hexane to give 4-butanoylphenylboronic acid (2.03 g), m.p. 173–177° C.; $^1$H NMR (CDCl$_3$): 1.05 (q, 3H), 1.8 (m, 2H), 2.9–3.1 (m, 2H), 7.8–8.1(m, 3H), 8.3 (d, 1H); mass spectrum (−ve ESP) 191 (M−H)−.

(iii) Using an analogous procedure to that described in Example 11, part (ii) but starting from 4-butanoylphenylboronic acid there was thus obtained (in 71% yield) N-(isobutoxycarbonyl)-2-(4-butanoylphenyl)-N-(3-methoxy-5-methylpyrazin-2-yl)pyridine-3-sulphonamide, m.p. 141–143° C.; $^1$H NMR (CDCl$_3$): 0.65 (d, 6H), 1.0 (t, 3H), 1.6–1.9 (m, 3H), 2.5 (s, 3H), 2.95 (t, 2H), 3.8 (d, 2H), 4.0 (s, 3H), 7.55 (m, 1H), 7.7 (d, 2H), 7.9 (s, 1H), 8.0 (d, 2H), 8.87 (dd, 1H), 8.98 (dd, 1H); mass spectrum (+ve ESP) 527 (M+H)$^+$.

EXAMPLE 63

Using an analogous procedure to that described in Example 9 but starting from N-isobutoxycarbonyl)-2-[4-(2-methylpropanoyl)phenyl]-N-(3-methoxy-5-methylpyrazin-2 -yl)pyridine-3-sulphonamide there was thus obtained (in 71.5% yield) 2-[4(2-methylpropanoyl)phenyl]-N-(3-methoxy-5-methylpyrazin-2-yl)pyridine-3-sulphonamide; $^1$H NMR (CDCl$_3$): 1.25 (d, 6H), 2.3 (s, 3H), 3.45–3.7 (m, 1H), 3.8 (s, 3H), 6.7 (br s, 1H), 7.3–7.6 (m, 4H), 7.87–8.07 (m, 2H), 8.68 (d, 1H), 8.82 (dd, 1H); mass spectrum (+ve ESP) 427 (M+H)$^+$.

The starting material N-(isobutoxycarbonyl)-2-[4-(2-methylpropanoyl)phenyl]-N-(3-methoxy-5-methylpyrazin-2-yl)pyridine-3-sulphonamide was made as follows:

(i) 4-Bromobenzonitrile (10 g) was dissolved in anhydrous diethyl ether (125 ml) and 2M isopropyl magnesium chloride in diethyl ether (30.24 ml) was added dropwise with stirring. The resulting solution was then heated to reflux for 18 hours. The reaction mixture was allowed to cool to ambient temperature and a saturated aqueous solution of ammonium chloride was added slowly with stirring. Stirring was continued for a further 2 hours. The organic phase was separated and the aqueous layer was extracted with diethyl ether (3×100 ml). The combined organic phases were washed with water (50 ml), then brine (50 ml), dried (MgSO$_4$) and evaporated to give 1-bromo-4-(2-methylpropanoyl)benzene (11.6 g); $^1$H NMR (CDCl$_3$): 1.15 (d, 6H), 3.1 (septet, 1H), 7.5–7.6 (m, 4H); mass spectrum (Cl+) 226 (M.)$^+$.

(ii) Using an analogous procedure to that described in Example 62, part (i), but starting from 1-bromo-4-(2-methylpropanoyl)benzene and 1,3-propanediol there was thus obtained (in 42% yield) 2-(4-bromophenyl)-2-isopropyl-1,3-dioxane (4.25 g), b.p. 116° C. at 0.4 mm Hg; $^1$H NMR (acid free CDCl$_3$): 0.8 (d, 3H), 1.15–1.25 (m, 1H), 1.85 (m, 2H), 2.0–2.1 (m, 1H), 3.68 (d of t, 2H), 3.75–3.85 (m, 2H) 7.15–7.25 (m, 2H), 7.45–7.55 (m, 2H): mass spectrum (CI+) 285 (M+H)$^+$.

(iii) Using an analogous procedure to that described in Example 62, part (ii), but starting from 2-(4-bromophenyl)-2-isopropyl-1,3-dioxane, there was thus obtained (in 82% yield) 4-(2-methylpropanoyl) phenylboronic acid; $^1$H NMR (CDCl$_3$): 1.15–1.25 (m, 6H), 3.4–3.85 (m, 2H), 7.75–8.1 (m, 3H), 8.25–8.4 (d, 1H); mass spectrum (−ve ESP) 191 (M−H)$^−$, dimer-H$_2$O 365 (M−H)$^−$.

(iii) Using an analogous procedure to that described in Example 11, part (ii), but starting from 4-(2-methylpropanoyl)phenylboronic acid, there was thus obtained (in 48% yield) N-(isobutoxycarbonyl)-2-(4-(2-methylpropanoyl)phenyl)-N-(3-methoxy-5-methylpyrazin-2-yl)pyridine-3-sulphonamide; $^1$H NMR (CDCl$_3$): 0.68 (d, 6H), 1.25 (d, 6H), 1.7 (septet, 1H), 2.5 (s, 3H), 3.58 (septet, 1H), 3.82 (d, 2H), 4.0 (s, 3H), 7.55 (q, 1H), 7.7 (d, 2H), 7.9 (s, 1H), 8.02 (d, 2H), 8.9 (dd, 1H), 8.98 (dd, 1H); mass spectrum (+ve ESP) 527 (M+H)$^+$.

EXAMPLE 64

2-[4-(2-carboxy-2-methylpropyl)phenyl]-N-(isobutoxycarbonyl)-N-(3-methoxy-5-methylpyrazin-2-yl) pyridine-3-sulphonamide (334 mg) was dissolved in methanol (10 ml) and sodium methoxide (324 mg) was added. The solution was heated to reflux for 4 hours, cooled and evaporated to dryness. The residue was partitioned between water (20 ml) and ethyl acetate (15 ml) and the organic layer was separated and washed with water (20 ml). The combined aqueous phases were acidified with 2M hydrochloric acid and extracted with ethyl acetate (3×25 ml). The combined organic extracts were dried (MgSO$_4$) and evaporated. The residue was triturated with isohexane to give 2-[4-(2-carboxy-2-methylpropyl)phenyl]-N-(3-methoxy-5-methylpyrazin-2-yl)pyridine-3-sulphonamide (117 mg); $^1$H NMR (d$_6$-DMSO): 1.1 (s, 6H), 2.24 (s, 3H), 2.85 (br, 2H), 3.80 (s, 3H); 7.13 (br, 2H), 7.35 (br d, 2H), 7.50 (br s, 1H), 7.57 (q, 1H), 8.78 (dd, 1H), 10.41 (br s, 1H); mass spectrum (+ve ESP) 457.2 (M+H)$^+$.

The starting material 2-[4-(2-carboxy-2-methylpropyl) phenyl]-N-(isobutoxycarbonyl)-N-(3-methoxy-5-methylpyrazin-2-yl)pyridine-3-sulphonamide was obtained as follows:

(i) A 1.25M solution of n-butyl lithium in hexane (32 ml) was cooled to 0° C. under an argon atmosphere and diisopropylamine (4.05 g; 5.24 ml) was added slowly. The resulting mixture was cooled to −70° C. and stirred while methyl isobutyrate (4.08 g; 4.58 ml) was added dropwise while maintaining the temperature at <−60° C. After a further 30 minutes at −70° C., a solution of 4-bromobenzyl bromide (10.0 g) in anhydrous tetrahydrofuran (20 ml) was added and the temperature was maintained at −70° C. for a further 1.5 hours. The reaction mixture was allowed to attain ambient temperature then heated to reflux for 18 hours. On cooling, the mixture was acidified with 8% aqueous citric acid and extracted with ethyl acetate (3×75 ml). Insoluble material at the interface was removed by filtration and the combined organic phase was washed with brine (20 ml), dried (MgSO$_4$) and evaporated. The residue was purified by vacuum flash chromatography on silica eluting with a gradient of 0–10% ethyl acetate in hexane to give 1-bromo-4-(2-methoxycarbonyl-2-methylpropyl)benzene (7.79 g); $^1$H NMR (d$_6$-DMSO): 1.13 (s, 6H); 2.79 (s, 2H), 3.60 (s, 3H), 7.04 (m, 2H), 7.46 (d of t, 2H); mass spectrum (CI+): 272 (M+H)$^+$.

(ii) 1-bromo-4-(2-methoxycarbonyl-2-methylpropyl) benzene (7.79 g) was dissolved in methanol (60 ml) and 2M aqueous sodium hydroxide solution (30 ml) was added. The solution was heated to reflux for 2 hours then cooled. The volume was reduced to ~25 ml by evaporation and the residue extracted with ethyl acetate (15 ml) then acidified with 2M hydrochloric acid and re-extracted with ethyl acetate (3×25 ml). The combined organic extract of the acidified aqueous phase was dried (MgSO$_4$) and evaporated to give 1-bromo-4-(2-carboxy-2-methylpropyl)benzene (6.1 g); $^1$H NMR (d$_6$-DMSO): 1.08 (s, 6H), 2.78 (s, 2H), 7.11 (m, 2H), 7.46 (m, 2H); mass spectrum (CI$^+$) 256 (M+H)$^+$.

(iii) 1-bromo-4-(2-carboxy-2-methylpropyl)benzene (1.93 g) was dissolved in anhydrous tetrahydrofuran (20 ml) and cooled to −70° C. A 1.25M solution of n-butyl lithium in hexane (18 ml) was added dropwise with stirring under an argon atmosphere, such that the temperature did not exceed −65° C. After a further 20 minutes, trimethyl borate was slowly added at −65° C. and the reaction mixture was allowed to attain −15° C. The reaction was quenched by the addition of a saturated aqueous solution of ammonium chloride (50 ml) and the mixture acidified by the addition of 2M hydrochloric acid. The organic phase was separated and the aqueous layer was extracted with ethyl acetate (2×50 ml). The combined organic phase was washed with brine (15 ml) and evaporated and the residue was triturated with hexane to give 4-(2-carboxy-2-methylpropyl)benzeneboronic acid (1.2 g); $^1$H NMR (DMSO-d$_6$): 1.06 (s, 6H), 2.78 (s, 2H), 7.11 (d, 2H), 7.67 (d, 2H), 7.9 (br s, 2H), 12.2 (br s, 1H); mass spectrum (−ve ESP) 221 (M−H)$^-$.

(iv) (2-Carboxy-2-methylpropyl)phenylboronic acid (608 mg), 2-chloro-N-isobutoxycarbonyl-N-(3-methoxy-5-methylpyrazin-2-yl)pyridine-3-sulphonamide (1.03 g) and sodium carbonate (583 mg) were added to a mixture of toluene (25 ml) ethanol (25 ml) and water (10 ml). The mixture was deoxygenated by alternatively bubbling argon through and evacuating (3 cycles) and tetrakis(triphenylphosphine)palladium(0) (100 mgs) was added. The reaction mixture was heated to 85° C. for 18 hours, cooled to ambient temperature and partitioned between water (15 ml) and ethyl acetate (25 ml). The organic phase was extracted with saturated aqueous sodium carbonate solution (15 ml) and the combined aqueous phases were washed with ethyl acetate (15 ml). The aqueous phase was acidified with 2M hydrochloric acid to pH 1 and extracted with ethyl acetate (3×30 ml). The combined organic extracts were dried (MgSO$_4$) and evaporated to give 2-[4-(2-carboxy-2-methylpropyl)phenyl]-N-(isobutoxycarbonyl)-N-(3-methoxy-5-methylpyrazin-2-yl)pyridine-3-sulphonamide (495 mg); $^1$H NMR (d$_6$-DMSO): 0.6 (d, 6H), 1.10 (s, 6H), 1.51–1.69 (m, 1H), 2.52 (s-partly obscured by DMSO), 2.87 (s, 2H), 3.82 (d, 2H), 3.95 (s, 3H), 7.20 (d, 2H), 7.43 (d, 2H), 7.79 (dd, 1H), 8.16 (s, 1H), 8.84–8.97 (m, 2H); mass spectrum (+ve ESP) 557.2 (M+H)$^+$.

EXAMPLE 65

2-[4-(2-Methylpropanoyl)phenyl]-N-(3-methoxy-5-methylpyrazin-2-yl)pyridine-3-sulphonamide (55 mg), obtained as described in Example 63, was dissolved in ethanol (2 ml) and sodium borohydride (20 mgs) was added. The resulting mixture was stirred at ambient temperature for 45 minutes and water (5 ml) was then added. The mixture was acidified by the addition of 2M hydrochloric acid to pH 2 and extracted with ethyl acetate (50 ml). The organic phase was dried (MgSO$_4$), evaporated and the residue was crystallised from ethyl acetate/hexane to give 2-[4-(1-hydroxy-2-methylpropyl)phenyl]-N-(3-methoxy-5-methylpyrazin-2-yl)pyridine-3-sulphonamide (33 mg); $^1$H NMR (CDCl$_3$+CD$_3$CO$_2$D): 0.83 (d, 3H), 0.95 (d, 3H), 1.95 (m, 1H), 2.25 (s 3H), 3.8 (s, 3H), 4.4 (d, 1H), 7.3 (s, 5H), 7.45 (dd, 1H), 8.65 (dd, 1H), 8.75 (dd, 1H); mass spectrum (+ve ESP) 429 (M+H)$^+$.

EXAMPLE 66

2-(4-Cyclopropylmethylphenyl)-N-isobutoxycarbonyl-N-(3-methoxy-5-methylpyrazin-2-yl)pyridine-3-sulphonamide (1.02 g) was dissolved in a mixture of tetrahydrofuran (30 ml) and ethanol (8 ml). Water (8 ml) and lithium hydroxide monohydrate (420 mg) were then added. The mixture was stirred at ambient temperature for 18 hours, acidified by the addition of 2M hydrochloric acid and extracted with ether (4×30 ml). The combined organic extract was dried (MgSO$_4$) and evaporated. The residue was purified by flash chromatography on a Mega Bond Elut column, eluting with a gradient of 0–100% ethyl acetate in hexane and fractions containing the product were combined and evaporated. The residue was crystallised from 1:10 ethyl acetate:hexane (50 ml) to give 2-[4-(2-cyclopropylmethylphenyl)-N-(3-methoxy-5-methylpyrazin-2-yl)pyridine-3-sulphonamide (378 mg); $^1$H NMR (d$_6$-DMSO): 0.23 (q, 2H), 0.52 (m, 2H), 1.0 (br m, 1H), 2.24 (s, 3H), 2.51 (partly obscured by DMSO), 3.32 (s, 3H), 7.23 (br d, 2H), 7.38 (d, 2H); 7.57 (dd, 1H), 8.42 (dd, 1H), 8.78 (dd, 1H) 10.1–10.7 (br s, 1H); mass spectrum (+ve ESP) 411.1 (M+H)$^+$.

The starting material 2-(4-cyclopropylmethylphenyl)-N-isobutoxycarbonyl-N-(3-methoxy-5-methylpyrazin-2-yl)pyridine-3-sulphonamide was obtained as follows:

(i) 4-Bromophenyl cyclopropyl ketone (5.63 g), hydrazine monohydrate (2.5 ml) and potassium hydroxide (3.33 g) were added to ethylene glycol (25 ml) and the mixture heated to reflux for 1 hour. The reaction mixture was cooled and partitioned between water (20 ml) and ethyl acetate (30 ml) and the organic layer was separated. The aqueous layer was extracted with ethyl acetate (30 ml) and the combined organic phases were washed with 2M hydrochloric acid (15 ml) and water (15 ml) then dried (MgSO$_4$) and evaporated. The residue was purified by chromatography on a Mega Bond Elut column, eluting with hexane to give 1-bromo-4-(cyclopropylmethyl)benzene (2.6 g); $^1$H NMR (CDCl$_3$): 0.2 (m, 2H), 0.55 (m, 2H), 2.50 (d, 2H), 7.14 (d, 2H), 7.41 (d, 2H); mass spectrum (EI+) 210 (M.)$^+$.

(ii) 1-Bromo-4-(cyclopropylmethyl)benzene (2.11 g) was dissolved in anhydrous tetrahydrofuran (20 ml) and cooled to −70° C. under an argon atmosphere. A 1.25M solution of n-butyl lithium in hexane (8.8 ml) was added at such a rate that the temperature did not exceed −65° C. with stirring, which was maintained for a further 30 minutes. Trimethyl borate was added slowly keeping the temperature below −60° C. and the reaction mixture was stirred for a further 1.5 hours at −70° C. After warming to −5° C., the reaction was quenched by the addition of a saturated aqueous solution of ammonium chloride (50 ml) and the organic phase was separated. The aqueous layer was extacted with ethyl acetate (2×30 ml) and combined organic phases were dried (MgSO$_4$) and evaporated to give 4-(cyclopropylmethyl)phenylboronic acid (1.52 g); $^1$H NMR (d$_6$-DMSO): 0.2 (d, 2H), 0.5 (d, 2H), 0.9–1.07 (m, 1H), 2.5 (partly obscured by DMSO), 7.2 (d, 2H), 7.7 (d, 2H); mass spectrum (−ve ESP) 175 (M−H)$^-$.

(iii) 4-(cyclopropylmethyl)benzeneboronic acid (1.5 g), 2-chloro-N-isobutoxycarbonyl-N-(3-methoxy-5-methylpyrazin-2-yl)pyridine-3-sulphonamide (2.99 g) and sodium carbonate (912 mg) were added to a mixture of toluene (66 ml), ethanol (33 ml) and water (24 ml). The mixture was deoxygenated by alternatively bubbling argon through and evacuating (3 cycles) and tetrakis (triphenylphosphine)palladium(0) (347 mgs) was added. The reaction mixture was heated to 80° C. for 18 hours with efficient stirring and, after cooling, ethyl acetate (50 ml) and water (30 ml) were added. The organic phase was separated and the aqueous layer extracted with ethyl acetate (2×30 ml). The combined organic phases were washed with brine (15 ml), dried (MgSO$_4$) and evaporated. The residue was purified by chromatography on a Mega Bond Elut column, eluting with a gradient of ethyl acetate in hexane (0–100%) to give 2-(4-cyclopropylmethylphenyl)-N-isobutoxycarbonyl-N-(3-methoxy-5-methylpyrazin-2-yl)pyridine-3-sulphonamide (1.85 g); $^1$H NMR (d$_6$-DMSO): 0.25 (q, 2H), 0.54 (m, 2H), 1.03 (M, 1H), 1.64 (m, 1H), 2.55 (s, 3H), 2.60 (d, 2H), 3.83 (d, 2H), 3.98 (s, 3H), 7.33 (d, 2H), 7.46 (d, 2H), 7.77 (dd, 1H), 8.15 (s, 1H), 8.10–8.95 (m, 2H); mass spectrum (+ve ESP) 511 (M+H)$^+$.

EXAMPLE 67

Racemic 2-[4-(2-carboxypropyl)phenyl]-N-(3-methoxy-5-methylpyrazin-2-yl)pyridine-3-sulphonamide (50 mg), obtained as described in Example 58, was separated in to its individual substantially optically pure isomers by HPLC in small aliquots on a Chiralpak A.D. chiral column, eluting with a mixture of hexane:ethanol:trifluoroacetic acid (85:15:0.1). The fractions containing the isomer of shorter retention time were combined and the solvent evaporated to give 2-[4-(2-carboxypropyl)phenyl]-N-(3-methoxy-5-methylpyrazin-2-yl)pyridine-3-sulphonamide Isomer A (2.5 mg); 99% optical purity determined by analytical chiral HPLC on a Chiralpak A.D. chiral column, retention time 10.832 minutes, eluted with hexane:ethanol:trifluoroacetic acid (85:15:0.1) at a flow rate of 1 ml/minute, detection wavelength 240 nm. The fractions containing the isomer of longer retention time were also combined and the solvent evaporated to give 2-[4-(2-carboxypropyl)phenyl]-N-(3-methoxy-5-methylpyrazin-2-yl)pyridine-3-sulphonamide Isomer B (1.1 mg); 91% optical purity determined by analytical chiral HPLC on a Chiralpak A. D. chiral column, retention time 12.336 minutes, eluted with hexane:ethanol:trifluoroacetic acid (85:15:0.1) at a flow rate of 1 ml/minute, detection wavelength 240 nm.

EXAMPLE 68

2-[4-(2-Carboxy-2-methylpropyl)phenyl]-N-(3-methoxy-5-methylpyrazin-2-yl)pyridine-3-sulphonamide (229 mg), obtained as described in Example 64, was dissolved in dry dimethyl formamide (6 ml) under an atmosphere of argon and sodium bicarbonate (42 mg) and methyl iodide (30 μl) were added. The reaction mixture was stirred for 18 hours and water (20 ml) was added. The solvent was decanted and the residual solid was dissolved in ethyl acetate (30 ml), dried (MgSO$_4$) and evaporated. The residue was triturated with ether (15 ml) and filtered to give 2-[4-(2-methoxycarbonyl-2-methylpropyl)phenyl]-N-(3-methoxy-5-methylpyrazin-2-yl)pyridine-3-sulphonamide (36 mg); $^1$H NMR (CDCl$_3$): 1.20 (s, 6H), 2.40 (s, 3H), 2.75 (s, 3H), 2.92 (s, 2H), 3.80 (s, 3H), 7.23 (d, 2H), 7.41 (dd, 1H), 7.54 (d, 2H), 7.19 (s, 1H), 8.48 (dd, 1H), 8.81 (dd, 1H); mass spectrum (+ve ESP) 471.2 (M+H)$^+$.

EXAMPLE 69

2-[4-(2-Carboxy-2-methylpropyl)phenyl]-N-(3-methoxy-5-methylpyrazin-2-yl)pyridine-3-sulphonamide (229 mg), obtained as described in Example 64, was dissolved in propan-1-ol (5 ml) and concentrated sulphuric acid (5 drops) was added. The reaction mixture was heated to reflux for 4 hours, cooled, basified to pH 8 by the addition of a saturated aqueous solution of sodium bicarbonate and extracted with ethyl acetate (3×10 ml). The combined organic phases were evaporated and the residue was purified by chromatography on a Mega Bond Elut column (1 g), eluting with a gradient of 0–100% ethyl acetate in hexane to give 2-[4-(2-propoxycarbonyl-2-methylpropyl)phenyl]-N-(3-methoxy-5-methylpyrazin-2-yl)pyridine-3-sulphonamide (24 mg); $^1$H NMR (CDCl$_3$): 0.94 (t, 3H), 1.20 (s, 6H), 1.66 (q, 2H), 2.28 (s, 3H), 2.92 (s, 2H), 3.84 (s, 3H), 4.05 (t, 2H), 7.14 (br d, 2H), 7.27 (partly obscured by CHCl$_3$), 7.48 (dd, 1H), 8.66 (dd, 1H), 8.79 (dd, 1H); mass spectrum (+ve ESP) 499.1 (M+H)$^+$.

EXAMPLE 70

A 60% dispersion of sodium hydride in mineral oil (50 mg) was suspended in dry dimethyl formamide (10 ml) and 2-amino-5-chloro-3-methoxypyrazine (prepared as described in Example 5(a–d)) (100 mg) was added in one portion. The mixture was stirred at ambient temperature for 45 minutes, cooled to 0° C. and a solution of 4-nitrophenyl 2-(4 -acetylphenyl)pyridine-3-sulphonate (250 mg) in dry dimethyl formamide (10 ml) was slowly added at 0° C. The reaction mixture was allowed to attain ambient temperature and stirred for 18 hours. Water (30 ml) and ethyl acetate (150 ml) were added, followed by 2M hydrochloric acid to pH4. The organic phase was separated and the aqueous layer was extracted with ethyl acetate (2×50 ml). The combined organic extracts were dried (MgSO$_4$), evaporated and the residue was purified by chromatography on a Mega Bond Elut column, eluting with 25% ethyl acetate in isohexane. There was thus obtained 2-(4-acetylphenyl)-N-(5-chloro-3-methoxypyrazin-2-yl)pyridine-3-sulphonamide (35 mg), m.p. 225–226° C.; $^1$H NMR (CDCl$_3$): 2.15 (s, 3H), 3.85 (s, 3H), 6.75 (s, 1H), 7.45–7.6 (m, 4H), 7.95–8.05 (m, 2H), 8.7 (dd, 1H), 8.85 (dd, 1H).

The starting material 4-nitrophenyl 2-(4-acetylphenyl) pyridine-3-sulphonate was obtained by an analogous procedure to that described in Example 5(ii) but starting from 4-acetylphenylboronic acid (itself prepared by the method described in UK Patent Application GB 2276161) in 54% yield; $^1$H NMR (CDCl$_3$): 2.7 (s, 3H), 7.0–7.1 (m, 2H), 7.5–7.6 (m, 1H), 7.7–7.8 (m, 2H), 8.0–8.1 (m, 2H), 8.1–8.2 (m, 2H), 8.45 (dd, 1H), 9.0 (dd, 1H); Mass spectrum (+ve ESP) 399 (M+H)$^+$.

EXAMPLE 71

Note: All Parts by Weight

The compounds of the invention may be administered for therapeutic or prophylactic use to warm-blooded animals such as man in the form of conventional pharmaceutical compositions, typical examples of which include the following:

| a) Capsule (for oral administration) | |
|---|---|
| Active ingredient * | 20 |
| Lactose powder | 578.5 |
| Magnesium stearate | 1.5 |

-continued b) Tablet (for oral administration)

| | |
|---|---|
| Active ingredient * | 50 |
| Microcrystalline cellulose | 400 |
| Starch (pregelatinised) | 47.5 |
| Magnesium stearate | 2.5 | c) Injectable Solution (for intravenous administration)

| | |
|---|---|
| Active ingredient * | 0.05–1.0 |
| Propylene glycol | 5.0 |
| Polyethylene glycol (300) | 3.0–5.0 |
| Purified water | to 100% | d) Injectable Suspension (for intramuscular administration)

| | |
|---|---|
| Active ingredient * | 0.05–1.0 |
| Methylcellulose | 0.5 |
| Tween 80 | 0.05 |
| Benzyl alcohol | 0.9 |
| Benzalkonium chloride | 0.1 |
| Purified water | to 100% |

Note: the active ingredient * may typically be an Example described hereinbefore or as a pharmaceutically acceptable salt. Tablets and capsules formulations may be coated in conventional manner in order to modify or sustain dissolution of the active ingredient. Thus, for example, they may be coated with a conventional enterically digestible coating.

Chemical Formulae

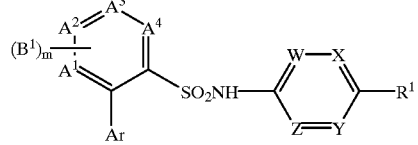

I

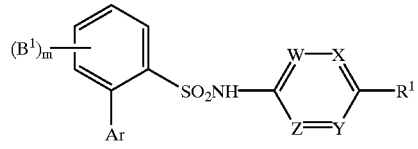

II

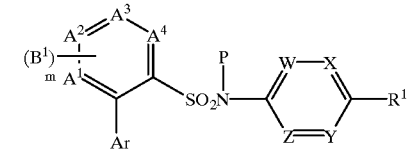

III

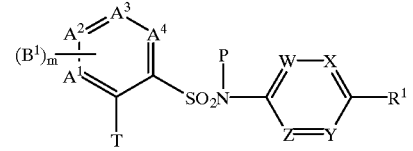

IV

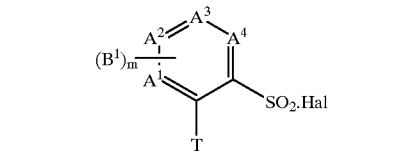

V

Chemical Formulae

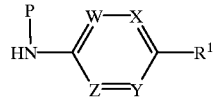

VI

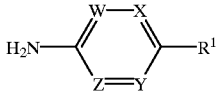

VII

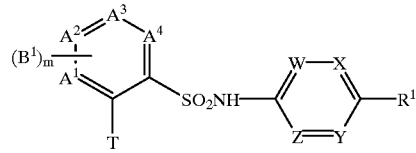

VIII

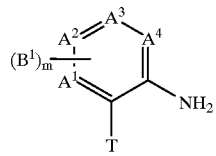

IX

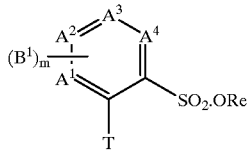

X

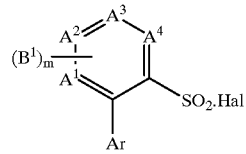

XI

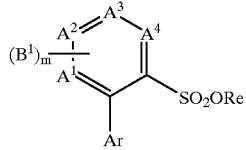

XII

What we claim is:

1. A compound of formula I;

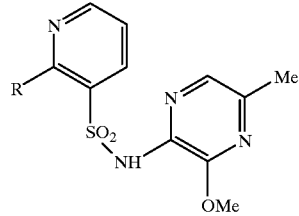

(I)

wherein R is a phenyl group having 1, 2 or 3 $R^1$ substituents wherein $R^1$ is independently selected from:

a five-membered heterocyclyl group containing 1, 2, 3 or 4 heteroatoms independently selected from nitrogen, oxygen and sulfur, a six-membered heterocyclyl group containing 1, 2 or 3 heteroatoms independently selected from nitrogen, oxygen and sulfur, or an N-oxide of any of the foregoing; or a physiologically-acceptable form of any of the foregoing; or a prodrug of any of the foregoing.

2. A compound according to claim 1, having formula II;

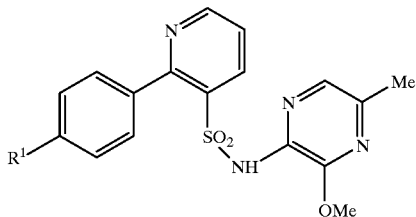

(II)

wherein $R^1$ is a group selected from 1-pyrrolidinyl, 2-oxo-1-pyrrolidinyl, 1-piperidinyl, 2-oxo-1-piperidinyl, morpholino or thiamorpholino.

3. A compound according to claim 1, selected from:

N-(3-methoxy-5-methylpyrazin-2-yl)-2-(4-[3-pyridyl]phenyl)pyridine-3-sulphonamide;

N-(3-methoxy-5-methylpyrazin-2-yl)-2-(4-[4-pyridyl]phenyl)pyridine-3-sulphonamide;

N-(3-methoxy-5-methylpyrazin-2-yl)-2-(4-[2-pyridyl]phenyl)pyridine-3-sulphonamide;

N-(3-methoxy-5-methylpyrazin-2-yl)-2-(4-[1,3,4-oxadiazol-2-yl]phenyl)pyridine-3-sulphonamide;

N-(3-methoxy-5-methylpyrazin-2-yl)-2-(4-[3methylisoxazol-5yl]phenyl)pyridine-3-sulphonamide;

N-(3-methoxy-5-methylpyrazin-2-yl)-2-(4-[3-methyl-1,2,4-oxadiazol-5-yl]phenyl)pyridine-3-sulphonamide;

N-(3-methoxy-5-methylpyrazin-2-yl)-2-(4-[1,2,4-oxadiazol-3-yl]phenyl)pyridine-3-sulphonamide;

N-(3-methoxy-5-methylpyrazin-2-yl)-2-(4-[5-methyl-1,2,4-oxadiazol-3-yl]phenyl)pyridine-3-sulphonamide;

N-(3-methoxy-5-methylpyrazin-2-yl)-2-(4-[pyrimidin-2-yl]phenyl)pyridine-3-sulphonamide;

N-(3-methoxy-5-methylpyrazin-2-yl)-2-{4-[(3-pyridyl)methoxymethyl]phenyl}pyridine-3-sulphonamide, and N-(3-methoxy-5-methylpyrazin-2-yl)-2-[4-morpholinophenyl]pyridine-3-sulphonamide, or a physiologically-acceptable composition comprising said compound.

4. A polymorph, tautomer, or solvate of a compound according to claim 1, or a physiologically-acceptable composition comprising any of the foregoing; or a mixture of any of the foregoing.

5. A pharmaceutical composition comprising a compound according to claim 1, and a pharmaceutically-acceptable diluent or carrier.

6. A method of antagonizing the activity of endothelin in a human or other warm-blooded animal comprising administering a therapeutically-effective amount of a compound according to claim 1, or of a physiologically-acceptable form thereof.

7. A method of treating a disease or medical condition caused by elevated or abnormal levels of endothelin in a human or other warm-blooded animal comprising administering a amount of a compound according to claim 1, or an amount of a physiologically-acceptable form thereof, sufficient to effectively antagonize the activity of said endothelin.

8. A method according to claim 7, wherein the disease or medical condition is congestive heart failure.

* * * * *